United States Patent
Lui et al.

(10) Patent No.: US 11,158,817 B2
(45) Date of Patent: Oct. 26, 2021

(54) COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Jinhyun Lui, Suwon-si (KR); Changwoo Kim, Suwon-si (KR); Eun Sun Yu, Suwon-si (KR); Kipo Jang, Suwon-si (KR); Ho Kuk Jung, Suwon-si (KR); Youngkyoung Jo, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 82 days.

(21) Appl. No.: 16/468,779

(22) PCT Filed: Oct. 26, 2017

(86) PCT No.: PCT/KR2017/011928
§ 371 (c)(1),
(2) Date: Jun. 12, 2019

(87) PCT Pub. No.: WO2018/128255
PCT Pub. Date: Jul. 12, 2018

(65) Prior Publication Data
US 2020/0098998 A1    Mar. 26, 2020

(30) Foreign Application Priority Data

Jan. 5, 2017    (KR) .................. 10-2017-0001941
Oct. 26, 2017   (KR) .................. 10-2017-0140115

(51) Int. Cl.
*H01L 51/50* (2006.01)
*H01L 51/00* (2006.01)
(Continued)

(52) U.S. Cl.
CPC ........ *H01L 51/0073* (2013.01); *C07D 405/04* (2013.01); *C07D 487/04* (2013.01);
(Continued)

(58) Field of Classification Search
None
See application file for complete search history.

(56) References Cited

U.S. PATENT DOCUMENTS 6,229,012 B1    5/2001   Hu et al.
9,209,406 B2   12/2015   Mizutani et al.
(Continued)

FOREIGN PATENT DOCUMENTS

CN    102851329 A    1/2013
CN    103232843 A    8/2013
(Continued)

OTHER PUBLICATIONS

International Search report for PCT/KR2017/011928 filed on Oct. 26, 2017.
(Continued)

*Primary Examiner* — Gregory D Clark
(74) *Attorney, Agent, or Firm* — Lee IP Law, P.C.

(57) ABSTRACT

Disclosed are a compound for an organic optoelectronic device represented by Chemical Formula 1, a composition for an organic optoelectronic device, organic optoelectronic device including the same, and a display device.
Details of Chemical Formula 1 are the same as defined in the specification.

14 Claims, 1 Drawing Sheet

(51) Int. Cl.
*C07D 405/04* (2006.01)
*C09K 11/06* (2006.01)
*C07D 487/04* (2006.01)

(52) U.S. Cl.
CPC .......... *C09K 11/06* (2013.01); *H01L 51/0052* (2013.01); *H01L 51/0067* (2013.01); *H01L 51/0072* (2013.01); *C09K 2211/1018* (2013.01); *H01L 51/508* (2013.01); *H01L 51/5012* (2013.01); *H01L 51/5016* (2013.01); *H01L 2251/5384* (2013.01)

(56) References Cited

U.S. PATENT DOCUMENTS

| | | | |
|---|---|---|---|
| 9,893,290 | B2 | 2/2018 | Min et al. |
| 2004/0164292 | A1* | 8/2004 | Tung ................ G02F 1/133603 257/40 |
| 2006/0046342 | A1 | 3/2006 | Karg et al. |
| 2007/0141387 | A1 | 6/2007 | Nakano et al. |
| 2013/0264560 | A1 | 10/2013 | Dobbs et al. |
| 2014/0001456 | A1 | 1/2014 | Mizutani et al. |
| 2014/0361258 | A1 | 12/2014 | Hwang et al. |
| 2015/0028320 | A1 | 1/2015 | Kinoshita et al. |
| 2015/0171336 | A1 | 6/2015 | Park et al. |
| 2015/0171340 | A1 | 6/2015 | Lee |
| 2015/0207082 | A1 | 7/2015 | Dyatkin |
| 2015/0349268 | A1 | 12/2015 | Zeng et al. |
| 2016/0028021 | A1 | 1/2016 | Zeng |
| 2016/0329502 | A1 | 11/2016 | Dyatkin et al. |
| 2017/0025618 | A1 | 1/2017 | Zheng et al. |
| 2017/0117488 | A1 | 4/2017 | Ahn |
| 2018/0033975 | A1 | 2/2018 | Kim |

FOREIGN PATENT DOCUMENTS

| | | | | |
|---|---|---|---|---|
| CN | 103380508 | A | 10/2013 | |
| CN | 104271703 | A | 1/2015 | |
| CN | 104812750 | A | 7/2015 | |
| CN | 104885247 | A | 9/2015 | |
| CN | 104995187 | A | 10/2015 | |
| CN | 105153130 | A | 12/2015 | |
| CN | 105315219 | A | 2/2016 | |
| CN | 105315265 | A | 2/2016 | |
| CN | 105359290 | A | 2/2016 | |
| CN | 105473684 | A | 4/2016 | |
| CN | 107093677 | A | 8/2017 | |
| CN | 107325090 | A | 11/2017 | |
| CN | 108290854 | A | 7/2018 | |
| EP | 2 966 706 | A2 | 1/2016 | |
| EP | 3 268 449 | A1 | 2/2016 | |
| JP | 2014/040423 | A | 3/2014 | |
| JP | 2014-123687 | A | 7/2014 | |
| JP | 5541167 | B2 | 7/2014 | |
| JP | 2014-157947 | A | 8/2014 | |
| JP | 5847420 | B2 | 1/2016 | |
| JP | 2016/019002 | A | 2/2016 | |
| JP | 2016-506414 | A | 3/2016 | |
| JP | 2016-525081 | A | 8/2016 | |
| JP | 2018-514081 | A | 5/2018 | |
| KR | 10-2011-0096453 | | 8/2011 | |
| KR | 10-2010-0118690 | | 11/2011 | |
| KR | 10-2012-0129733 | A | 11/2012 | |
| KR | 10-2013-0036048 | A | 4/2013 | |
| KR | 10-2013-0061371 | | 6/2013 | |
| KR | 10-2014-0005804 | A | 1/2014 | |
| KR | 10-2014-0010133 | A | 1/2014 | |
| KR | 10-1423067 | B1 | 7/2014 | |
| KR | 10-2014-0144550 | A | 12/2014 | |
| KR | 10-2015-0036736 | A | 4/2015 | |
| KR | 10-2015-0042335 | | 4/2015 | |
| KR | 10-2015-0070860 | A | 6/2015 | |
| KR | 10-1542714 | B1 | 7/2015 | |
| KR | 10-2015-0116776 | A | 10/2015 | |
| KR | 10-2015-0129282 | A | 11/2015 | |
| KR | 10-2015-0131998 | A | 11/2015 | |
| KR | 10-2015-0136942 | | 12/2015 | |
| KR | 10-2016-0006633 | | 1/2016 | |
| KR | 10-1593465 | B1 | 2/2016 | |
| KR | 10-2016-0028524 | A | 3/2016 | |
| KR | 10-2016-0034528 | A | 3/2016 | |
| KR | 2016-37909 | * | 3/2016 | .............. H01I 51/50 |
| KR | 10-2016-0038006 | A | 4/2016 | |
| KR | 10-2016-0055556 | A | 5/2016 | |
| KR | 10-2016-0080090 | A | 7/2016 | |
| KR | 10-2016-0110078 | A | 9/2016 | |
| KR | 10-2017-0022865 | | 3/2017 | |
| KR | 10-2017-0089599 | A | 8/2017 | |
| KR | 10-2017-0116992 | A | 10/2017 | |
| KR | 10-2017-0141144 | A | 12/2017 | |
| TW | 201609712 | A | 3/2016 | |
| TW | 201619152 | A | 6/2016 | |
| WO | WO 2010/044342 | A1 | 4/2010 | |
| WO | WO 2013/077352 | A1 | 5/2013 | |
| WO | WO 2014/054912 | A1 | 4/2014 | |
| WO | WO 2014208755 | A1 | 12/2014 | |
| WO | WO 2015/000549 | A1 | 1/2015 | |
| WO | WO 2015/156587 | A1 | 10/2015 | |
| WO | WO 2015/160224 | A1 | 10/2015 | |
| WO | WO 2016/076384 | A1 | 5/2016 | |
| WO | WO 2016084962 | A1 | 6/2016 | |
| WO | WO 2016 148390 | A1 | 9/2016 | |
| WO | WO 2016/172414 | A1 | 10/2016 | |
| WO | WO 2017/016630 | A1 | 2/2017 | |
| WO | WO 2017/146466 | A1 | 8/2017 | |
| WO | WO 2017/171420 | A1 | 10/2017 | |
| WO | WO 2018/016742 | A1 | 1/2018 | |
| WO | WO 2018/021663 | A1 | 2/2018 | |
| WO | WO 2018/062659 | A1 | 4/2018 | |
| WO | WO 2018/093026 | A1 | 5/2018 | |
| WO | WO 2018/097461 | A1 | 5/2018 | |
| WO | WO 2018/128255 | A1 | 7/2018 | |

OTHER PUBLICATIONS

European Search Report dated Dec. 19, 2019, Application No. 17820373.3.
European Search Report dated Jan. 8, 2020, Application No. 17820372.5.
Japanese Office action dated Sep. 29, 2020, received in Japanese Application No. 2018-568699.
Japanese Notice of Allowance dated Oct. 6, 2020, received in Japanese Application No. 2019-503551.
Extended European Search Report dated Feb. 17, 2020, European Patent Application No. 17827792.7.
Extended European Search Report dated Feb. 28, 2020, European Patent Application No. 17834608.6.
Office action received in copending related U.S. Appl. No. 16/097,657.
Yu, Organic Electronics, 38, 2016, 301-306.
U.S. Office action received in co pending U.S. Appl. No. 16/099,507, dated Apr. 16, 2021.
U.S. Office action received in co pending U.S. Appl. No. 16/099,523, dated Apr. 19, 2021.
European Office action dated Mar. 25, 2021.
U.S. Office Action received in Co Pending U.S. Appl. No. 16/321,228 dated Jun. 25, 2021.

* cited by examiner

[Figure 1]
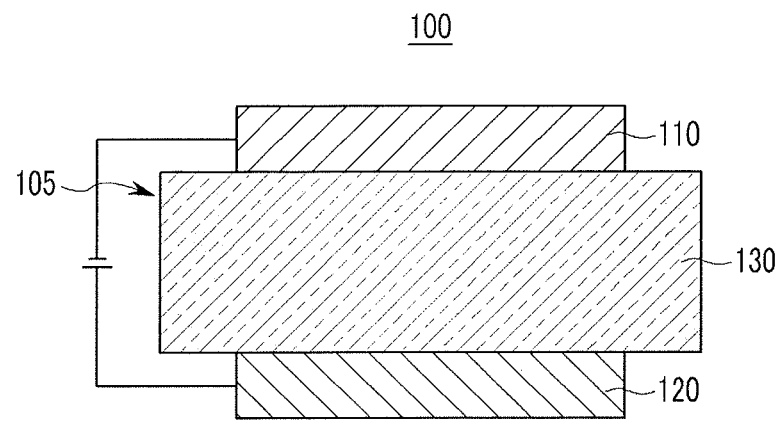
[Figure 2]
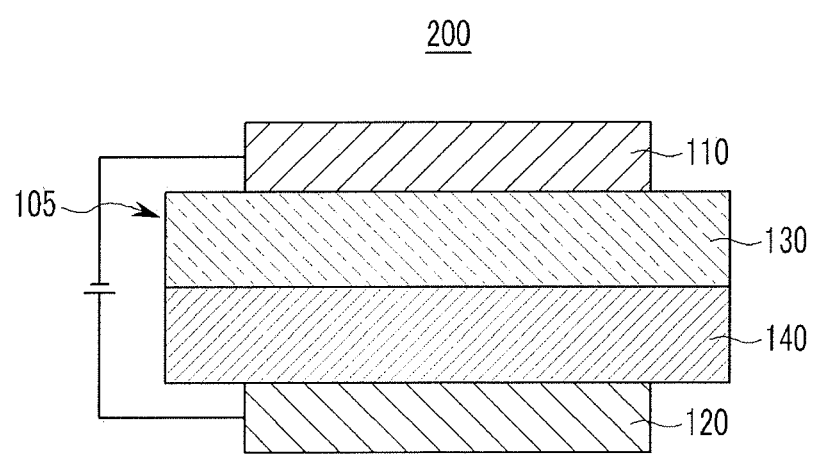

COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

CROSS-REFERENCE TO THE RELATED APPLICATION

This is the U.S. national phase application based on PCT Application No. PCT/KR2017/011928, filed Oct. 26, 2017, which is based on Korean Patent Application No. 10-2017-0001941, filed Jan. 5, 2017, and Korean Patent Application No. 10-2017-0140115, filed on Oct. 26, 2017, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device are an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic device capable of realizing an organic optoelectronic device having high efficiency and a long life-span.

Technical Solution

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

According to one embodiment, a compound for an organic optoelectronic device represented by Chemical Formula 1 is provided.

[Chemical Formula 1]

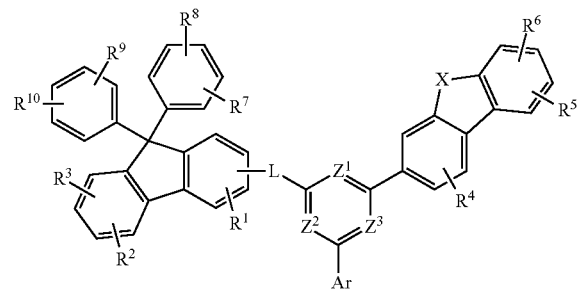

In Chemical Formula 1, $Z^1$ to $Z^3$ are independently N or $CR^a$, at least two of $Z^1$ to $Z^3$ are N, X is O or S, L is a single bond, a substituted or unsubstituted C6 to C30 arylene group, or a substituted or unsubstituted C2 to C30 heteroarylene group, Ar is a substituted or unsubstituted C6 to C30 aryl group, and $R^a$ and $R^1$ to $R^{10}$ are independently hydrogen, deuterium, a substituted or unsubstituted C1 to C10 alkyl group, a substituted or unsubstituted C6 to C30 aryl group, or a combination thereof, wherein "substituted" refers to replacement of at least one hydrogen by deuterium, a C1 to C20 alkyl group, a C6 to C30 aryl group, or a C2 to C30 heteroaryl group.

According to another embodiment, a composition for an organic optoelectronic device includes the first compound for an organic optoelectronic device; and a second compound for an organic optoelectronic device including a carbazole moiety represented by Chemical Formula 2.

[Chemical Formula 2]

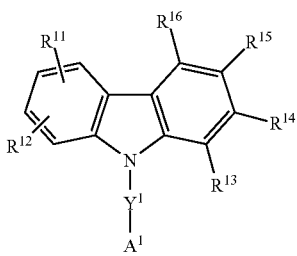

In Chemical Formula 2, $Y^1$ is a single bond, a substituted or unsubstituted C6 to C30 arylene group, or a substituted or unsubstituted C2 to C30 heteroarylene group, $A^1$ is a substituted or unsubstituted C6 to C30 aryl group, or a substituted or unsubstituted C2 to C30 heterocyclic group, $R^{11}$ to $R^{16}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and $R^{13}$ to $R^{16}$ are independently present or adjacent groups of $R^{11}$ to $R^{16}$ are linked with each other to form a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring, wherein the "substituted" refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode, wherein the organic layer includes the compound for an organic optoelectronic device or the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example embodiment of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group. a C3 to C30 heterocycloalkyl group, a C6 to C30 aryl group, or a C2 to C30 heteroaryl group. In a specific example embodiment of the present invention, "substituted" refers to replacement of at least one hydrogen of a substituent or a compound by deuterium. a C1 to C20 alkyl group, a C6 to C30 aryl group, or a C2 to C30 heteroaryl group. In a specific example embodiment of the present invention, "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In a specific example embodiment of the present invention, "substituted" refers to replacement of at least one hydrogen of a substituent or a compound by deuterium, a C to C5 alkyl group, a C6 to C18 aryl group, a dibenzofuranyl group, or a dibenzothiophenyl group. In a specific example embodiment of the present invention, "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group. a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group. a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

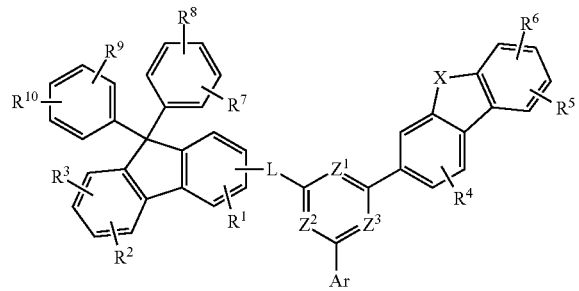

In Chemical Formula 1,
$Z^1$ to $Z^3$ are independently N or $CR^a$,
at least two of $Z^1$ to $Z^3$ are N,
X is O or S,
L is a single bond, a substituted or unsubstituted C6 to C30 arylene group, or a substituted or unsubstituted C2 to C30 heteroarylene group,
Ar is a substituted or unsubstituted C6 to C30 aryl group, and
$R^a$ and $R^1$ to $R^{10}$ are independently hydrogen, deuterium, a substituted or unsubstituted C1 to C10 alkyl group, a substituted or unsubstituted C6 to C30 aryl group, or a combination thereof,
wherein "substituted" refers to replacement of at least one hydrogen by deuterium, a C1 to C20 alkyl group, a C6 to C30 aryl group, or a C2 to C30 heteroaryl group.

In a specific example embodiment of the present invention, the "substituted" refers to replacement of at least one hydrogen by deuterium, a C1 to C20 alkyl group, or a C6 to C30 aryl group, and more specifically replacement of at least one hydrogen by deuterium, a C1 to C10 alkyl group, a phenyl group, a biphenyl group, or a naphthyl group.

A compound for an organic optoelectronic device according to the present invention includes an ET core including an N-containing 6-membered ring that is directly linked with dibenzofuran or dibenzothiophene at the position No. 2 without a linking group, and thereby a LUMO energy band is effectively expanded, planarity of molecular structure is increased, the compound has a structure easily to accept electrons when an electric field is applied, and thus an organic optoelectronic device including the compound for an organic optoelectronic device has a lowered driving voltage. In addition, such an expansion of LUMO and fusion of rings increase stability for electrons of the ET core and improves life-span effectively.

In addition, since a glass transition temperature (Tg) of the compound substituted with diaryl fluorene is increased compared with one substituted with dialkyl fluorene, stability of the compound may be increased, but degradation of the compound may be prevented when applied to a device.

A glass transition temperature (Tg) may be related with thermal stability of a compound and a device including the compound. In other words, when a compound for an organic optoelectronic device having a high glass transition temperature (Tg) is applied to an organic light emitting diode in a form of a thin film, degradation by the temperature may be suppressed in a subsequent process, for example an encapsulation process after depositing the compound for an organic optoelectronic device, life-span characteristics of the organic compound and a device may be ensured.

Particularly, when the diphenyl fluorene is substituted at a position No. 4, a much lower deposition temperature at the same molecular weight may be secured than when the fluorene is substituted at the other positions, and thus the compound may be prevented from degradation when stored or deposited at a high temperature.

Accordingly, a driving voltage, efficiency, and life-span characteristics of an organic optoelectronic device may be improved by applying the compound thereto.

In an example embodiment of the present invention, Chemical Formula 1 may be for example represented by one of Chemical Formula 1A, Chemical Formula 1B, and Chemical Formula 1C according to a substitution position of diphenyl fluorene.

[Chemical Formula 1A]

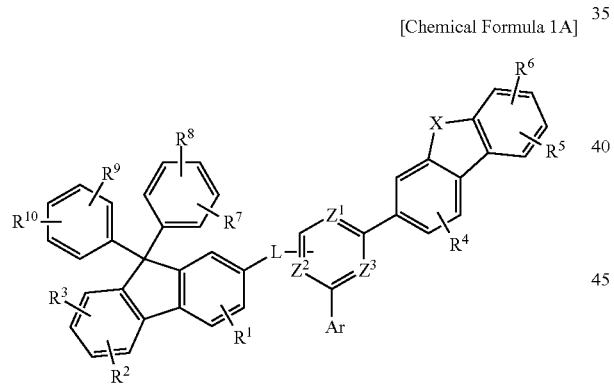

[Chemical Formula 1B]

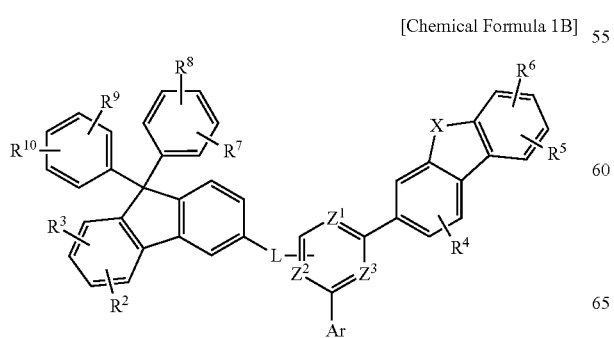

[Chemical Formula 1C]

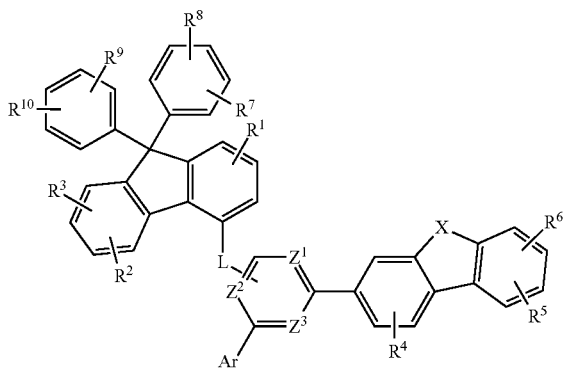

In Chemical Formula 1A, Chemical Formula 1B, and Chemical Formula 1C, $Z^1$ to $Z^3$, X, L, Ar, and $R^1$ to $R^{10}$ are the same as described above.

In an example embodiment of the present invention, Chemical Formula 1 may be for example represented by one of Chemical Formula 1-I, Chemical Formula 1-II and Chemical Formula 1-III according to the number and the position of N included in $Z^1$ to $Z^3$.

[Chemical Formula 1-I]

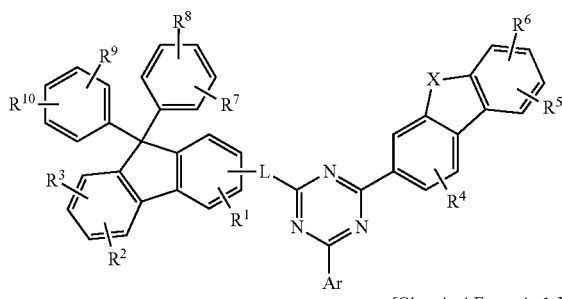

[Chemical Formula 1-II]

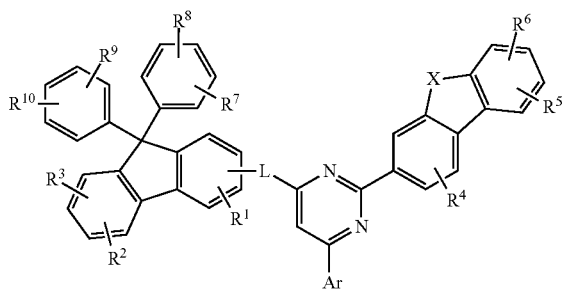

[Chemical Formula 1-III]

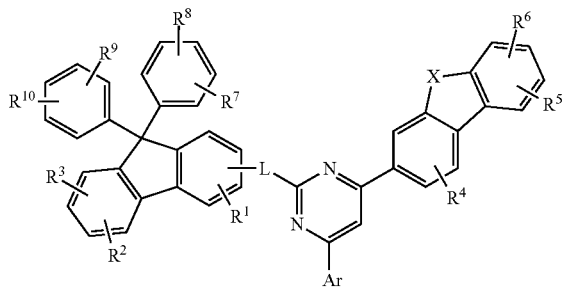

In Chemical Formula 1-I, Chemical Formula 1-II, and Chemical Formula 1-III, X, L, Ar, and $R^1$ to $R^{10}$ are the same as above and $R^{a1}$ to $R^{a3}$ are the same as $R^a$.

In a specific example embodiment of the present invention, a structure represented by Chemical Formula 1-I where $Z^1$ to $Z^3$ are all N may be preferable.

Specifically, L of Chemical Formula 1 may be a single bond, and more specifically, L of Chemical Formula 1A, Chemical Formula 1B, Chemical Formula 1C, Chemical Formula 1-I, Chemical Formula 1-II, and Chemical Formula 1-III may be a single bond.

For example, Chemical Formula 1 may be preferably a structure represented by Chemical Formula 1C or Chemical Formula 1-I, and most preferably a structure represented by Chemical Formula 1C.

In one example embodiment of the present invention, Ar may be a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group. Specifically, Ar may be a phenyl group, a biphenyl group, or a terphenyl group. The biphenyl group may be more specifically a meta-biphenyl group or a para-biphenyl group and the terphenyl group may be more specifically meta-terphenyl group, an iso-type meta-linked terphenyl group.

In a specific example embodiment of the present invention, $R^1$ to $R^{10}$ may independently be hydrogen. deuterium, a methyl group, an ethyl group, a n-propyl group. an iso-propyl group, a substituted or unsubstituted phenyl group, or a substituted or unsubstituted naphthyl group, specifically $R^1$ to $R^{10}$ may independently be hydrogen, a methyl group, an ethyl group, or a phenyl group, and In a more specific example embodiment of the present invention, $R^1$ to $R^{10}$ may be hydrogen or a phenyl group, and more specifically all $R^1$ to $R^{10}$ may be hydrogen.

The compound for an organic optoelectronic device represented by Chemical Formula 1 may be for example selected from compounds of Group 1, but is not limited thereto.

[Group 1]

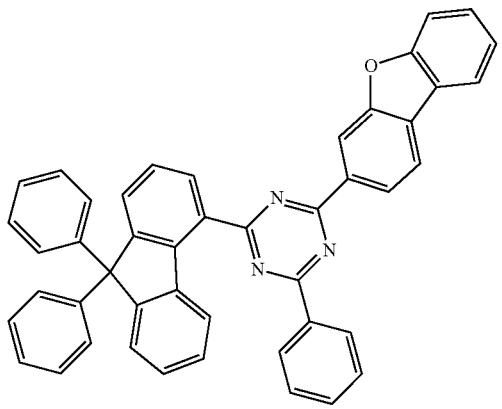
[A-1]

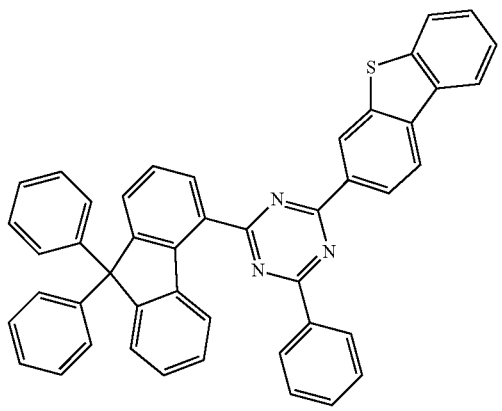
[A-2]

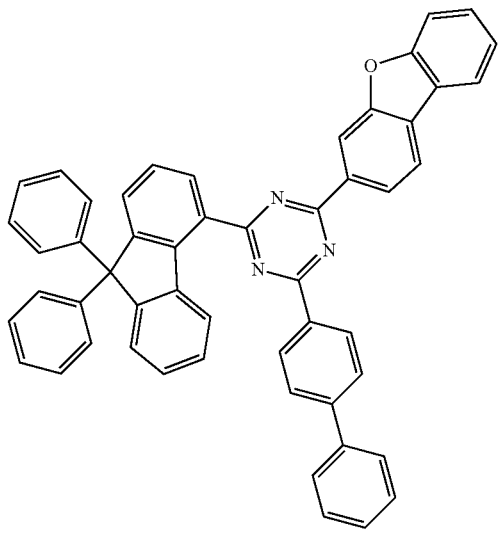
[A-3]

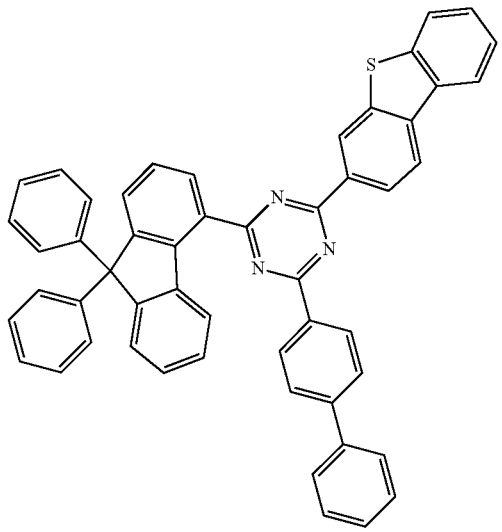
[A-4]

[A-5]
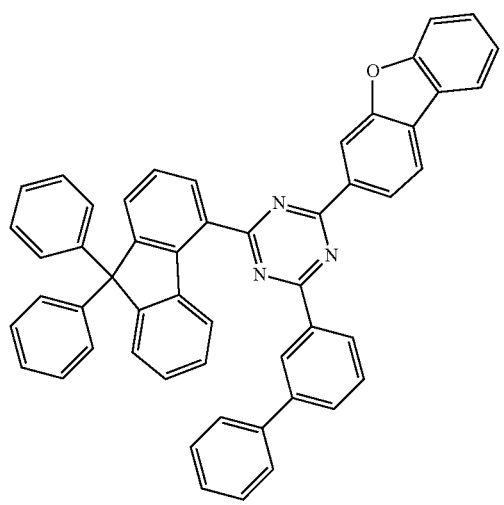
[A-8]
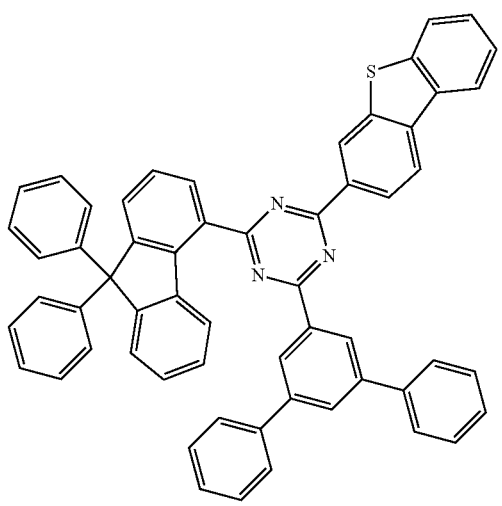
[A-6]
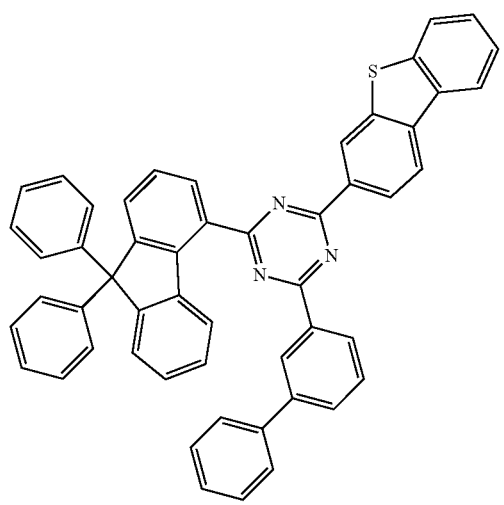
[A-9]
[A-7]
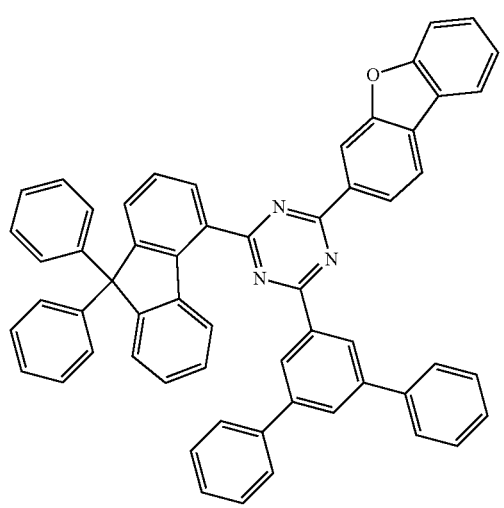
[A-10]
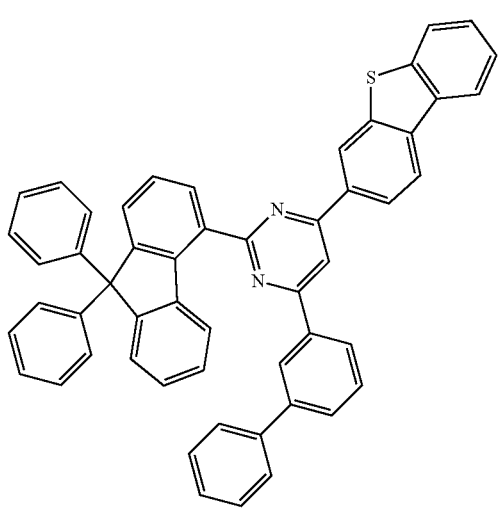

[A-11]
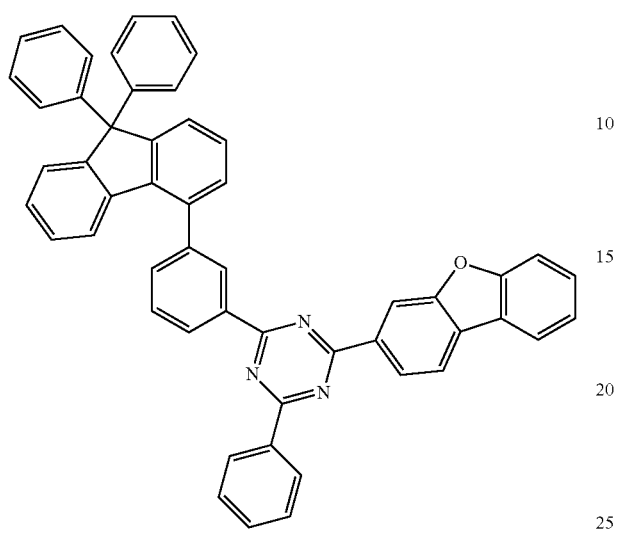
[A-12]
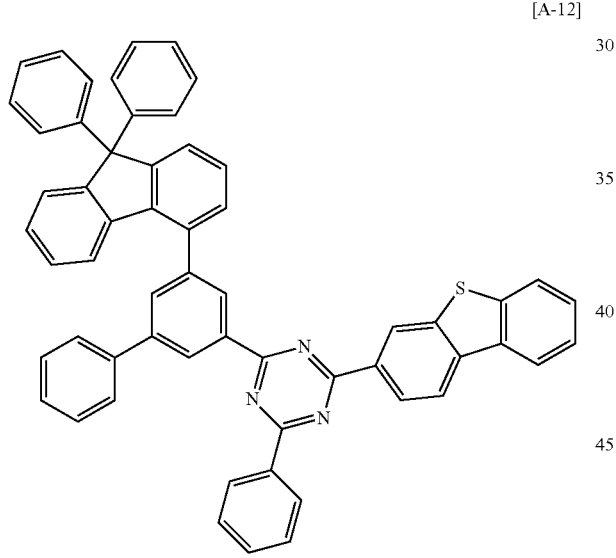
[A-13]
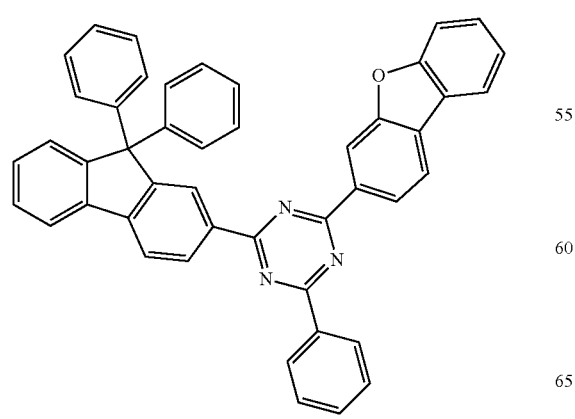
[A-14]
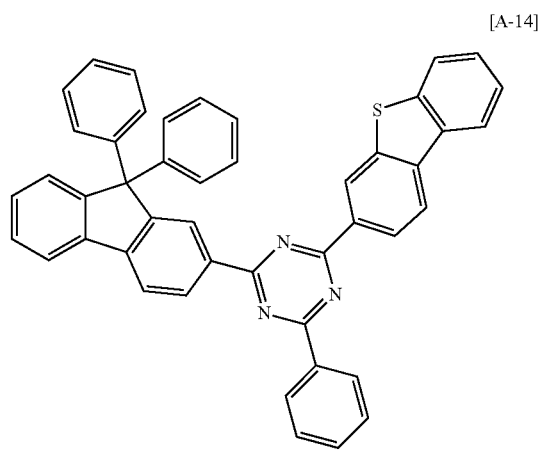
[A-15]
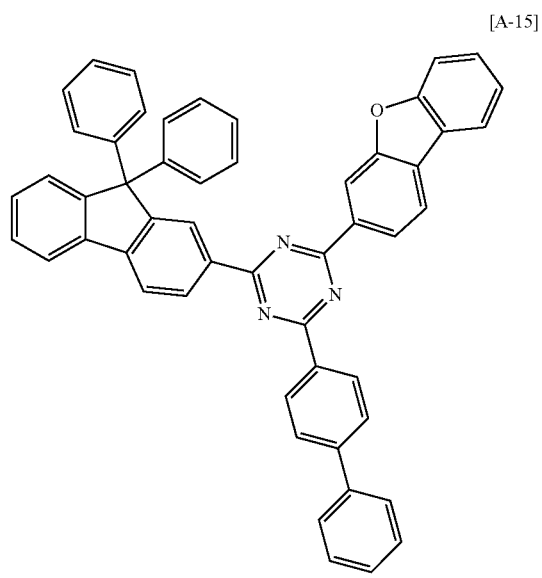
[A-16]
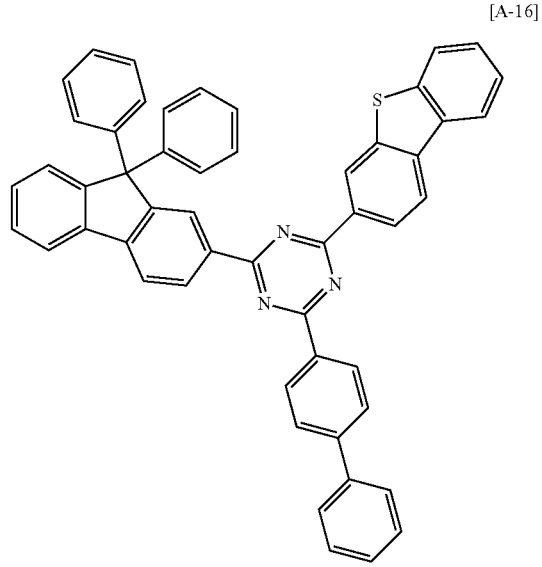

[A-17]
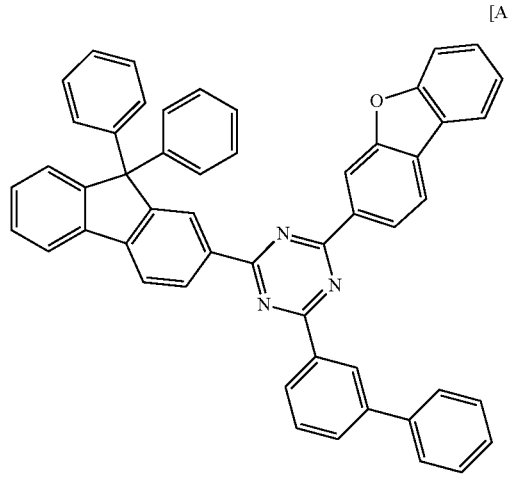
[A-18]
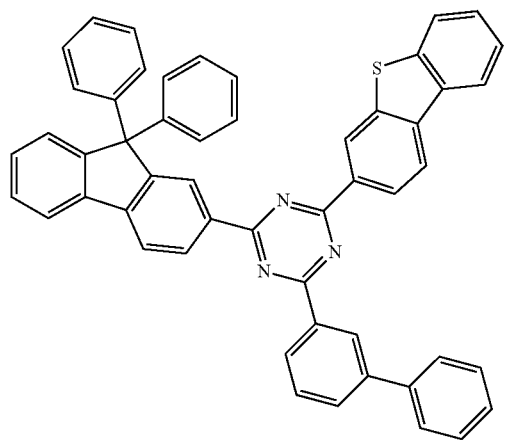
[A-19]
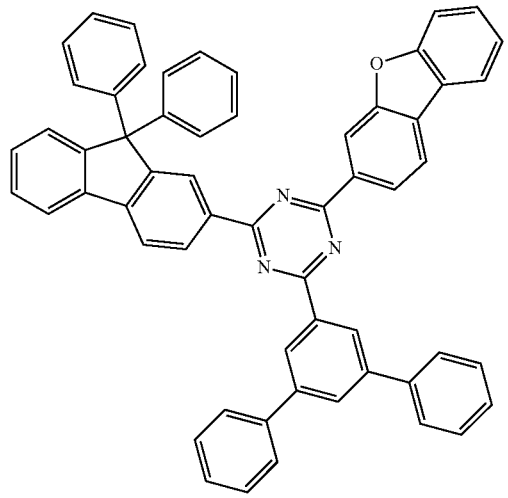
[A-20]
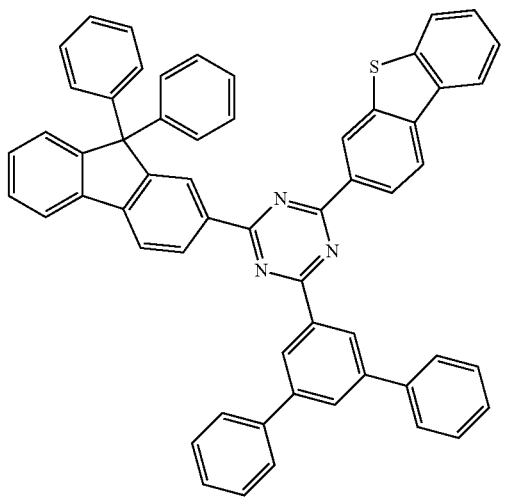
[A-21]
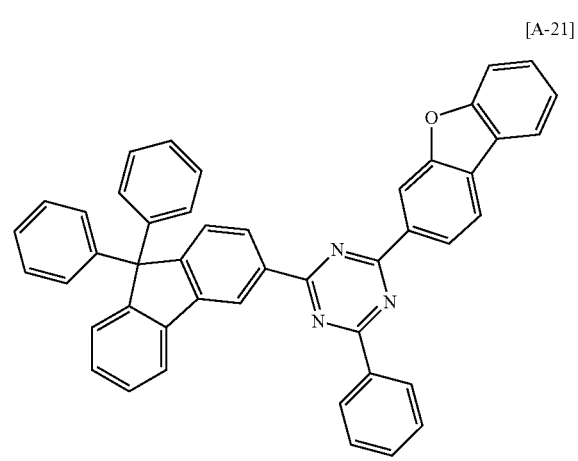
[A-22]
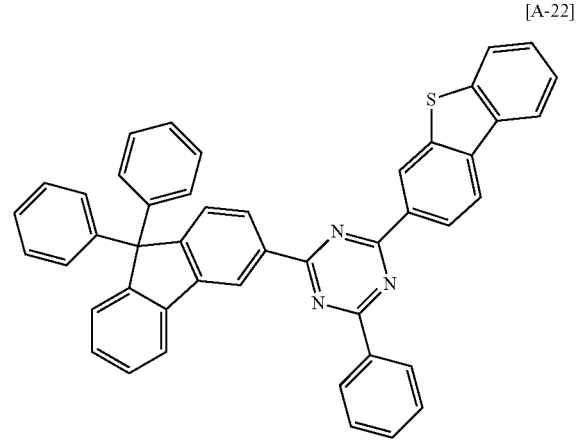

-continued
[A-23]
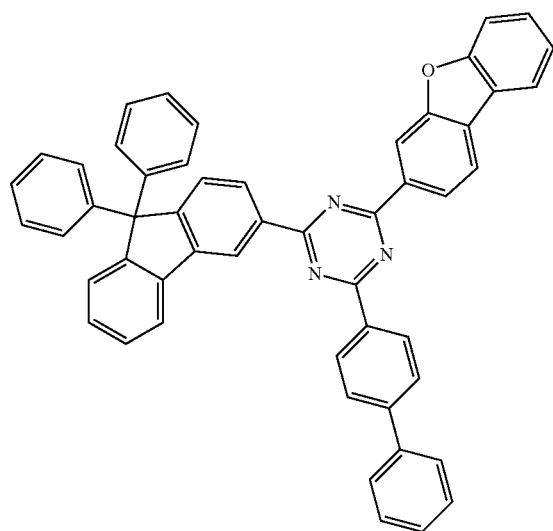
[A-24]
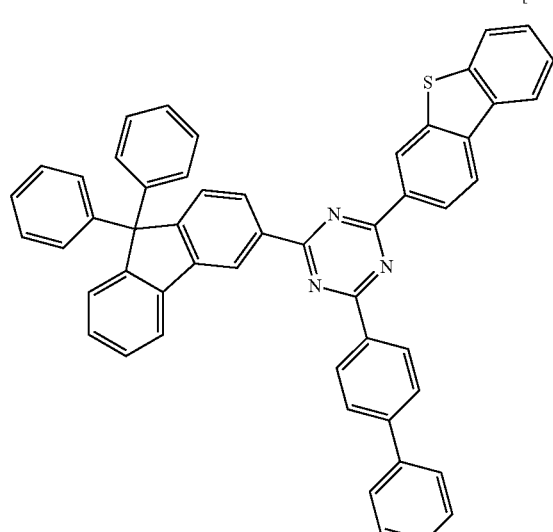
[A-25]
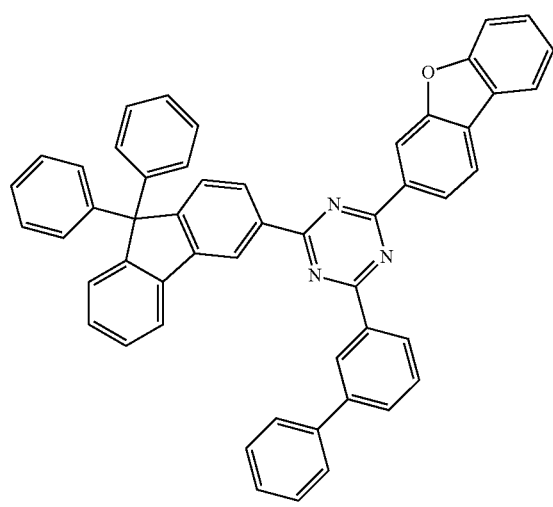
[A-26]
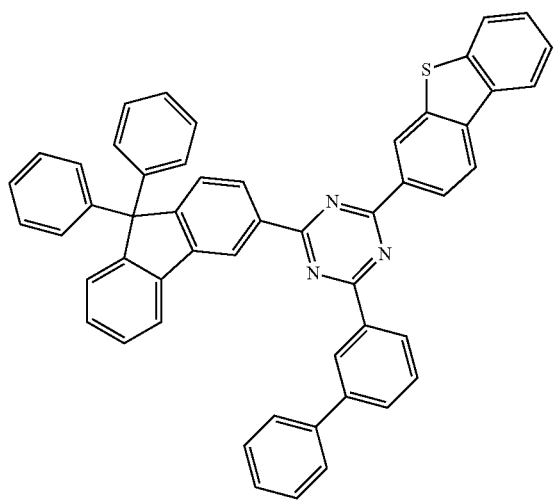
[A-27]
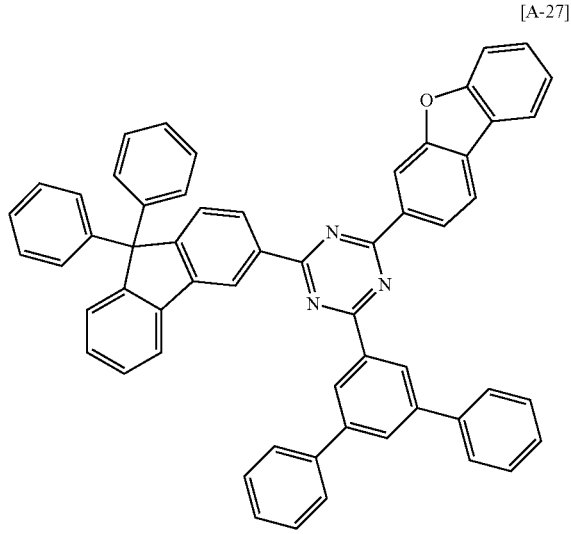
[A-28]
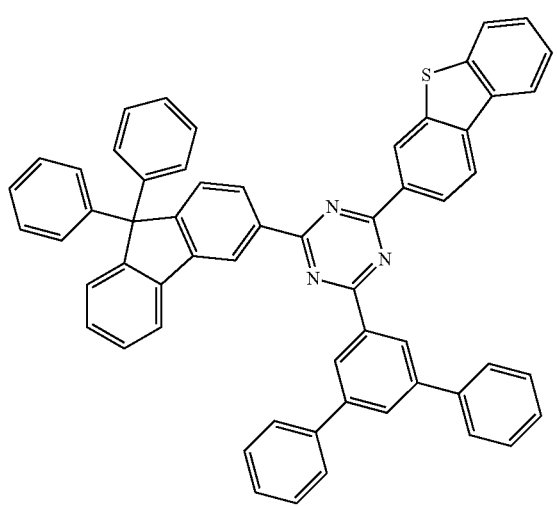

[A-29]

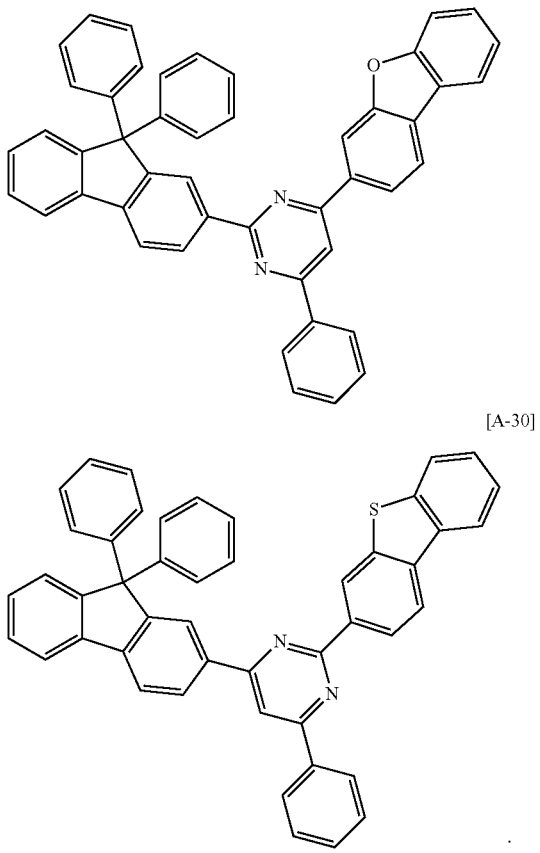

[A-30]

The first compound for an organic optoelectronic device may be applied to an organic optoelectronic device and may be applied to an organic optoelectronic device alone or with another compound for an organic optoelectronic device. When the compound for an organic optoelectronic device is used with another compound for an organic optoelectronic device, they may be applied in a form of a composition.

Hereinafter, a composition for an organic optoelectronic device including the first compound for an organic optoelectronic device is for example described.

A composition for an organic optoelectronic device according to another embodiment of the present invention includes the first compound for an organic optoelectronic device; and the second compound for an organic optoelectronic device including a carbazole moiety represented by Chemical Formula 2.

[Chemical Formula 2]

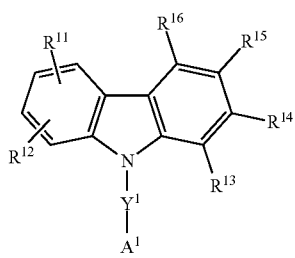

In Chemical Formula 2, $Y^1$ is a single bond, a substituted or unsubstituted C6 to C30 arylene group, or a substituted or unsubstituted C2 to C30 heteroarylene group, $A^1$ is a substituted or unsubstituted C6 to C30 aryl group, or a substituted or unsubstituted C2 to C30 heterocyclic group, $R^{11}$ to $R^{16}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, $R^{13}$ to $R^{16}$ are independently present or adjacent groups of $R^{13}$ to $R^{16}$ are linked with each other to form a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring, wherein the "substituted" refers to replacement of at least one hydrogen by deuterium, a C1 to C4 alkyl group, a C6 to C18 aryl group, or a C2 to C30 heteroaryl group. In a specific example embodiment of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

In an example embodiment of the present invention, Chemical Formula 2 may be selected from Chemical Formula 2A, or a combination of Chemical Formula 2B-1 and Chemical Formula 2B-2:

[Chemical Formula 2A]

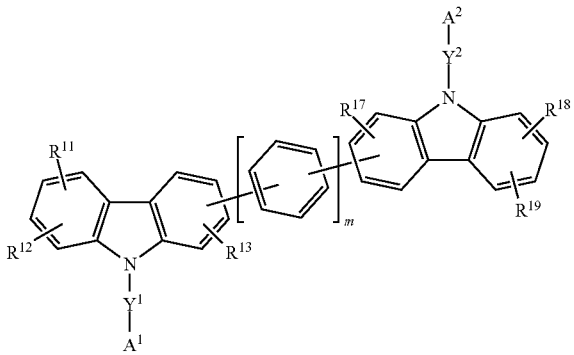

[Chemical Formula 2B-1]

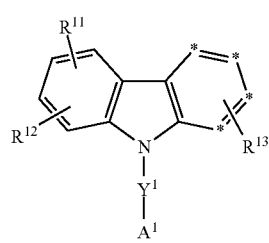

[Chemical Formula 2B-2]

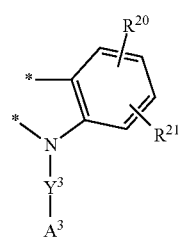

In Chemical Formula 2A, Chemical Formula 2B-1, and Chemical Formula 2B-2, $Y^1$ to $Y^3$ are independently a single bond, a substituted or unsubstituted C6 to C30 arylene group, a substituted or unsubstituted C2 to C30 heteroarylene group, or a combination thereof, $A^1$ to $A^3$ are independently substituted or unsubstituted C6 to C30 aryl group, a substituted or unsubstituted C2 to C30 heterocyclic group, or a combination thereof, $R^{11}$ to $R^{13}$ and $R^{17}$ to $R^{21}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is one of integers of 0 to 2. More preferably, m=0.

In an example embodiment of the present invention, Chemical Formula 2 may be represented by Chemical Formula 2A or Chemical Formula 2C.

[Chemical Formula 2A]

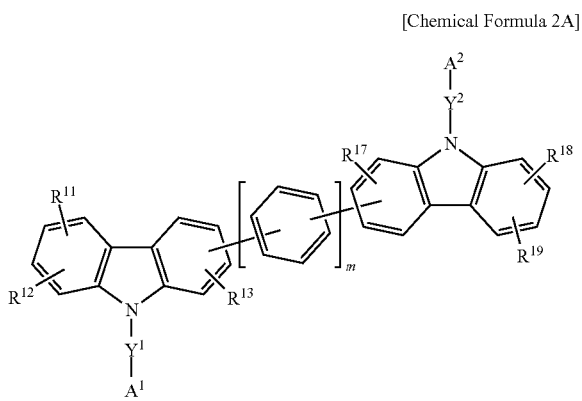

[Chemical Formula 2C]

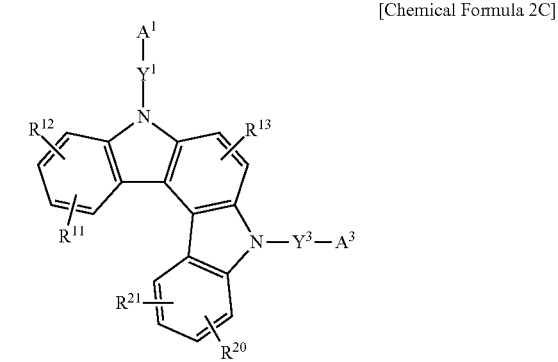

In Chemical Formula 2A and Chemical Formula 2C, $Y^2$ and $Y^3$ are the same as $Y^1$, $A^2$ and $A^3$ are the same as $A^1$, $R^{17}$ to $R^{21}$ are the same as $R^{11}$ to $R^{16}$, and m is one of integers of 0 to 2.

In a specific example embodiment of the present invention, $Y^1$ to $Y^3$ of Chemical Formula 2A, Chemical Formula 2B-1, Chemical Formula 2B-2, and Chemical Formula 2C may independently be a single bond, or a substituted or unsubstituted C6 to C18 arylene group. Specifically, $Y^1$ to $Y^3$ may be a single bond, a meta-phenylene group, or a para-phenylene group.

In a specific example embodiment of the present invention, $A^1$ to $A^3$ of Chemical Formula 2A, Chemical Formula 2B-1, Chemical Formula 2B-2 and Chemical Formula 2C may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof. Specifically, $A^1$ to $A^3$ may be a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzothiophenyl group, or a substituted or unsubstituted dibenzofuranyl group.

In an example embodiment of the present invention, $R^{11}$ to $R^{13}$ and $R^{17}$ to $R^{21}$ of Chemical Formula 2A, Chemical Formula 2B-1, Chemical Formula 2B-2, Chemical Formula 2C may independently be hydrogen, deuterium, or a substituted or unsubstituted C6 to C12 aryl group. Specifically, $R^{11}$ to $R^{13}$ and $R^{17}$ to $R^{21}$ may be hydrogen or a phenyl group.

In a specific example embodiment of the present invention, m of Chemical Formula 2A may be 0 or 1, and preferably m=0.

In addition, when m=0 in Chemical Formula 2A, a bonding position of carbazoles may be a 2,3-bond, a 3,3-bond, or a 2,2-bond, and specifically, a 3,3-bond in a core of biscarbazole.

In a more specific example embodiment of the present invention, Chemical Formula 2A may have one of structures of Group 1 and *—$Y^1$-$A^1$ and *—$Y^2$-$A^2$ may have one of substituents of Group II.

[Group I]

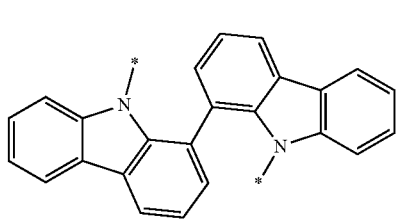

C-1

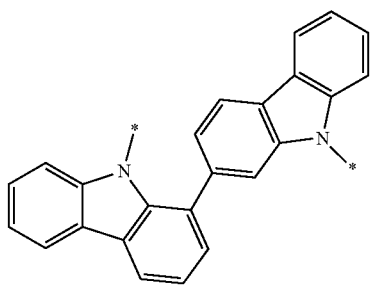

C-2

C-3
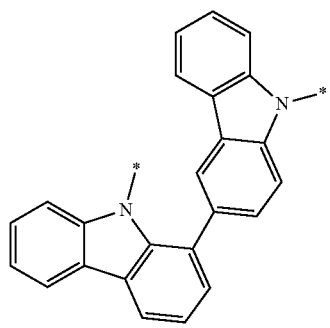
C-4
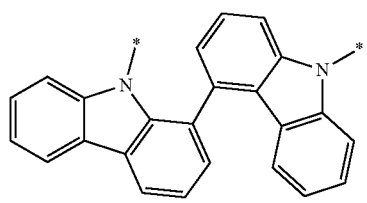
C-5
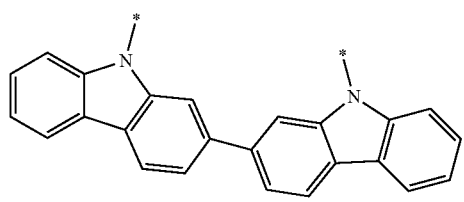
C-6
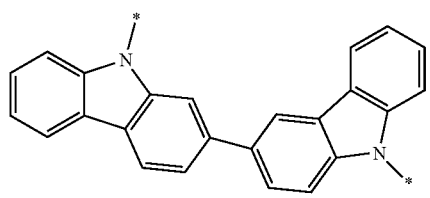
C-7
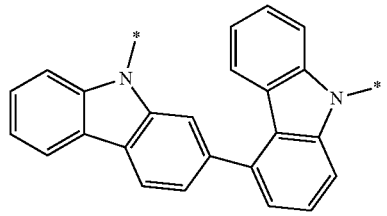
C-8
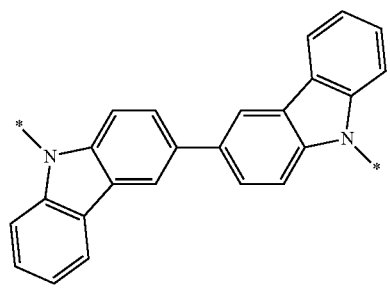
C-9
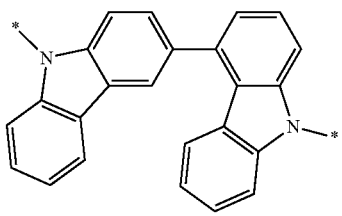
C-10
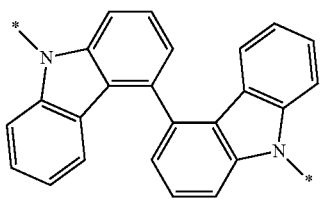
C-11
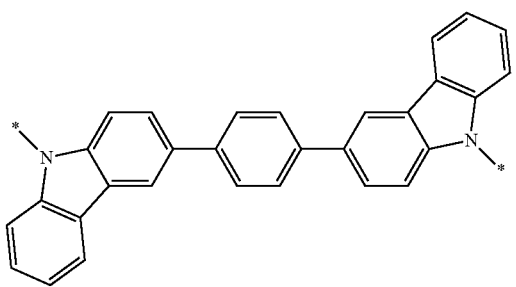
C-12
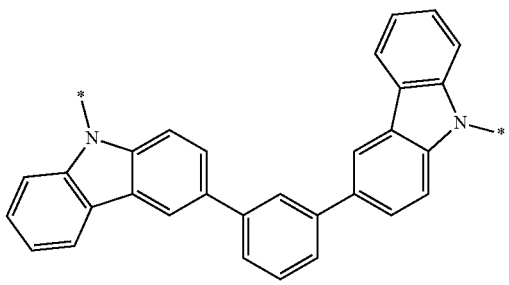
C-13
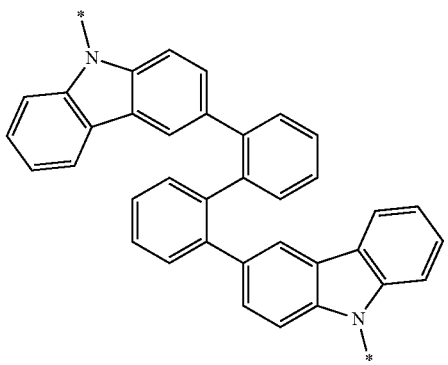

C-14
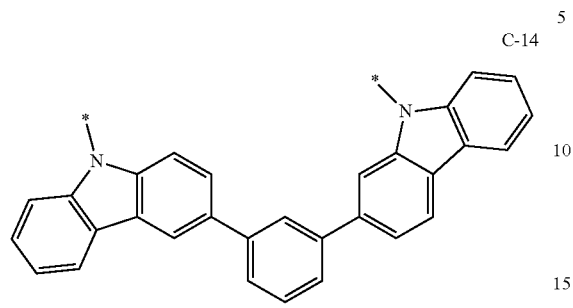
C-15
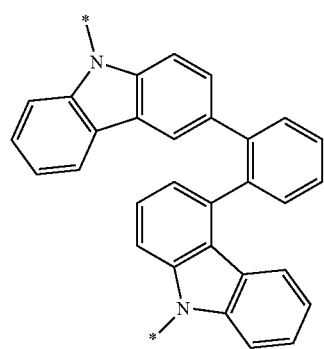
C-16
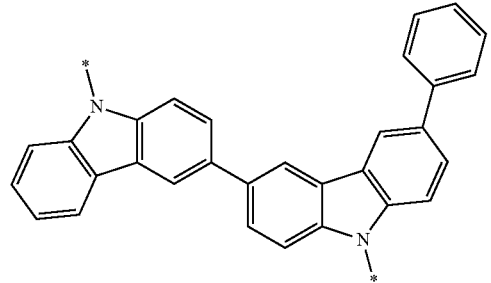
C-17
C-18
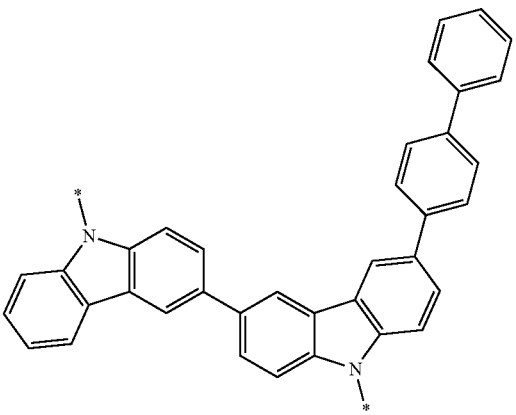
[Group II]
B-1
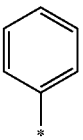
B-2
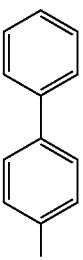
B-3
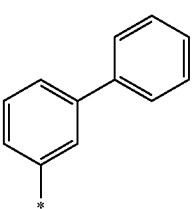
B-4
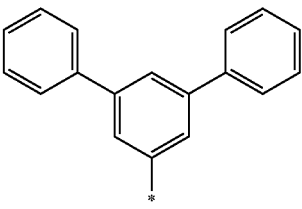
B-5
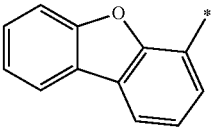
B-6
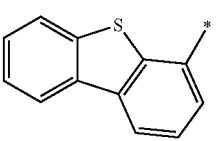

B-7 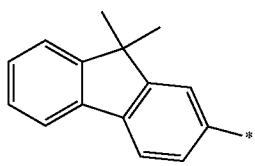
B-8 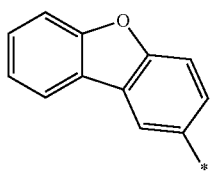
B-9 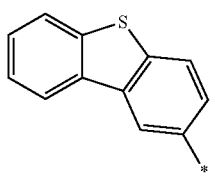
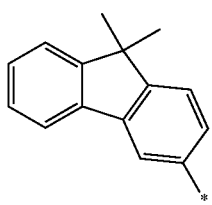
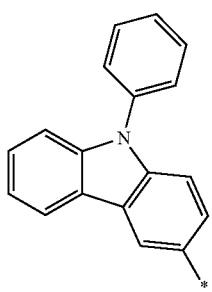
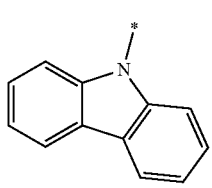
B-13 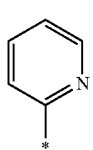
B-14 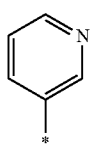
B-15 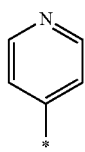
B-16 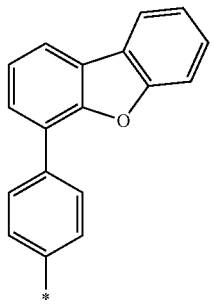
B-17 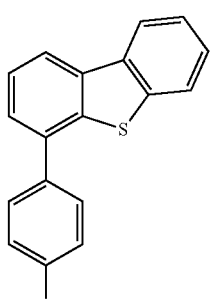
B-18 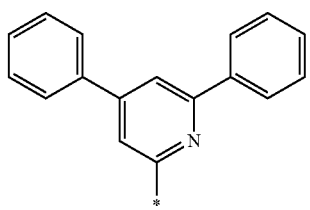
B-19 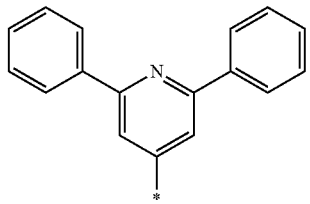
B-20 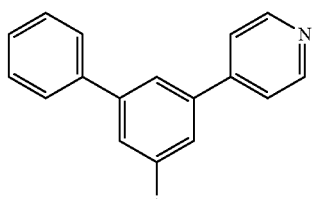
B-21 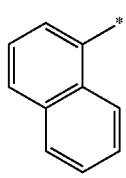

-continued
B-22 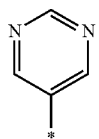
B-23 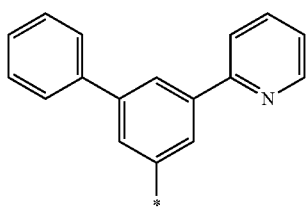
B-24 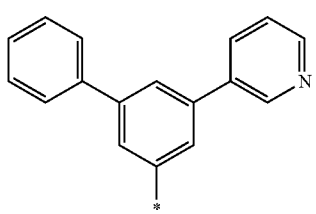
B-25 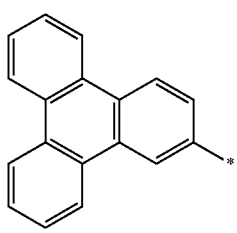
B-26 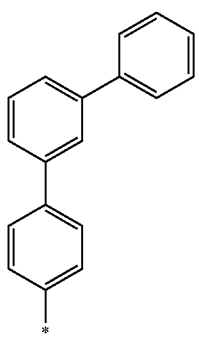
B-27 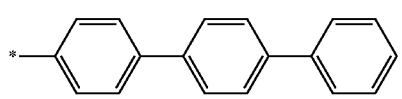
B-28 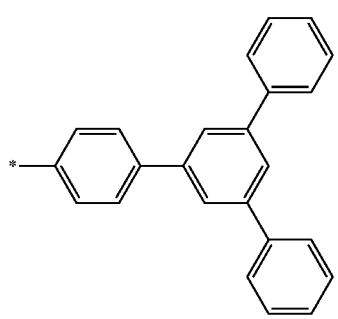
In Groups I and II, * is a linking point.
The second compound for an organic optoelectronic device represented by Chemical Formula 2 may be for example selected from compounds of Group 2.
[Group 2]
[E-1]
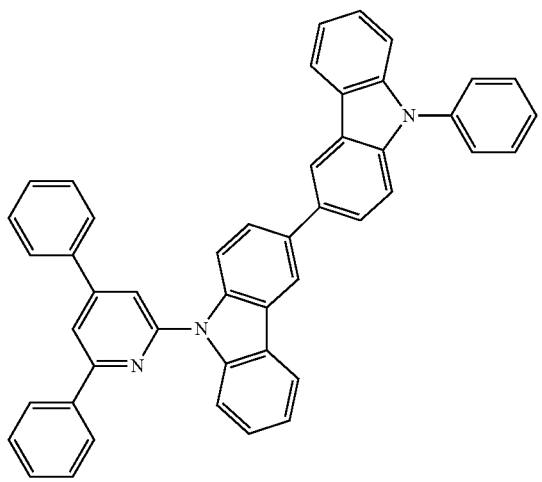
[E-2]
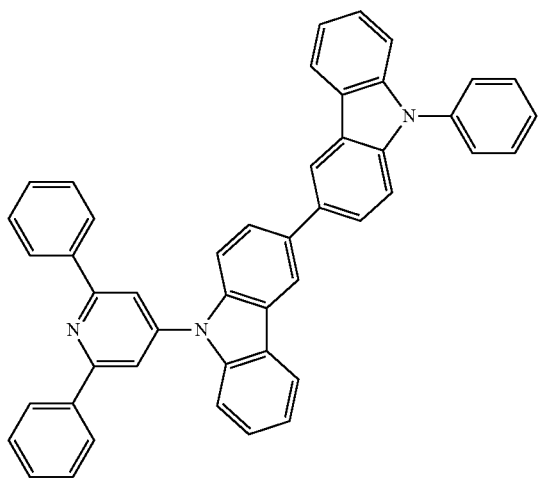
[E-3]
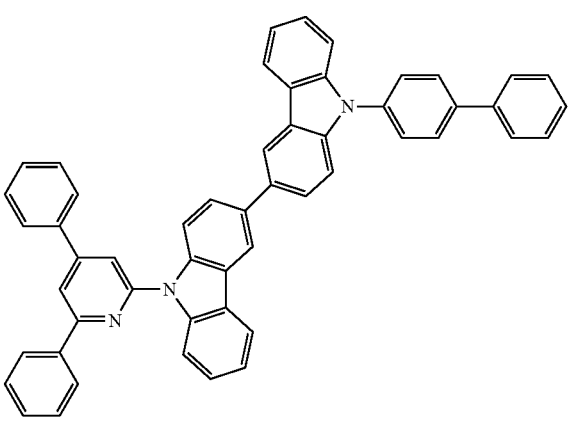

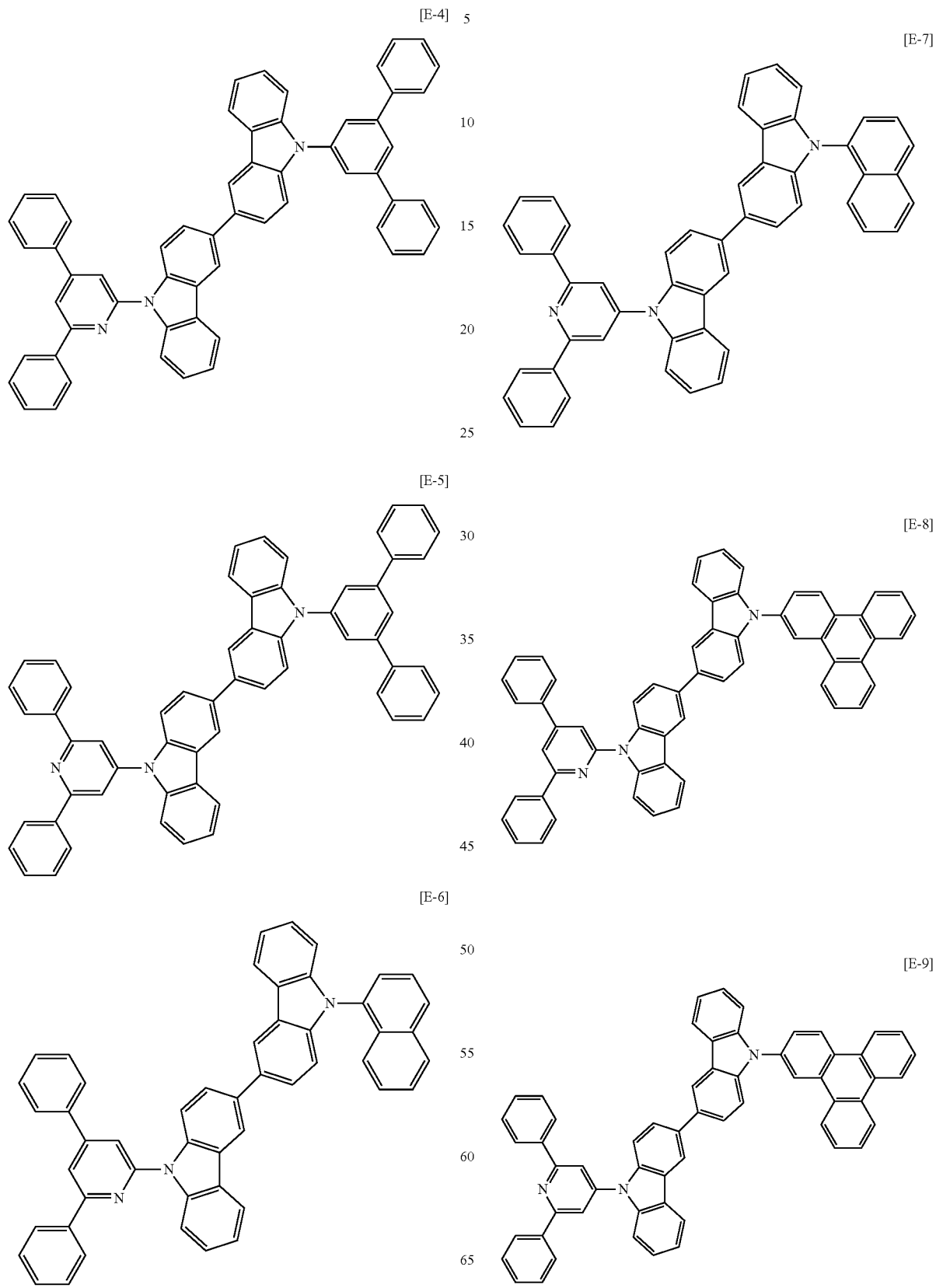

[E-10]
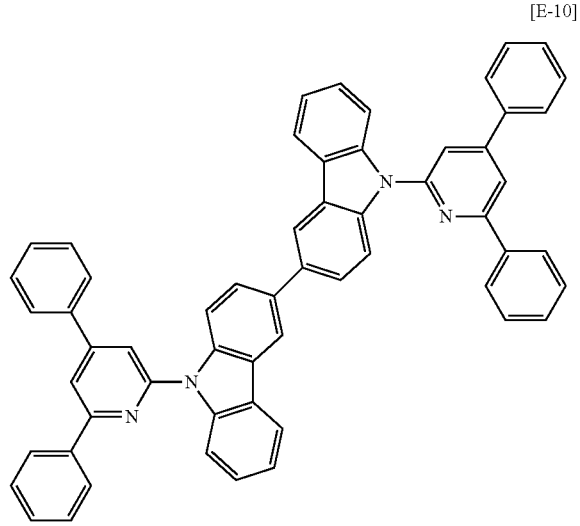
[E-11]
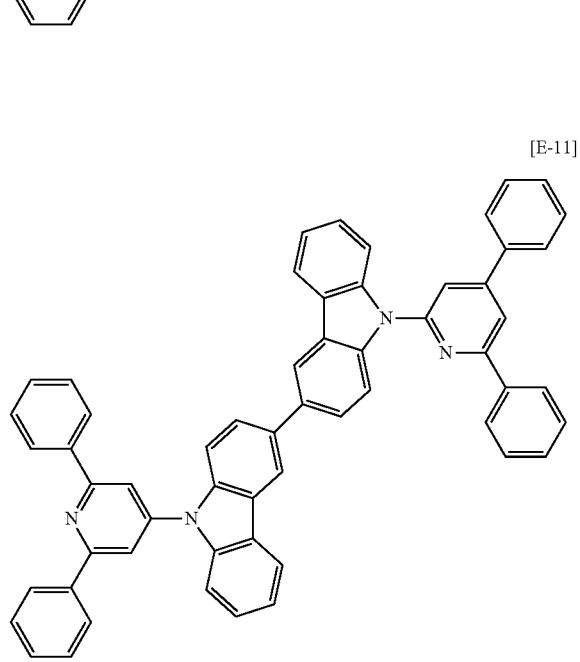
[E-12]
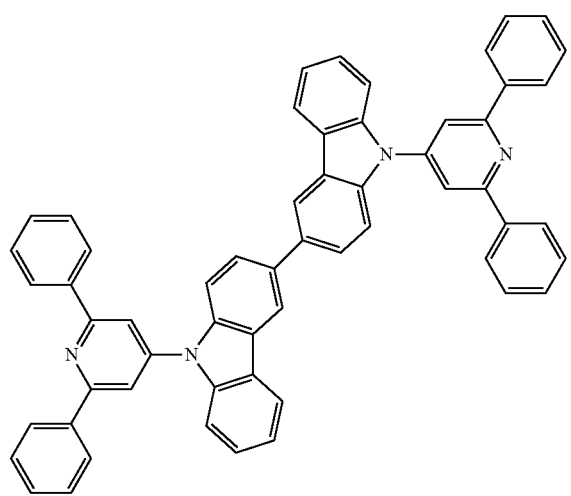
[E-13]
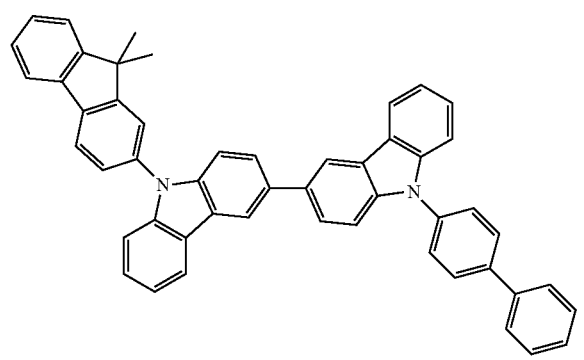
[E-14]
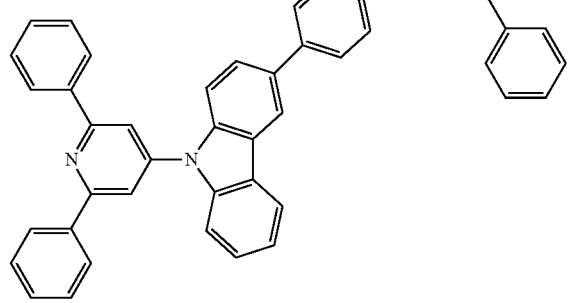
[E-15]
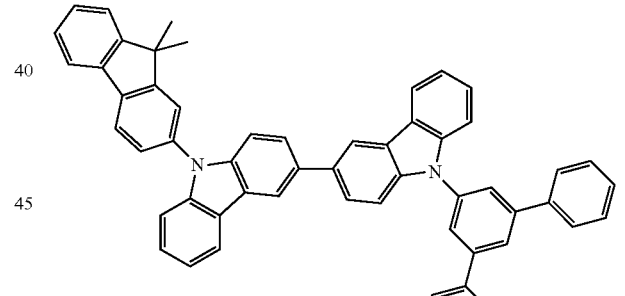
[E-16]
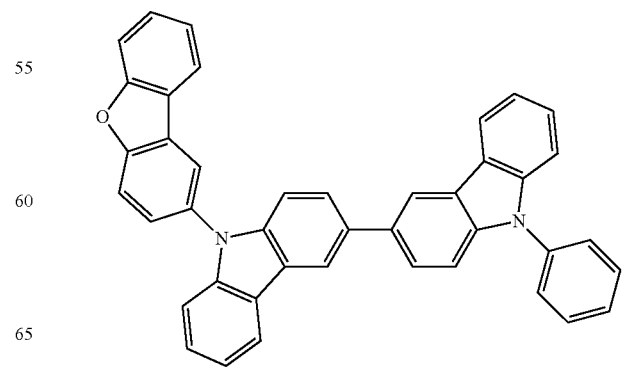

[E-17]
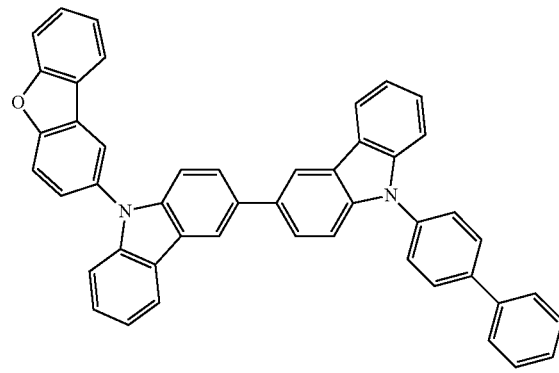
[E-18]
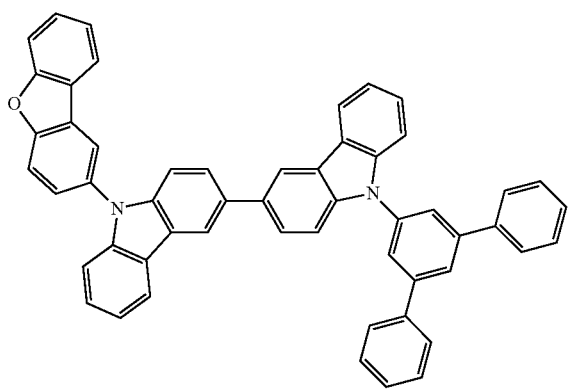
[E-19]
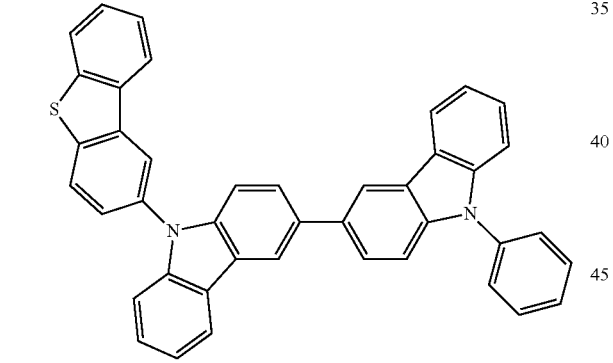
[E-20]
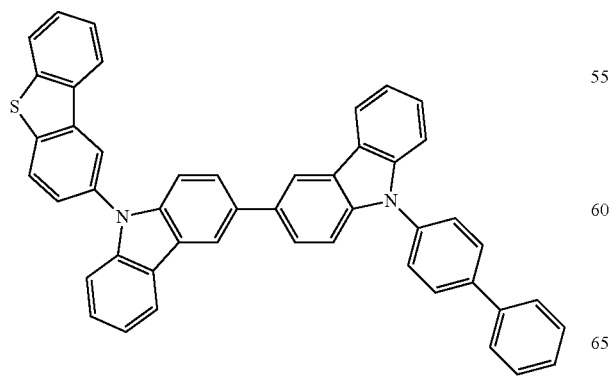
[E-21]
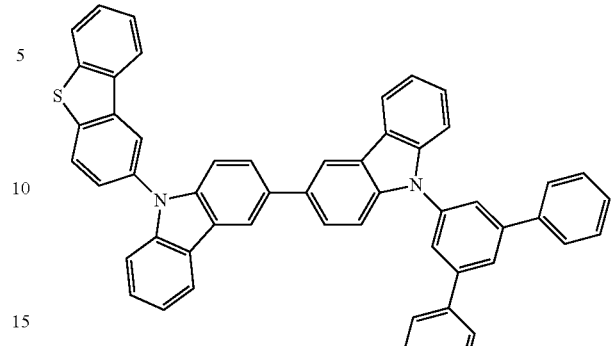
[E-22]
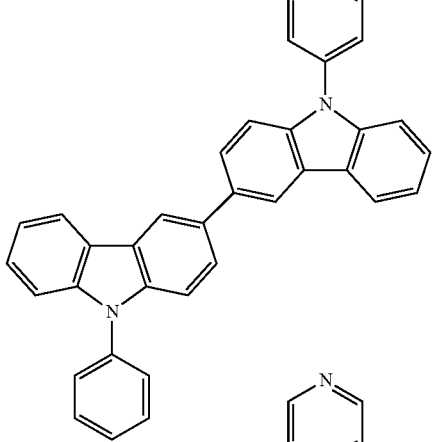
[E-23]
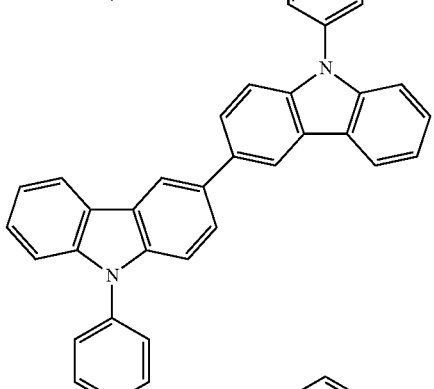
[E-24]

-continued
[E-25]
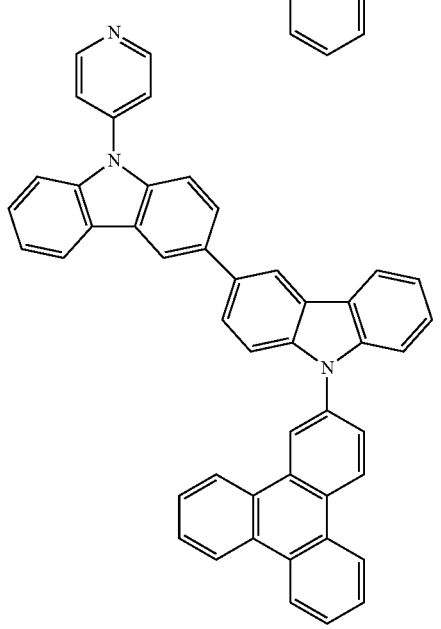
[E-26]
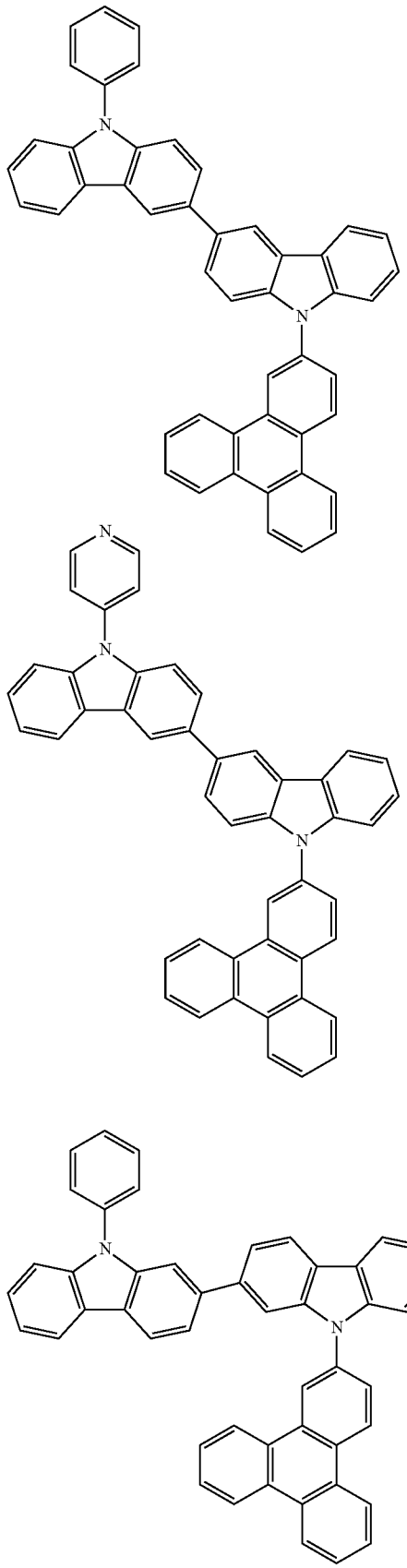
[E-27]
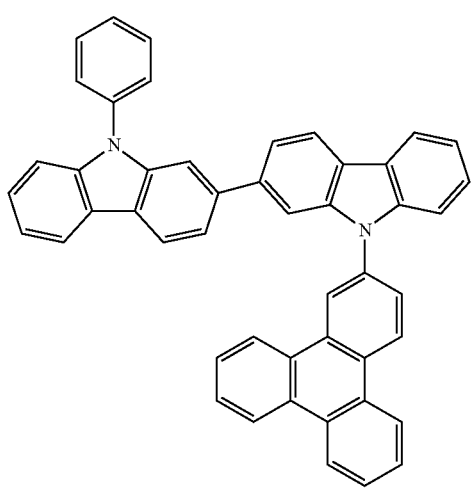
-continued
[E-28]
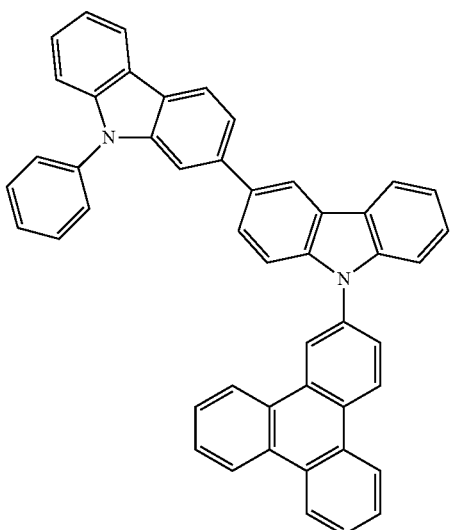
[E-29]
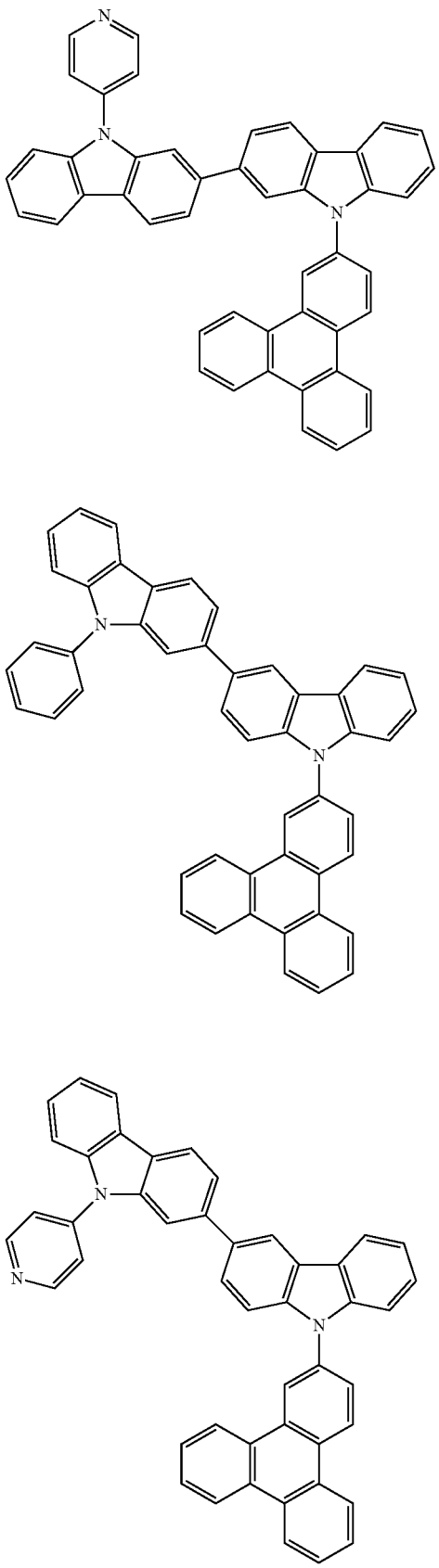
[E-30]
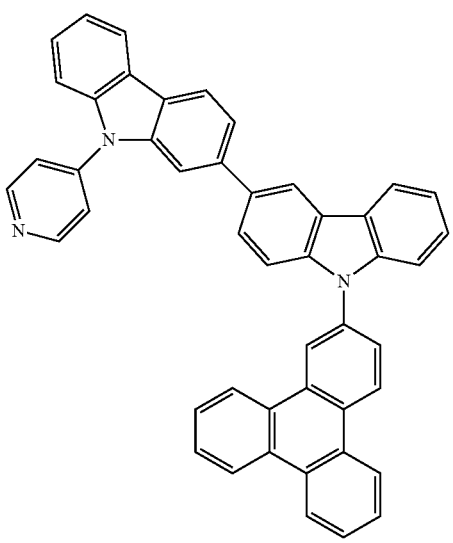

[E-31]
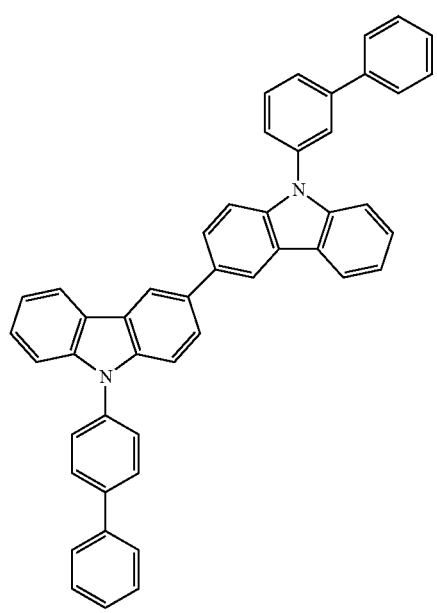
[E-32]
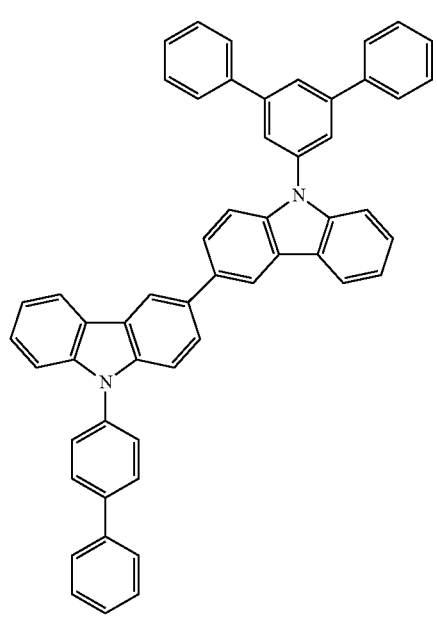
[E-33]
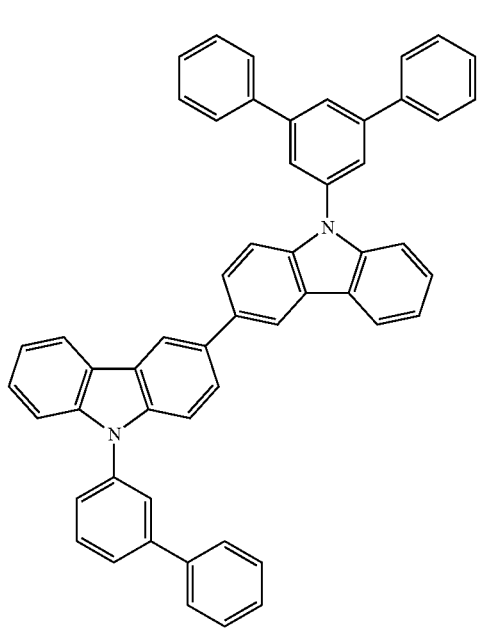
[E-34]
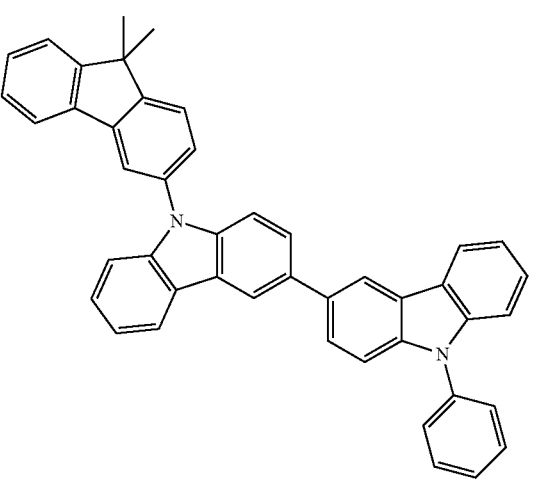

[E-35]
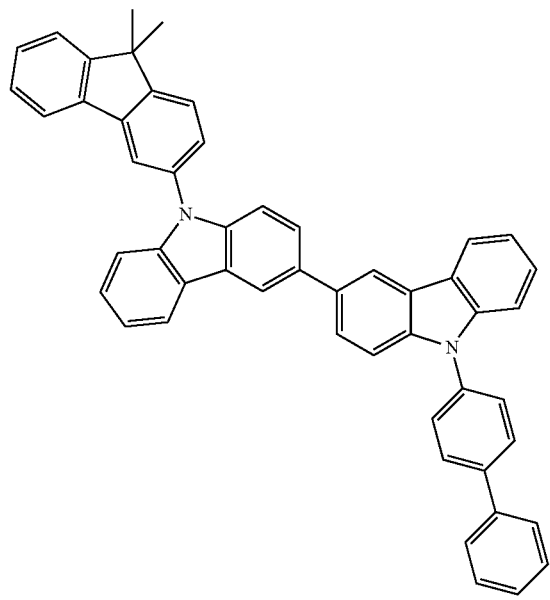
[E-38]
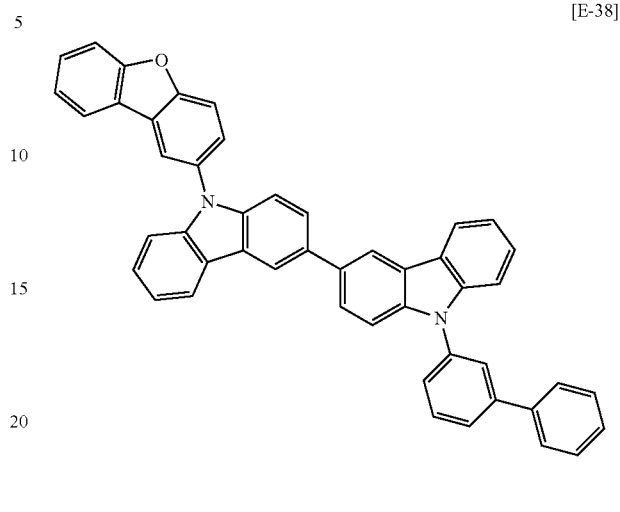
[E-36]
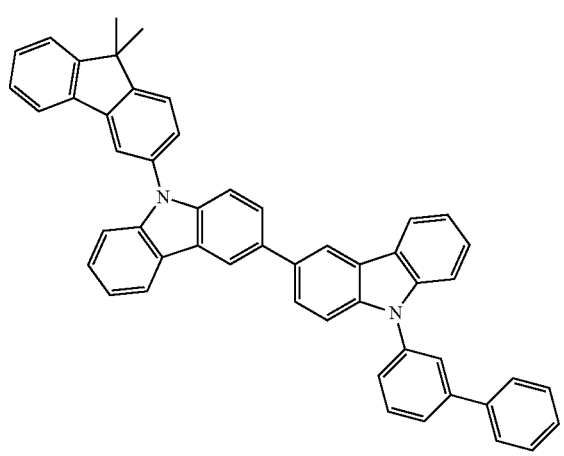
[E-39]
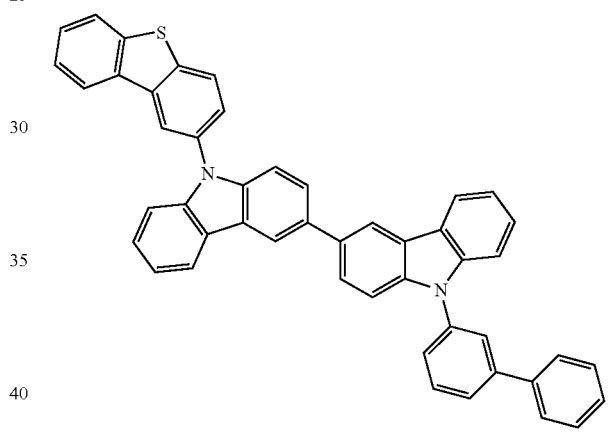
[E-37]
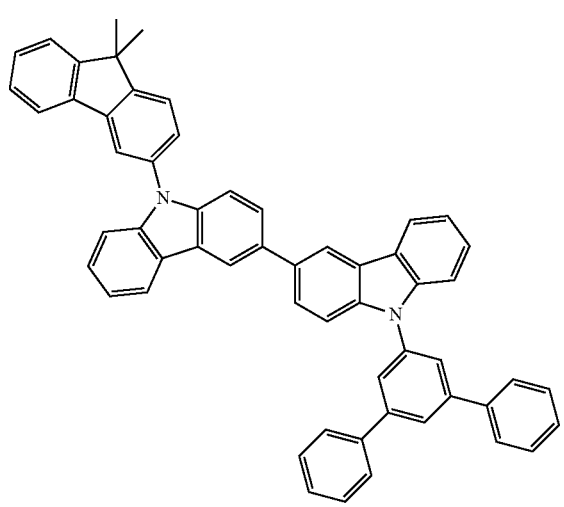
[E-40]
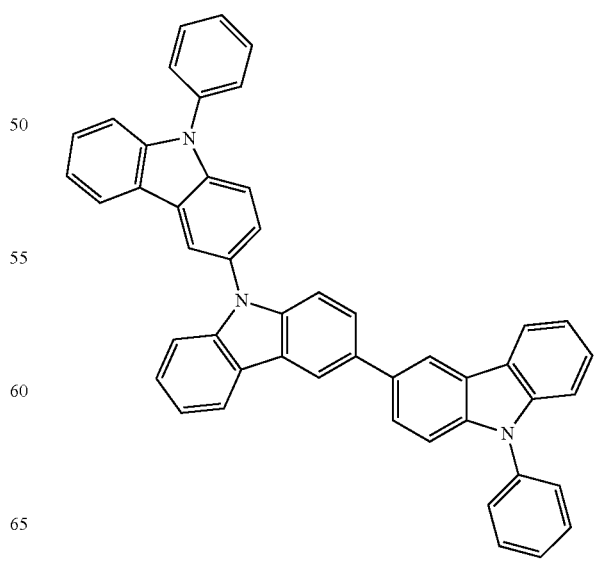

[E-41]
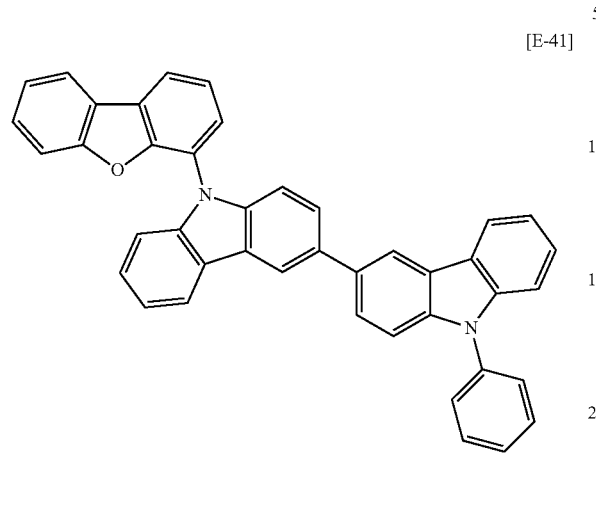
[E-44]
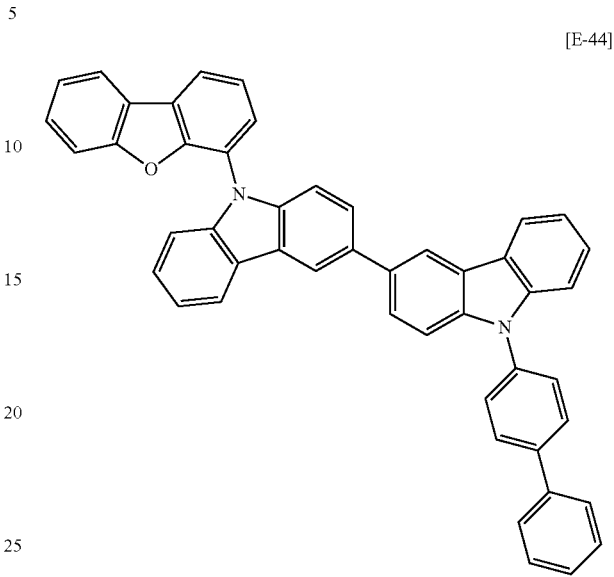
[E-42]
[E-45]
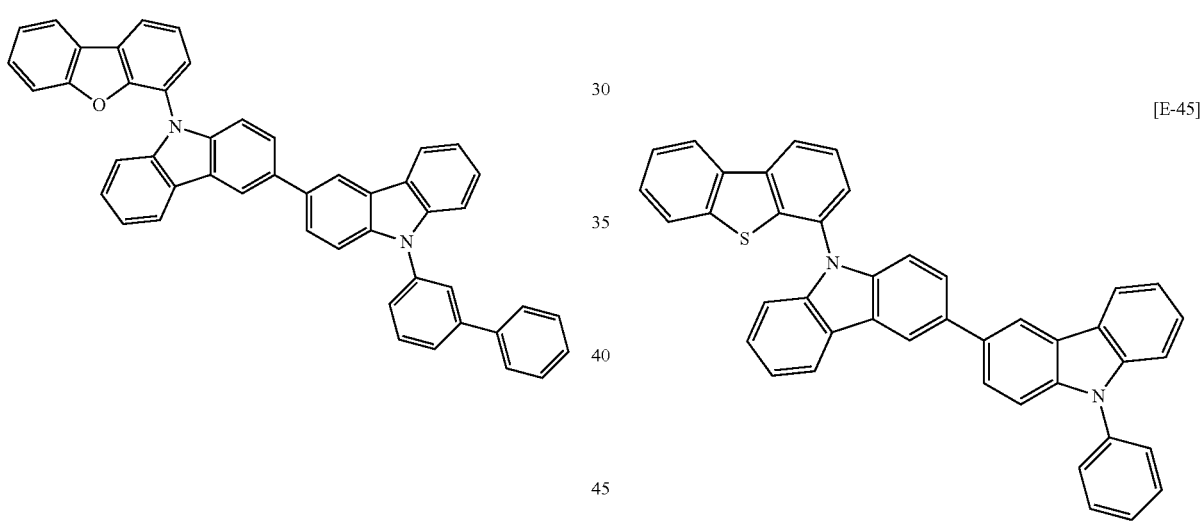
[E-43]
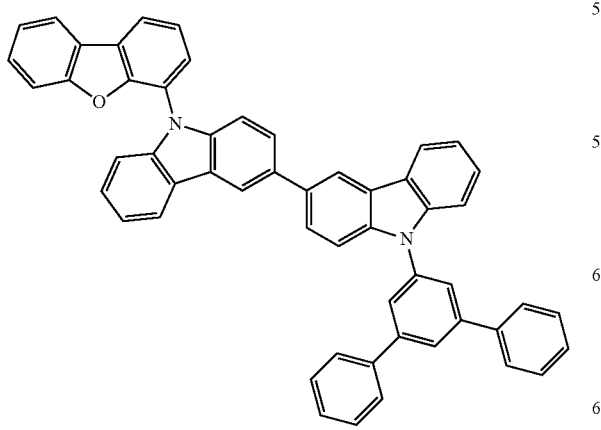
[E-46]
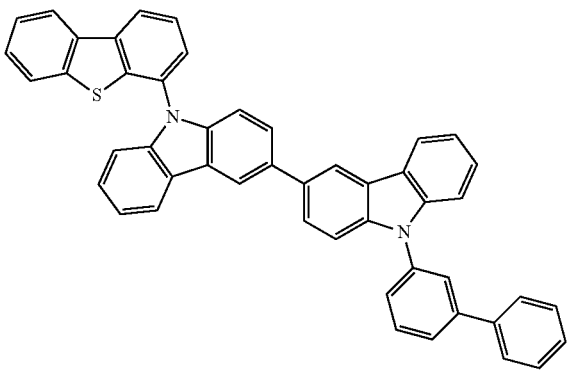

[E-47]
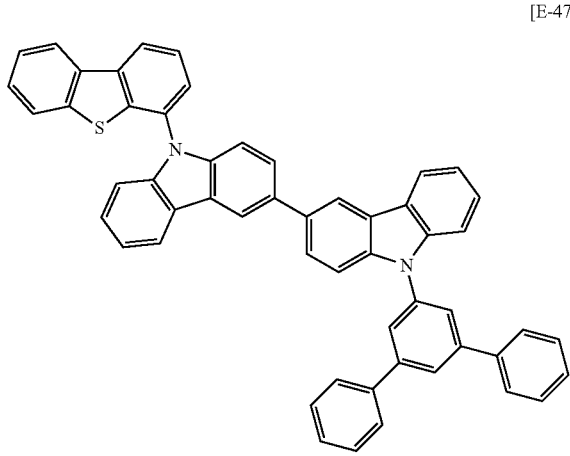
[E-48]
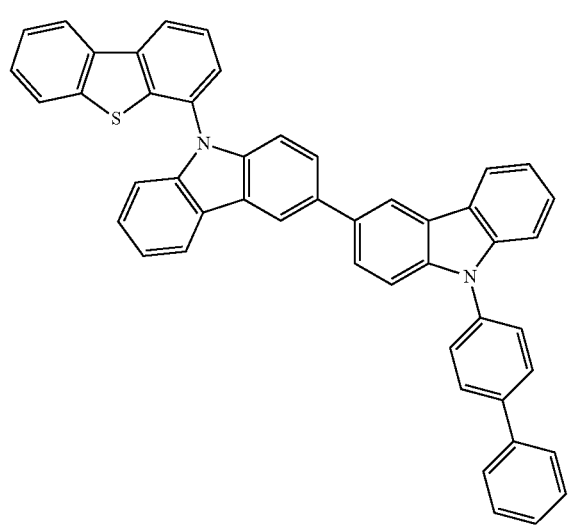
[E-49]
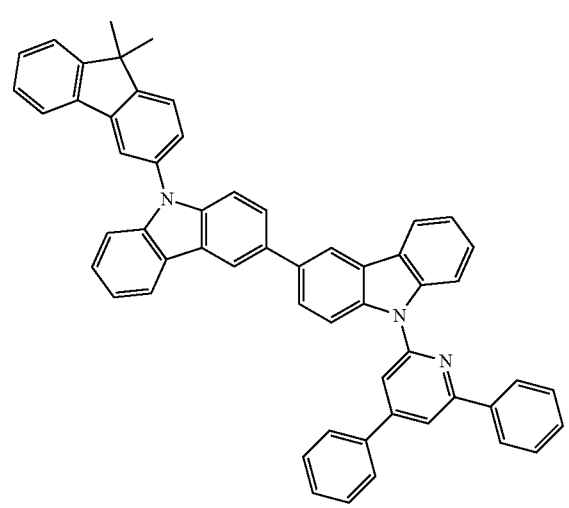
[E-50]
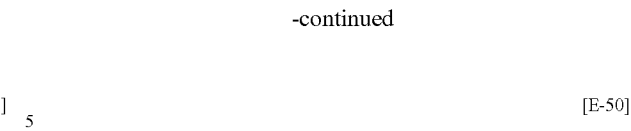
[E-51]
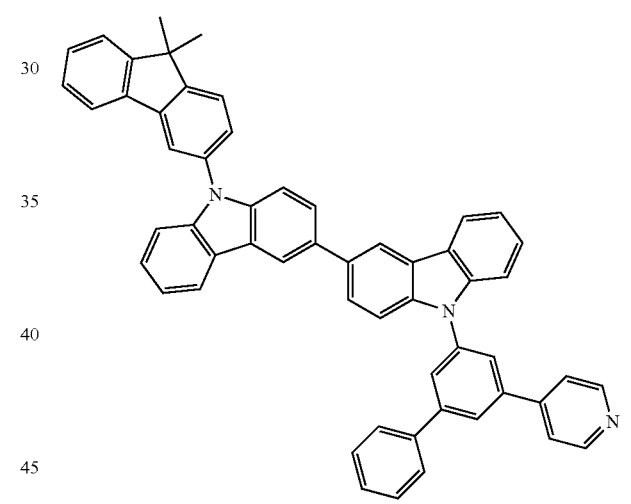
[E-52]
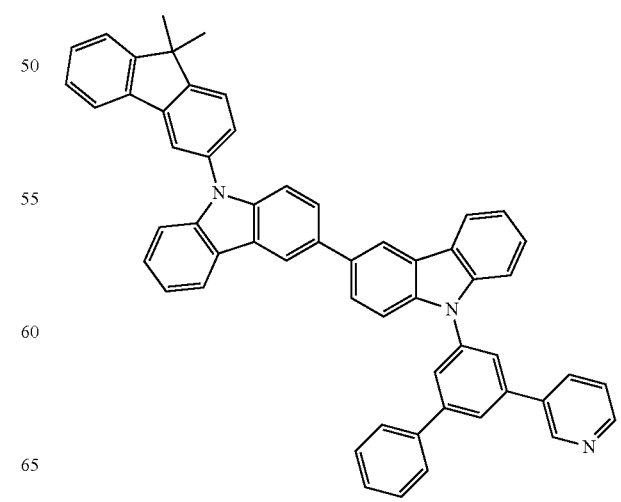

[E-53]
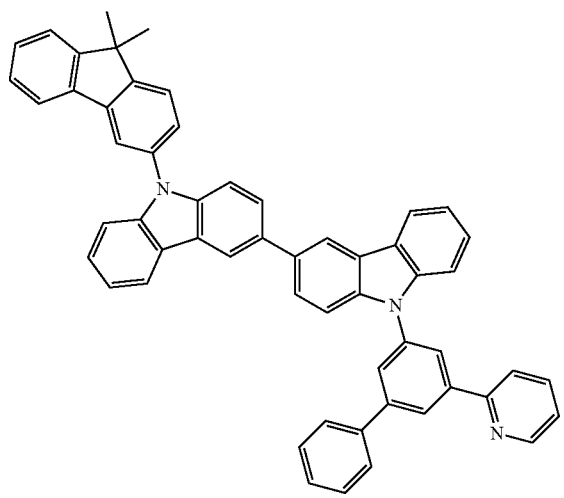
[E-56]
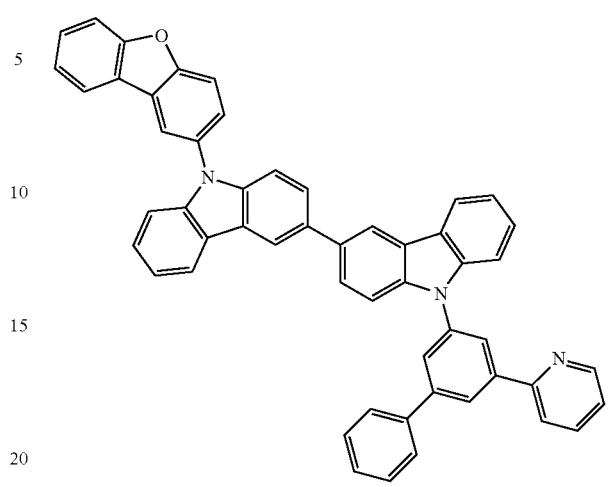
[E-54]
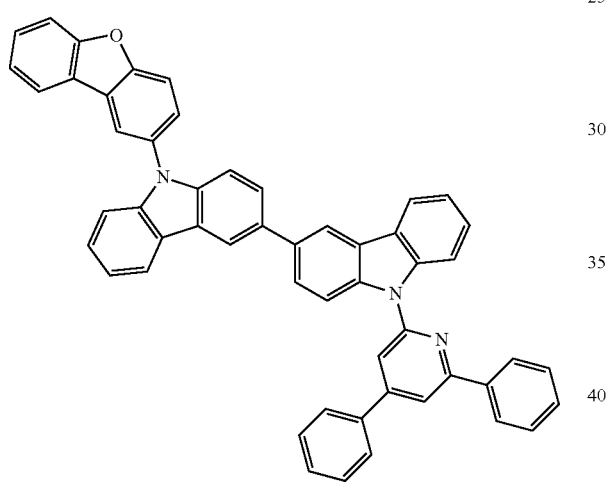
[E-57]
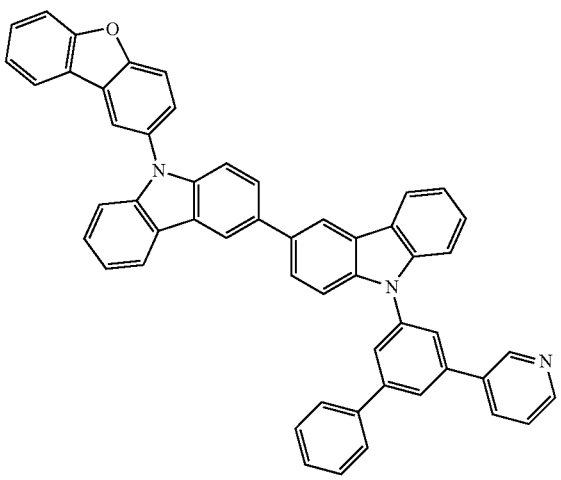
[E-55]
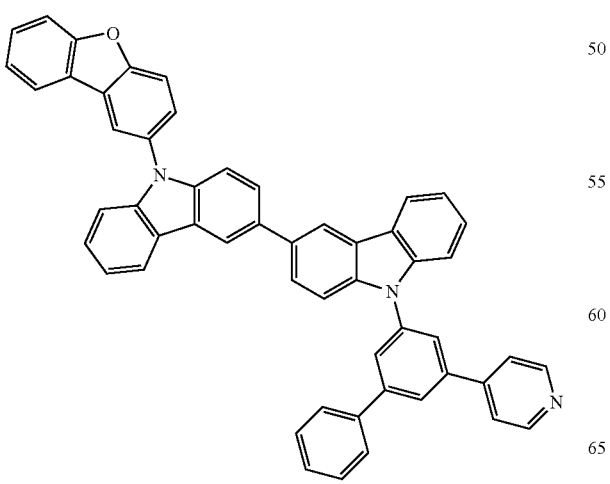
[E-58]
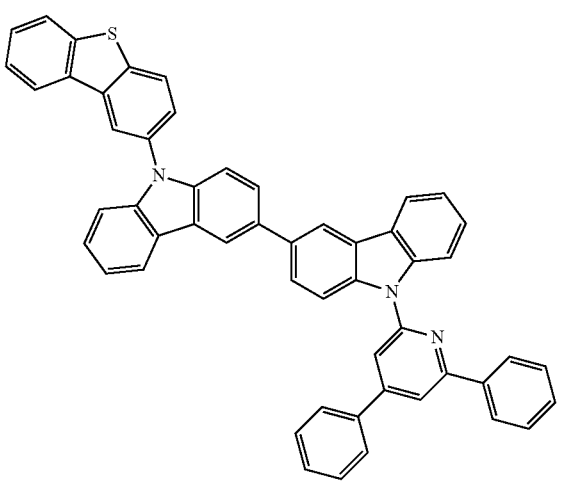

[E-59]
[E-60]
[E-61]
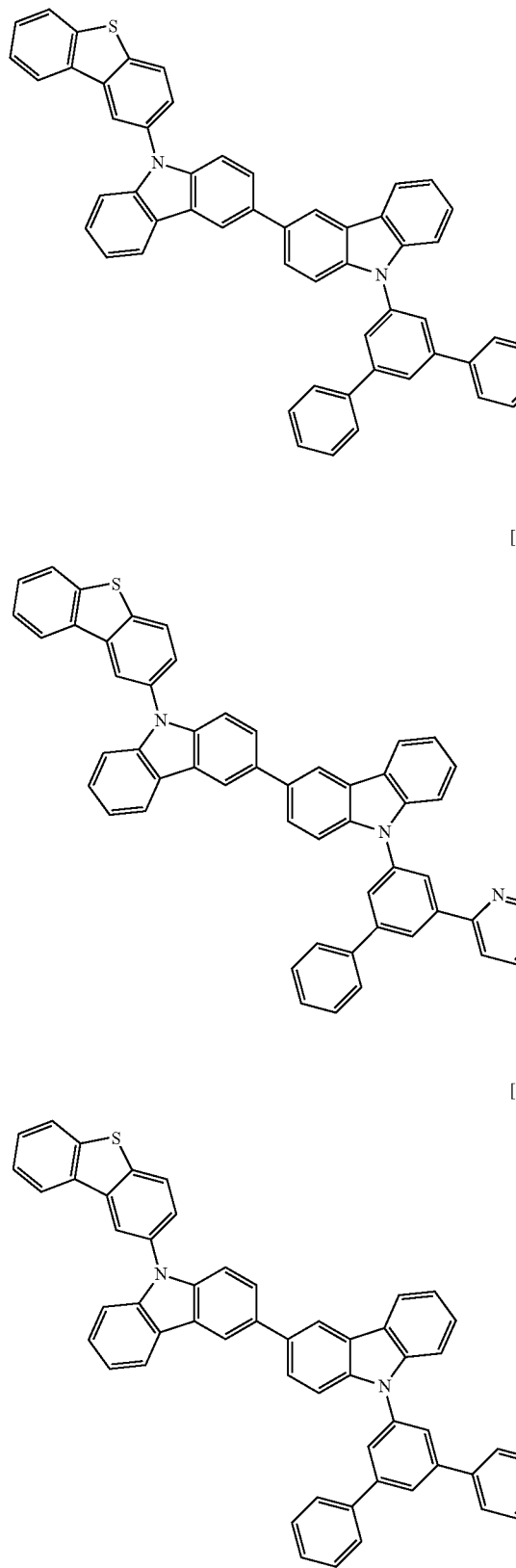
[E-62]
[E-63]
[E-64]
[E-65]
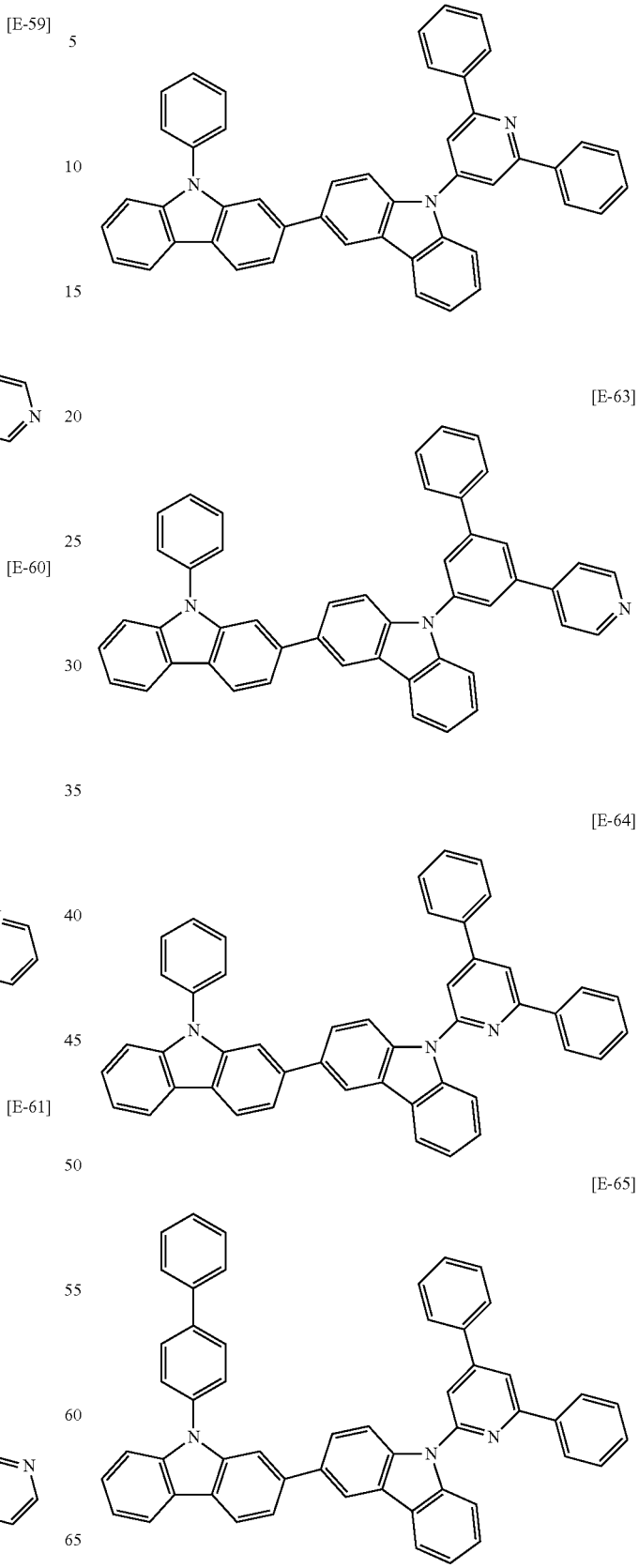

[E-66]
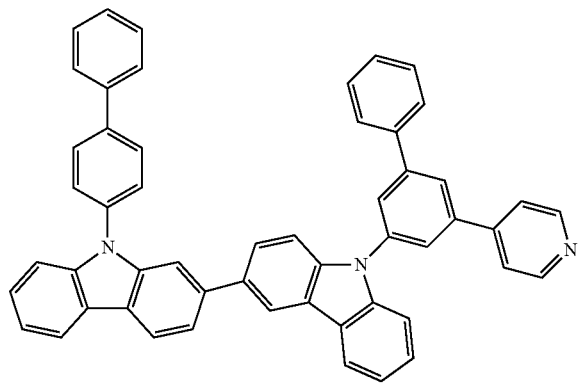
[E-70]
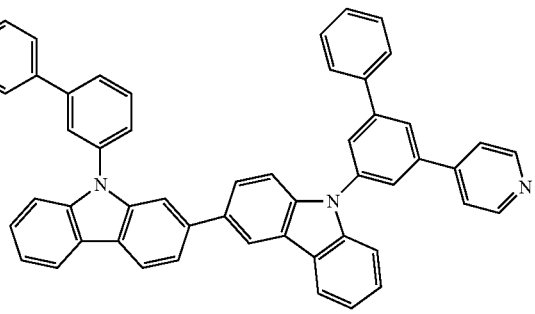
[E-67]
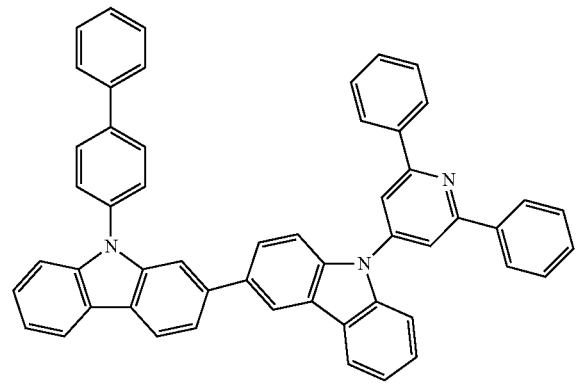
[E-71]
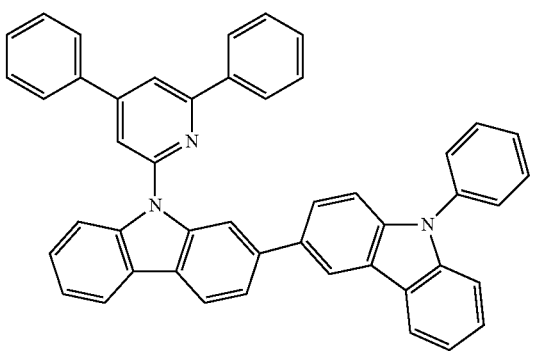
[E-68]
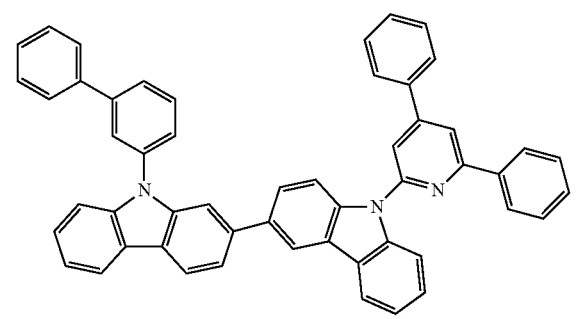
[E-72]
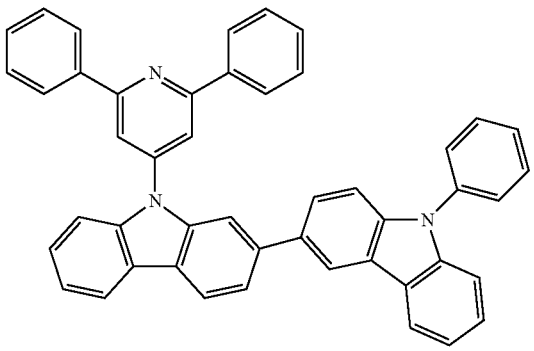
[E-69]
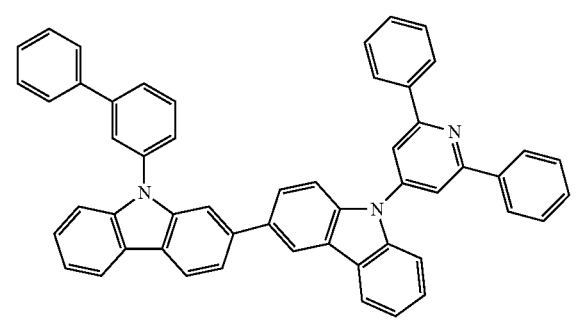
[E-73]
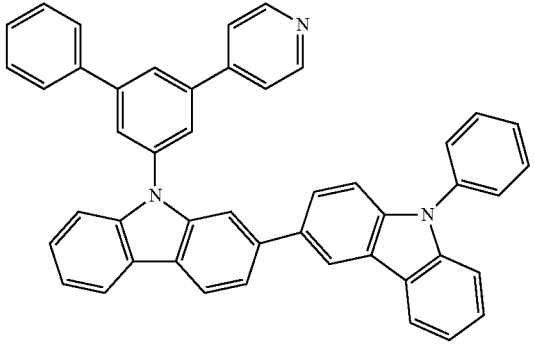

[E-74]
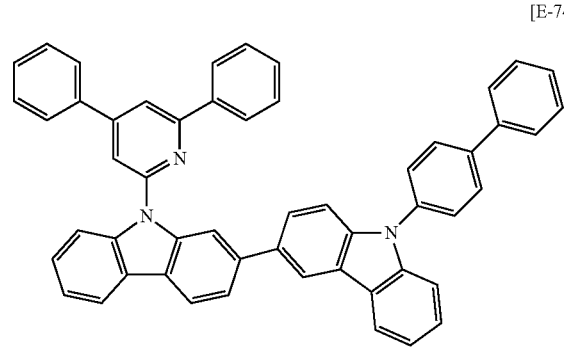
[E-75]
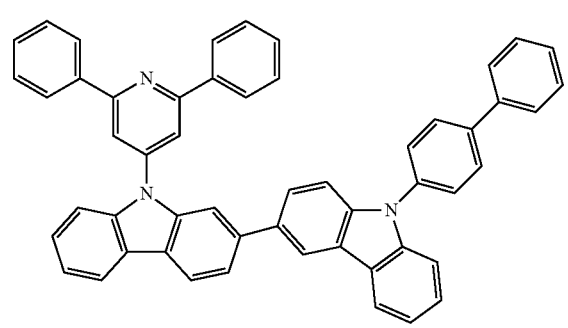
[E-76]
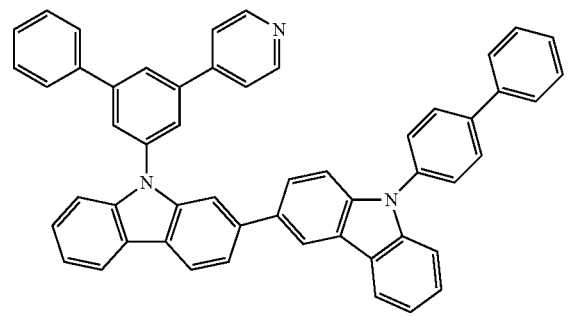
[E-77]
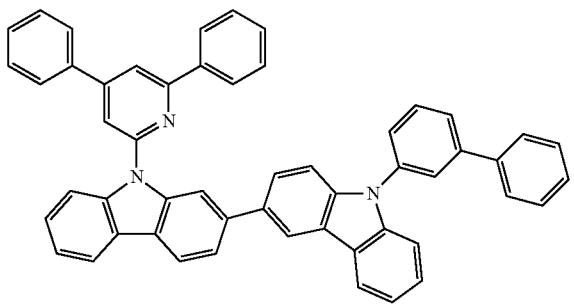
[E-78]
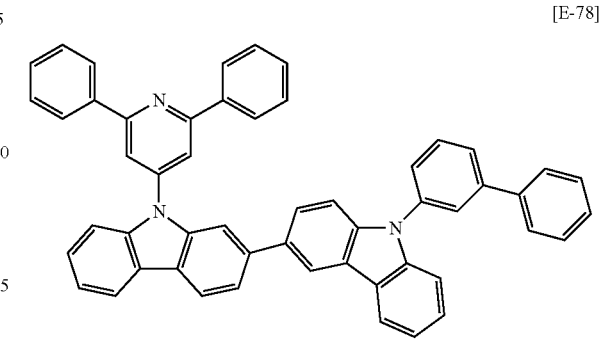
[E-79]
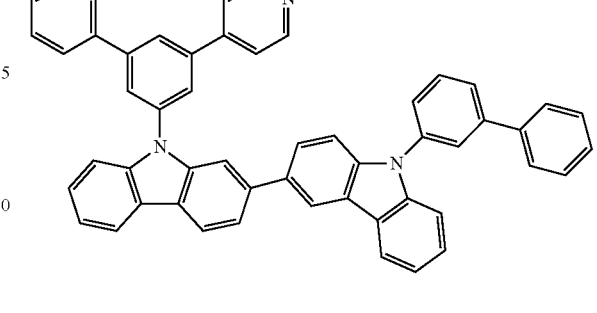
[E-80]
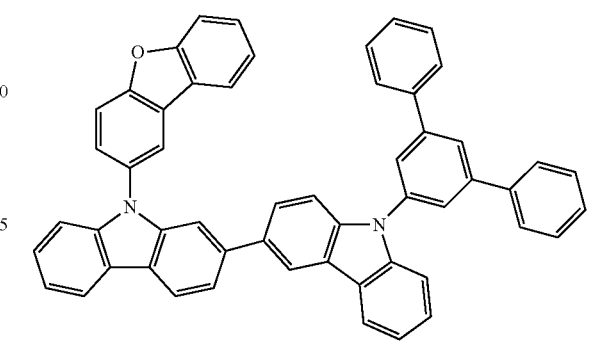
[E-81]
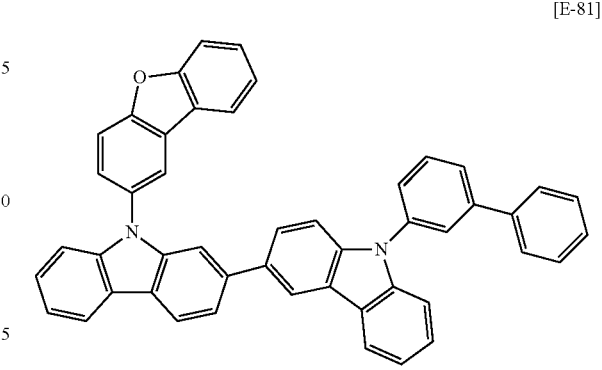

[E-82]
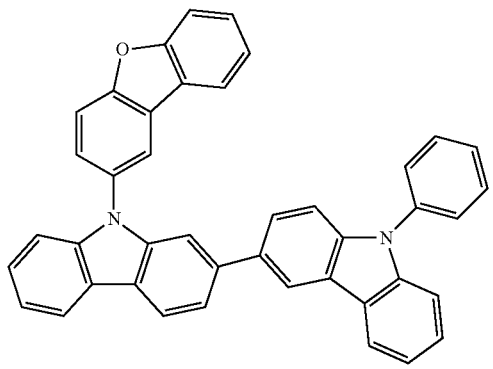
[E-86]
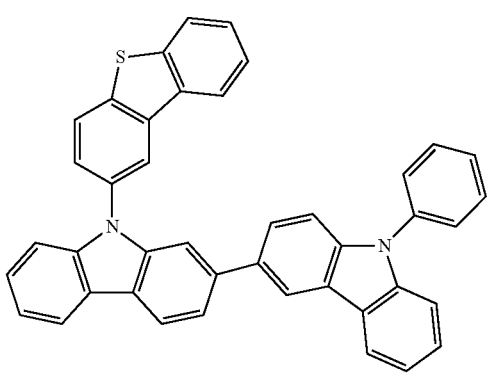
[E-83]
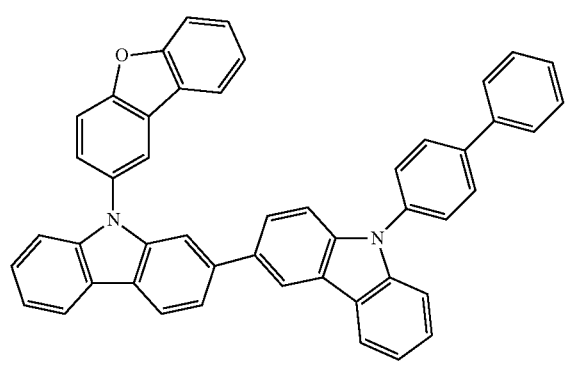
[E-87]
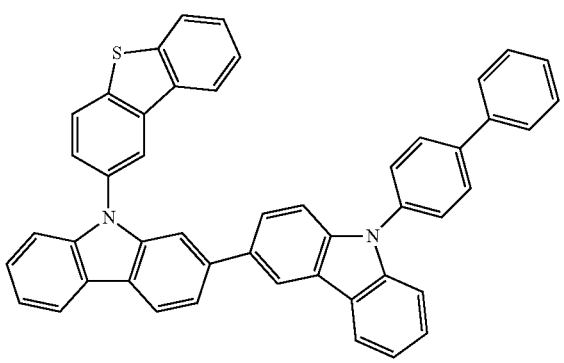
[E-84]
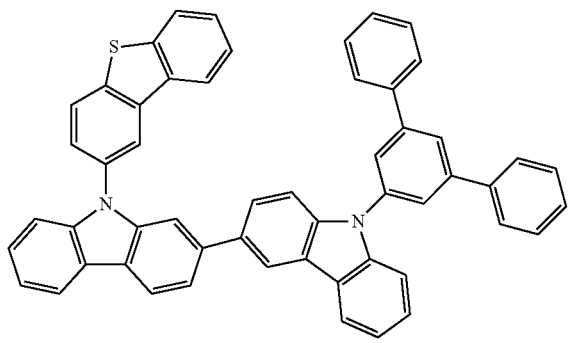
[E-88]
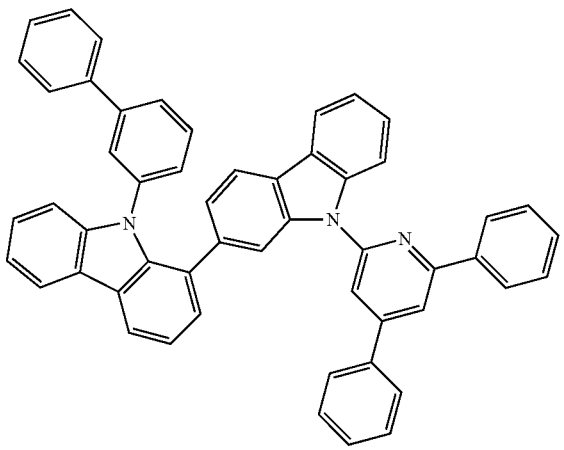
[E-85]
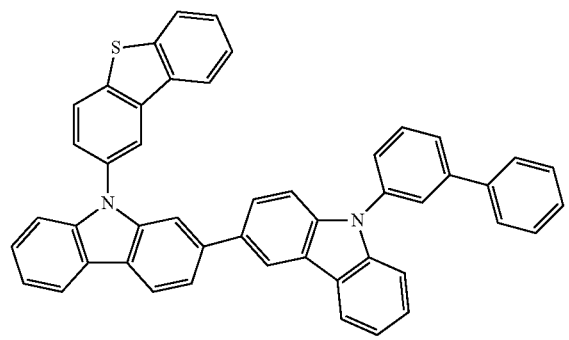
[E-89]
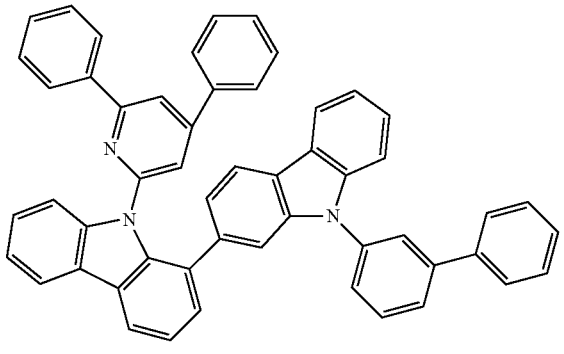

-continued
[E-90]
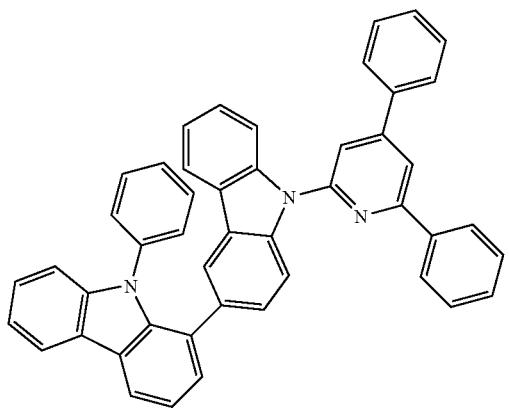
[E-91]
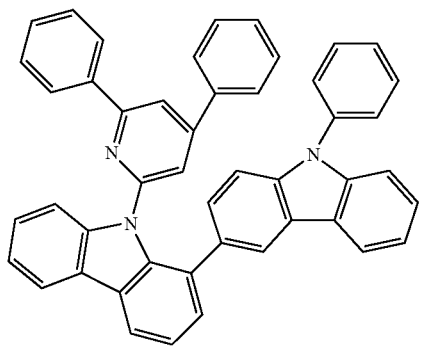
[E-92]
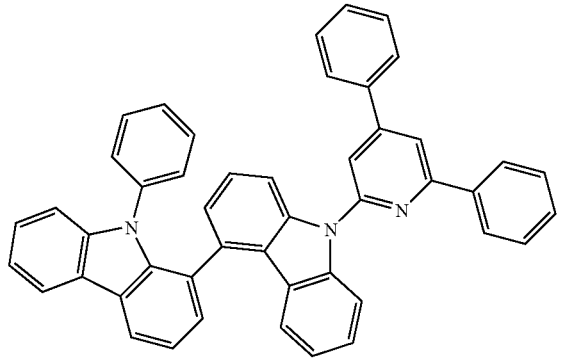
[E-93]
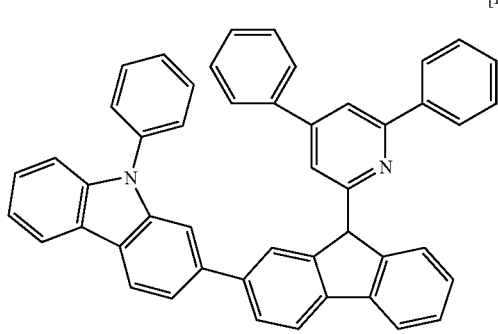
-continued
[E-94]
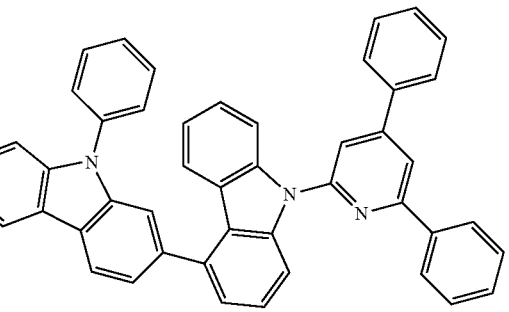
[E-95]
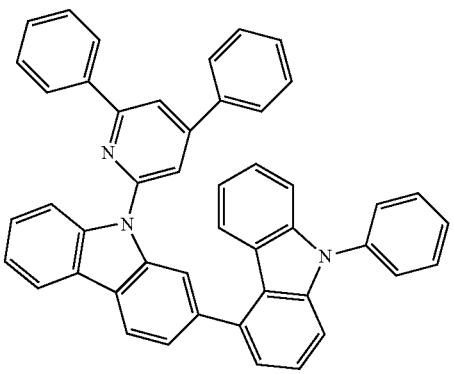
[E-96]
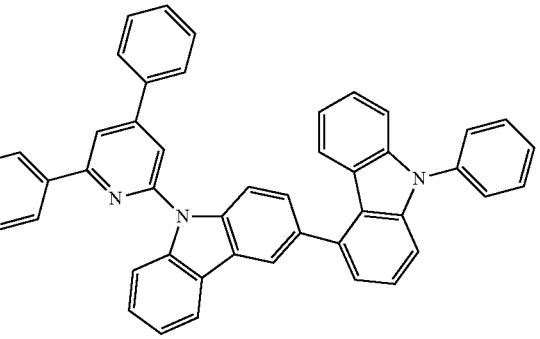
[E-97]
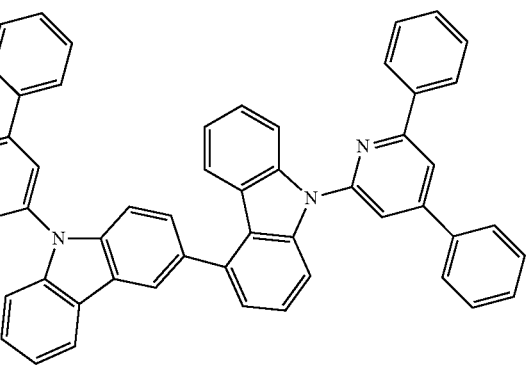

[E-98]
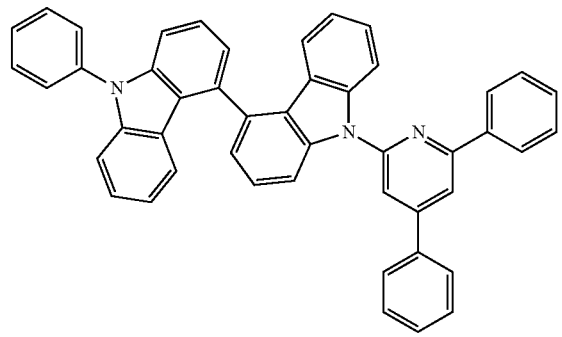
[E-101]
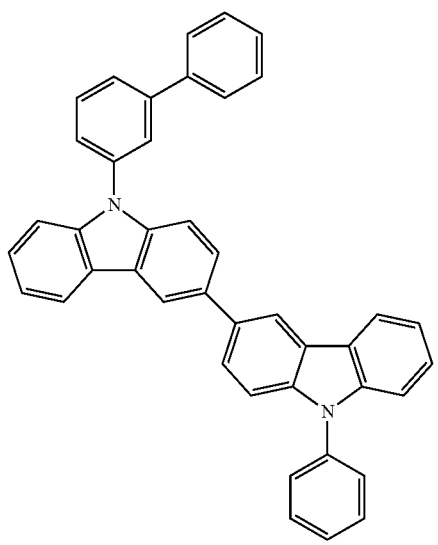
[E-99]
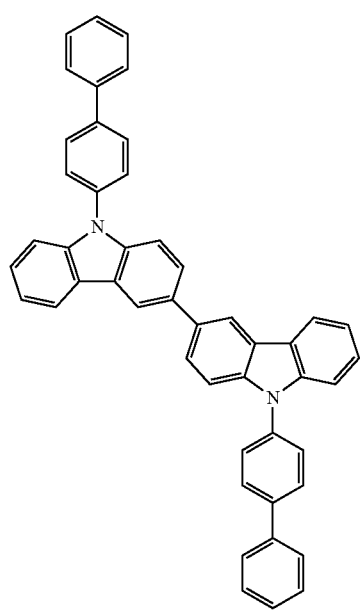
[E-102]
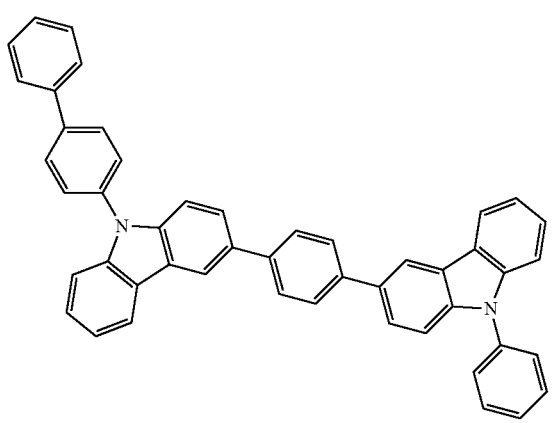
[E-100]
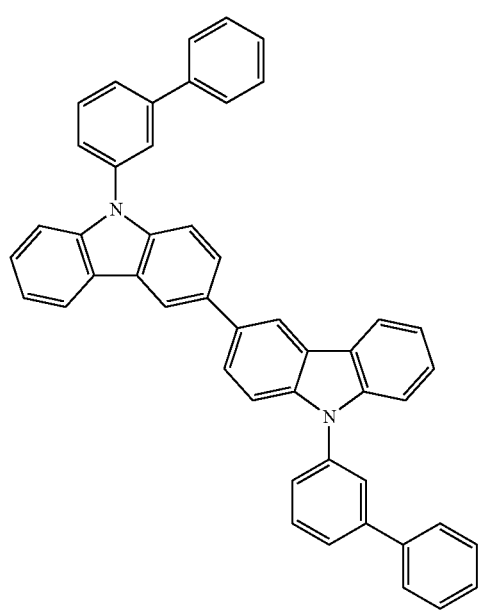
[E-103]

[E-104]
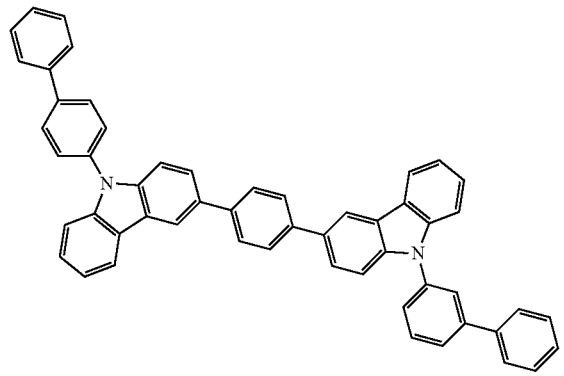
[E-105]
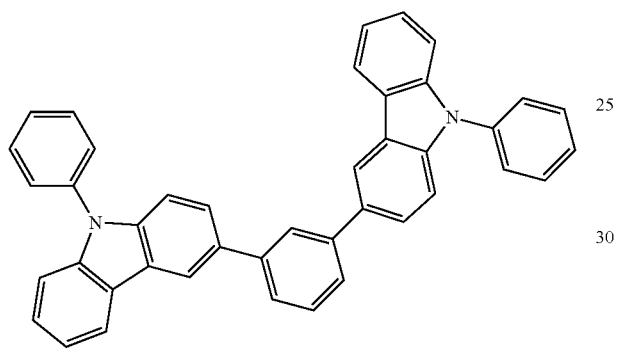
[E-106]
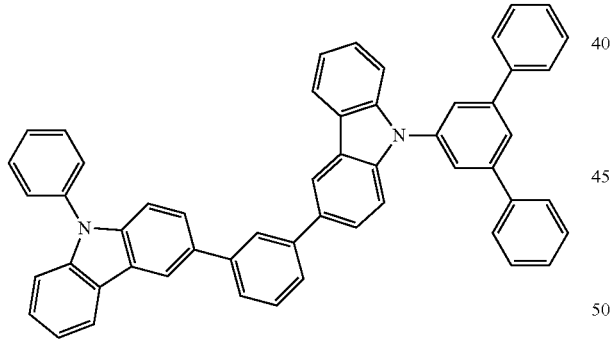
[E-107]
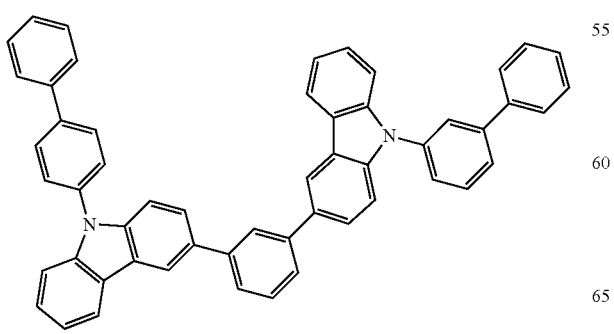
[E-108]
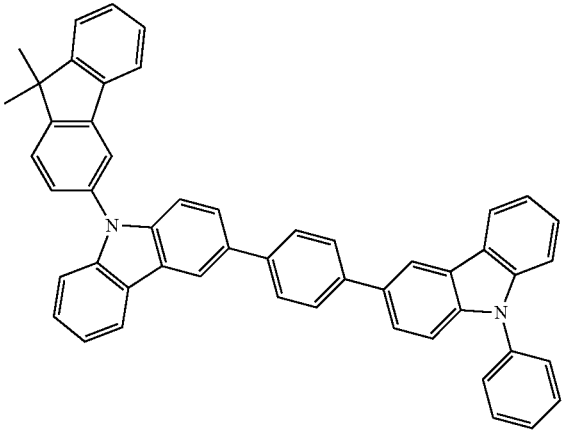
[E-109]
[E-110]
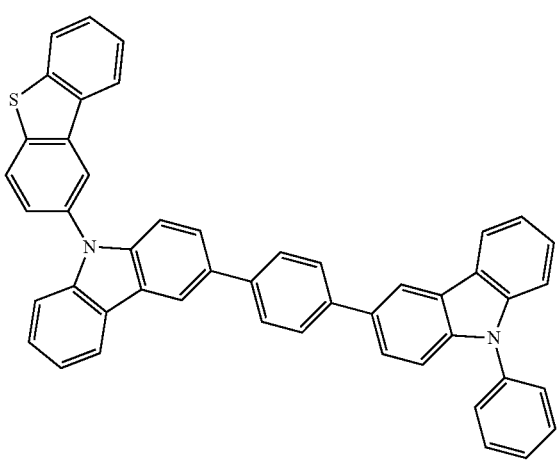

[E-111]
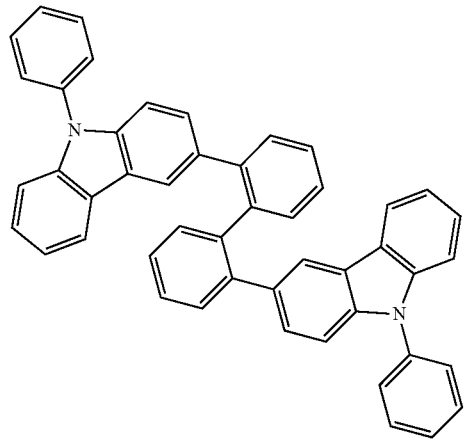
[E-112]
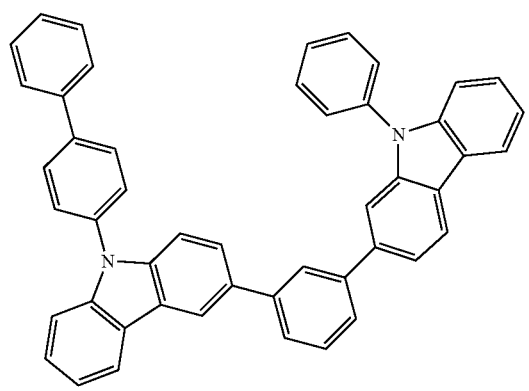
[E-113]
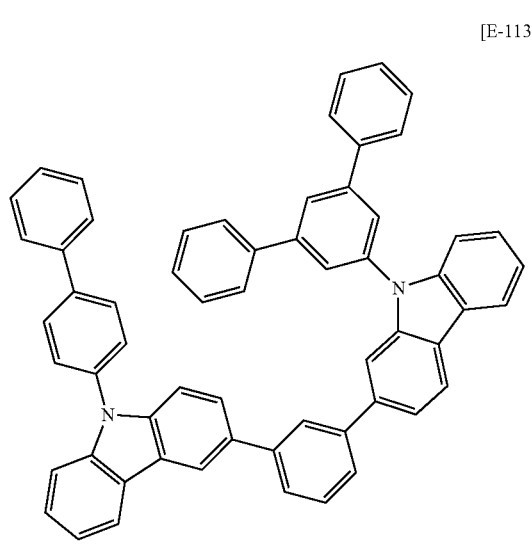
[E-114]
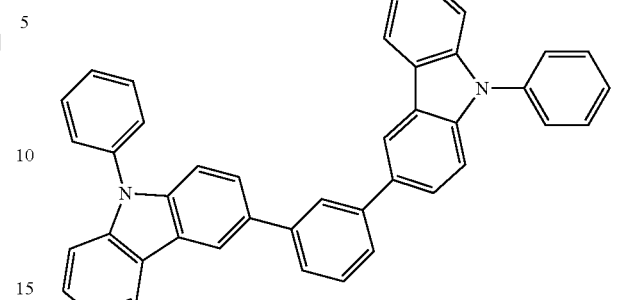
[E-115]
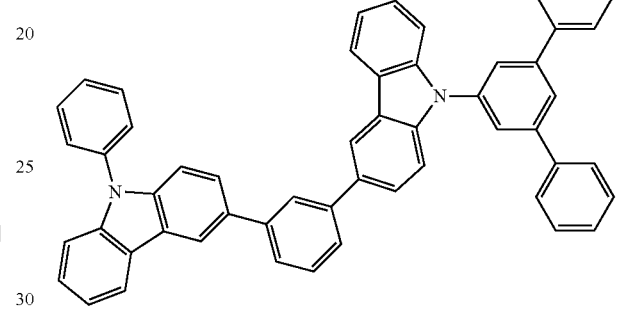
[E-116]
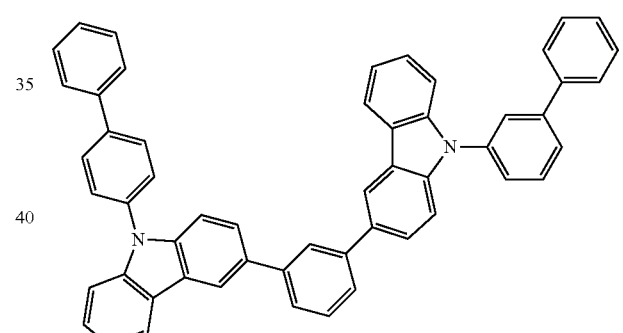
[E-117]
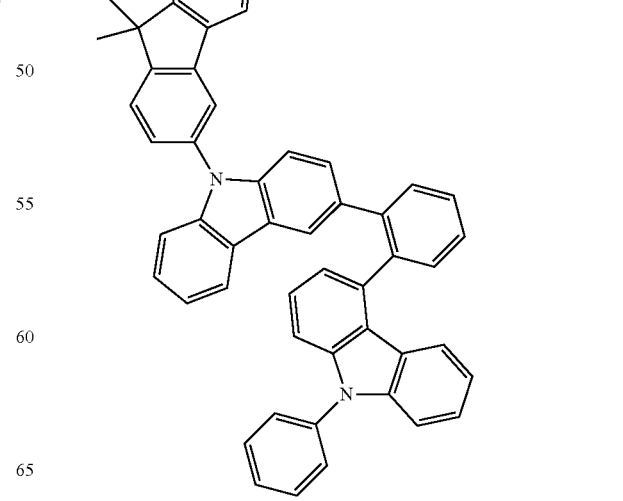

[E-118]
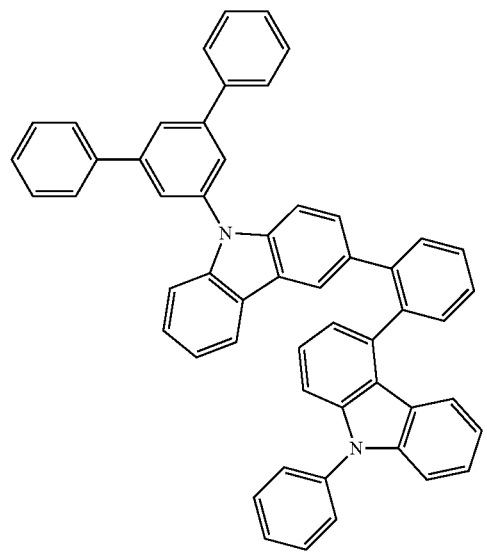
[E-121]
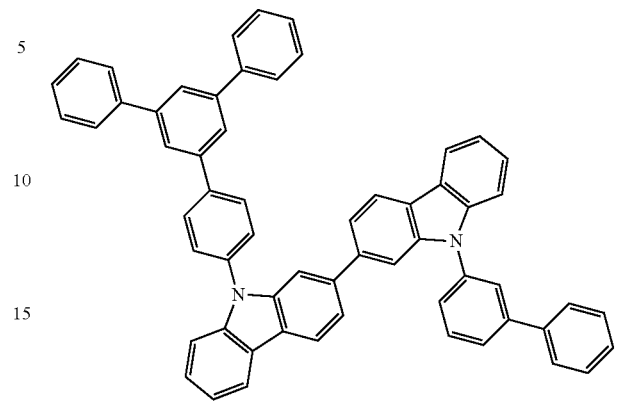
[E-119]
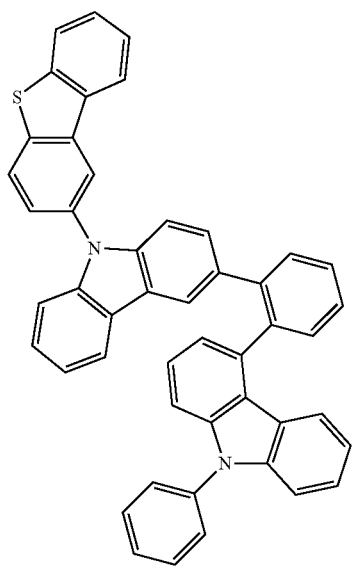
[E-122]
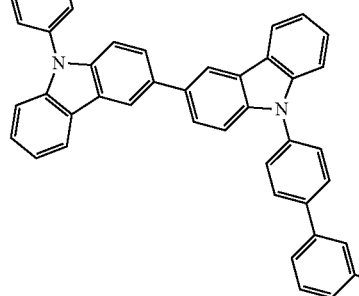
[E-120]
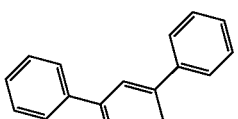
[E-123]
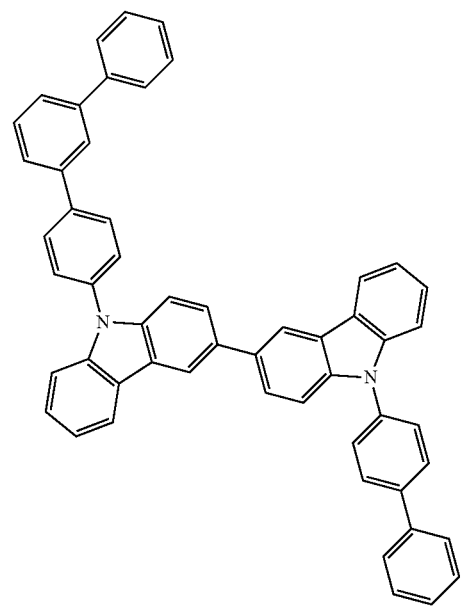

[E-124]
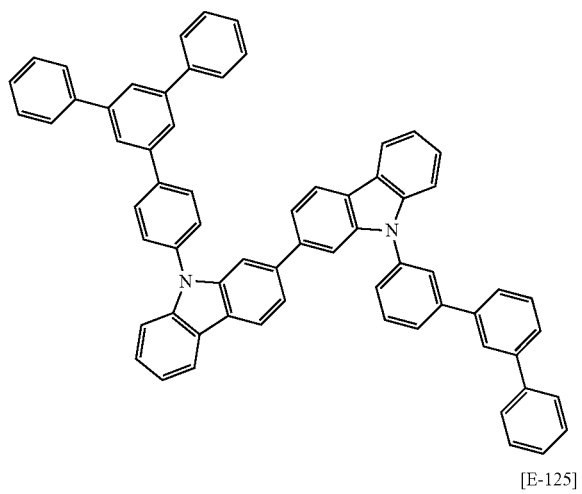
[E-127]
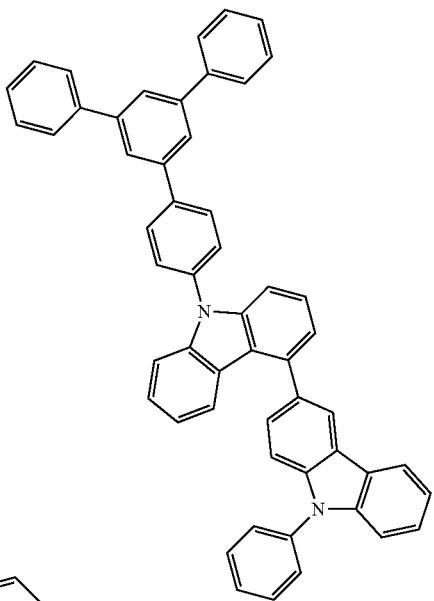
[E-125]
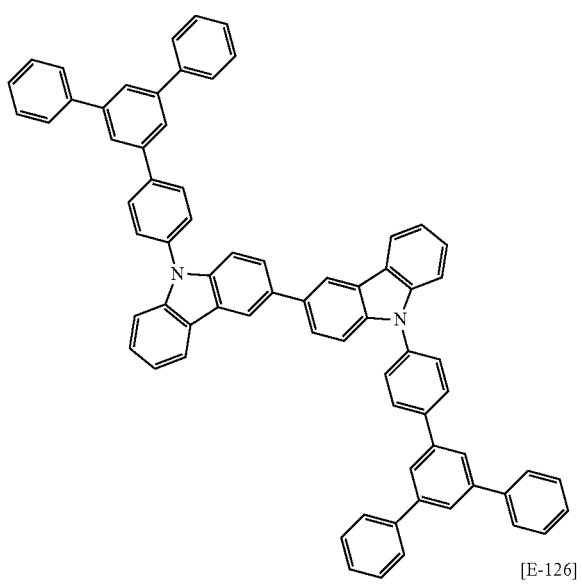
[E-128]
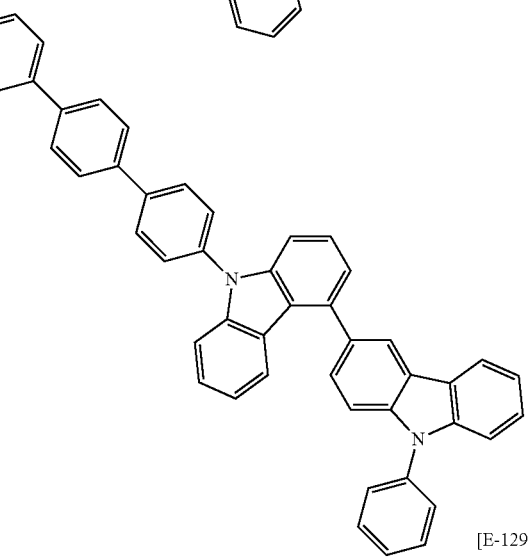
[E-126]
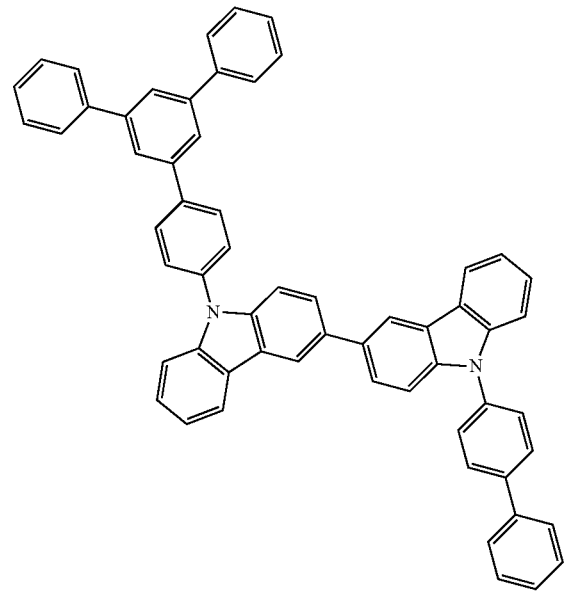
[E-129]
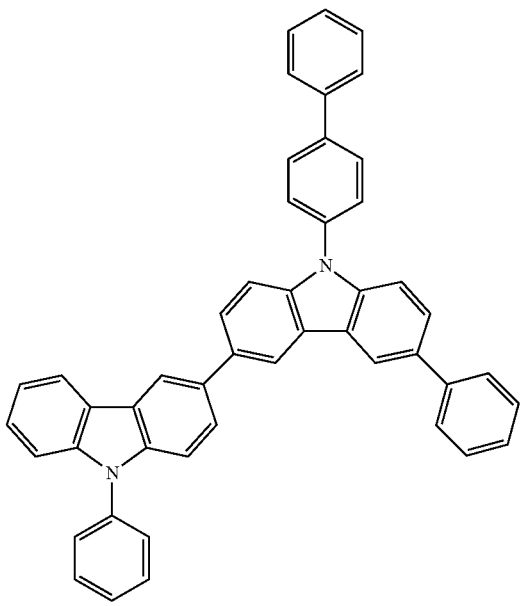

[E-130]
[E-133]
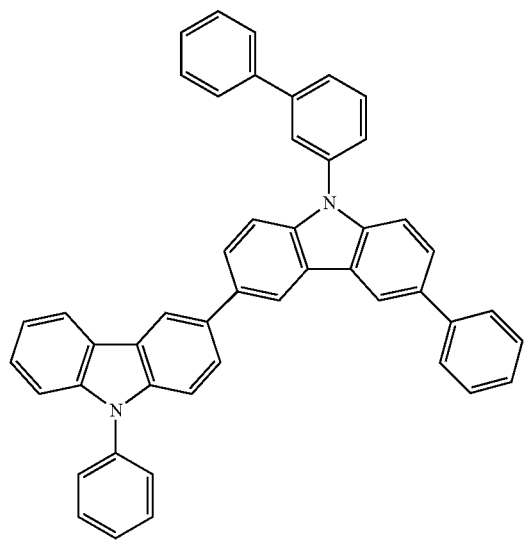
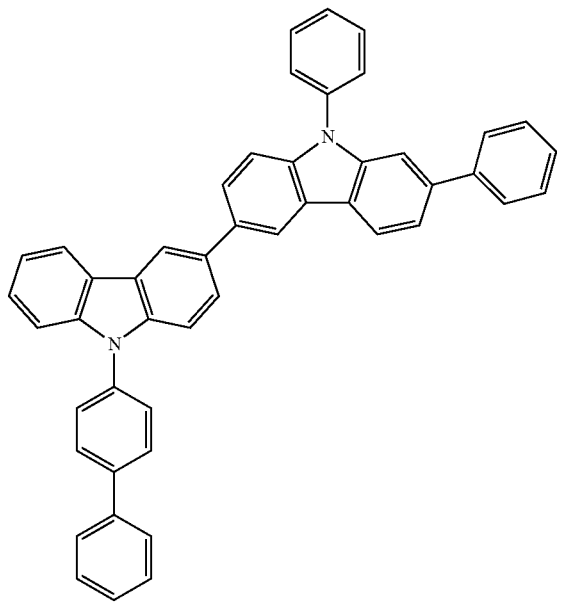
[E-131]
[E-134]
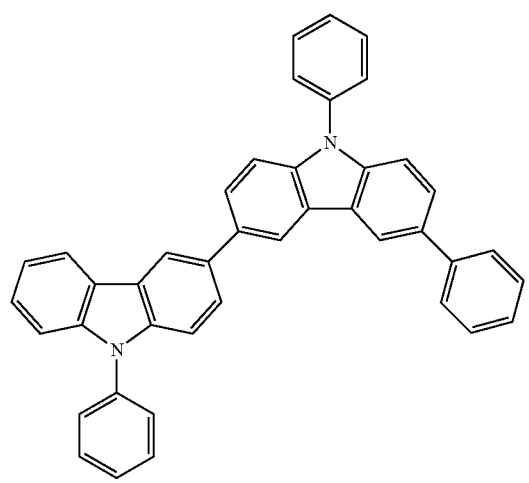
[E-132]
[E-135]
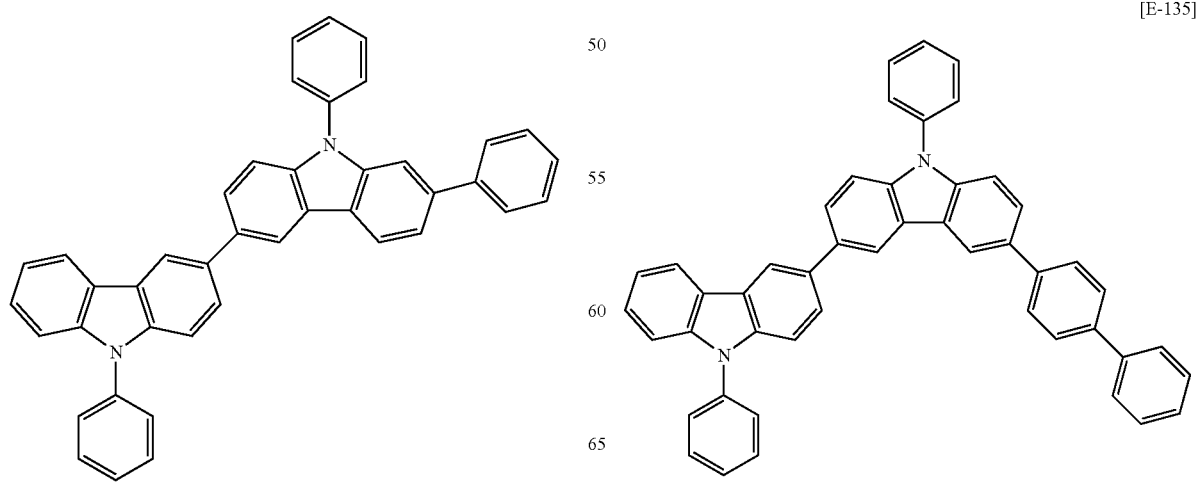

[E-136]
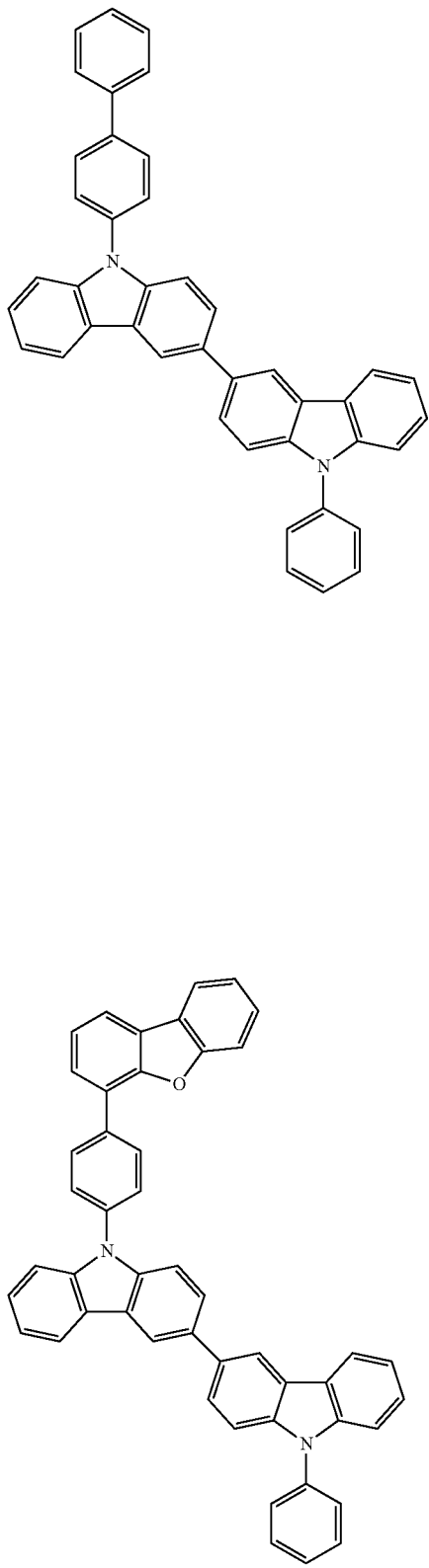
[E-137]
[E-138]
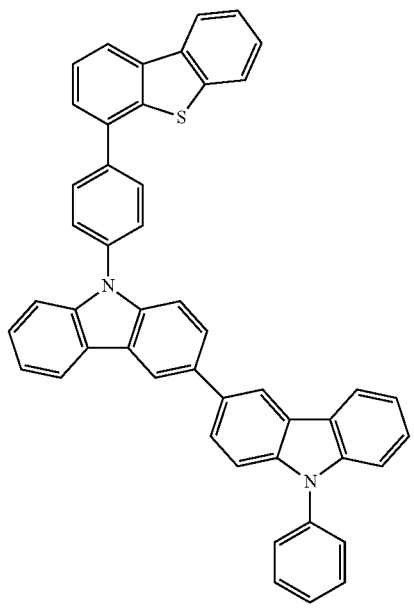
[F-1]
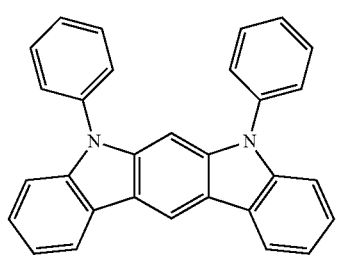
[F-2]
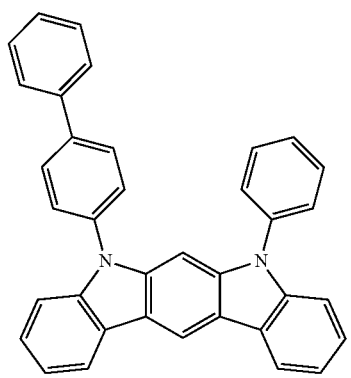
[F-3]
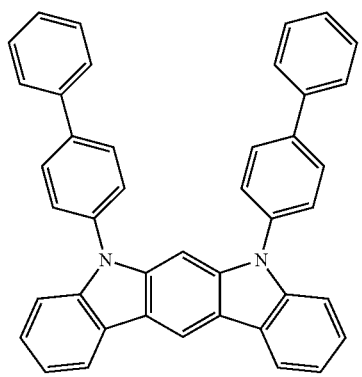

[F-4]
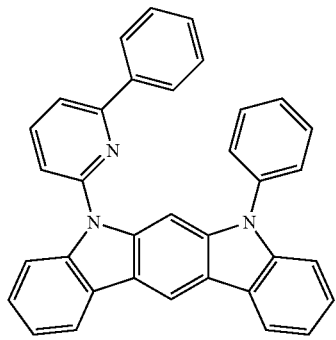
[F-5]
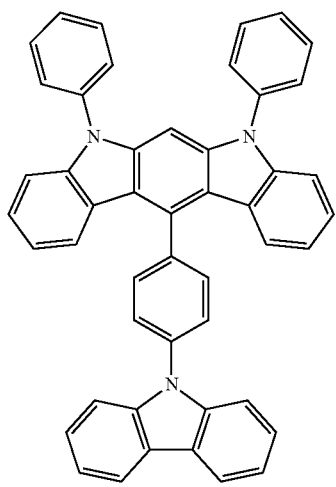
[F-6]
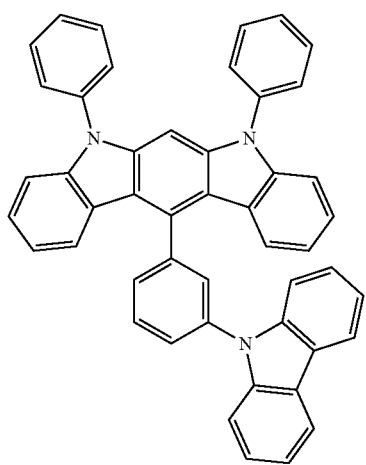
[F-7]
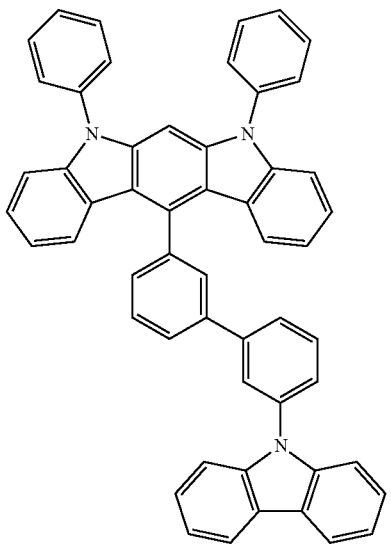
[F-8]
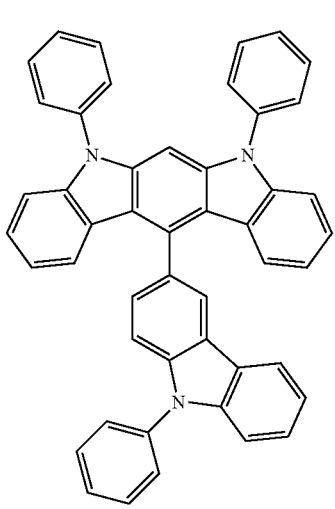
[F-9]
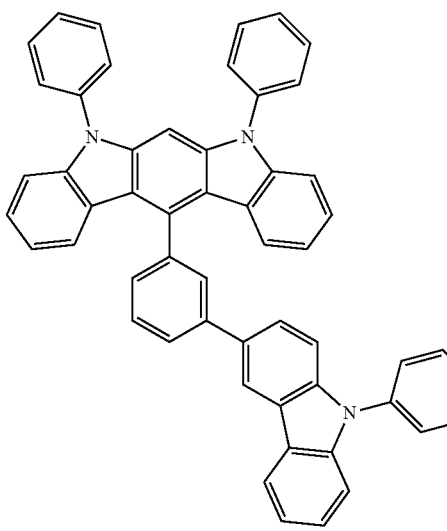

[F-10]
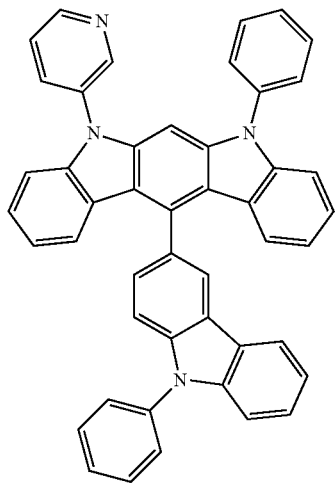
[F-11]
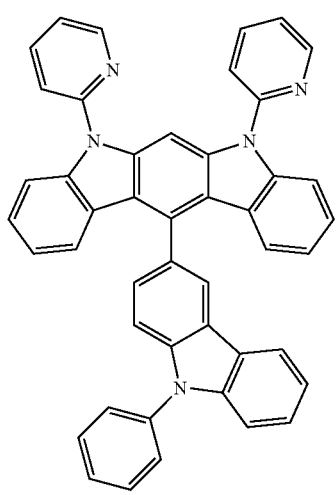
[F-12]
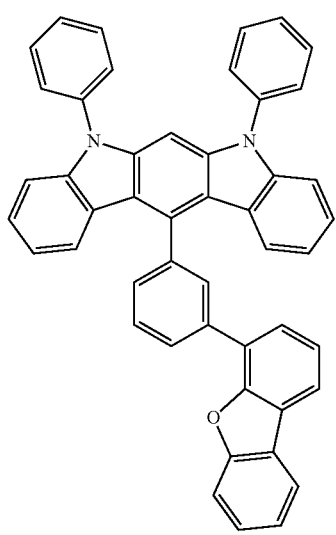
[F-13]
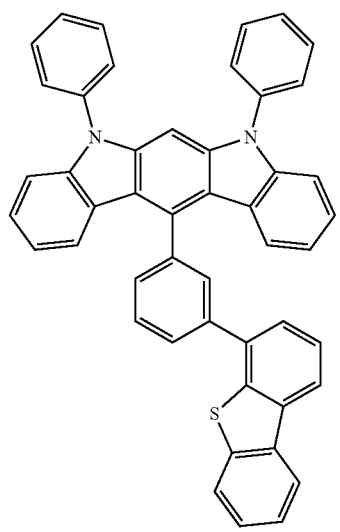
[F-14]
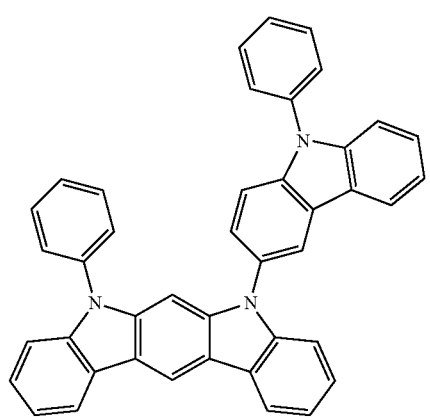
[F-15]
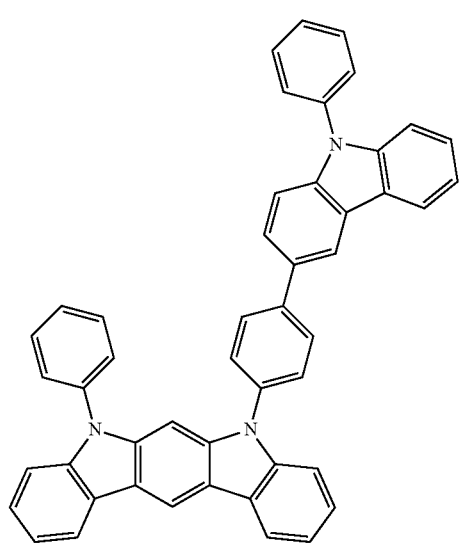

[F-16]
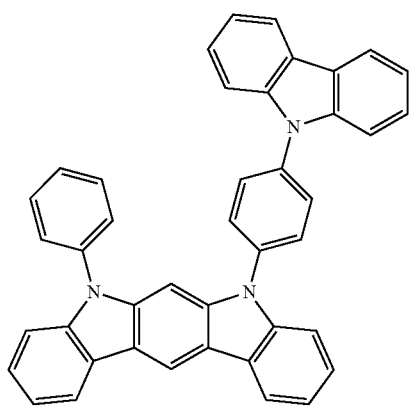
[F-17]
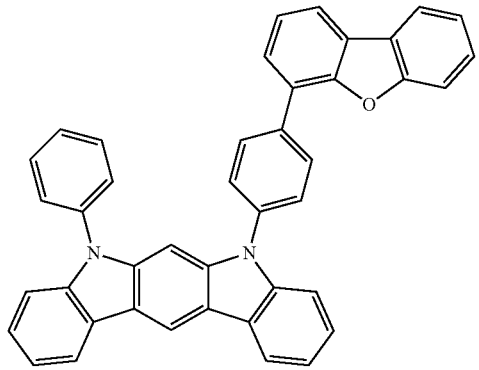
[F-18]
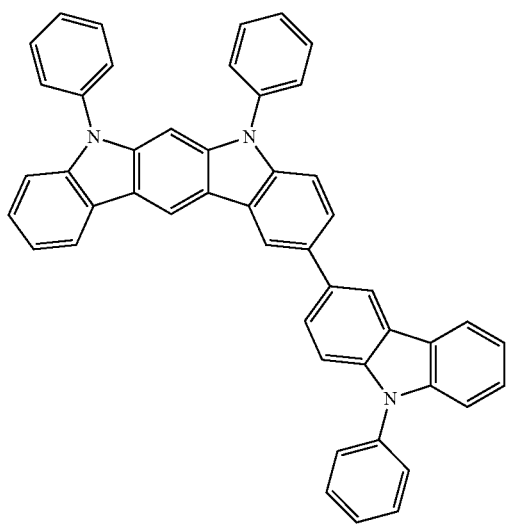
[F-19]
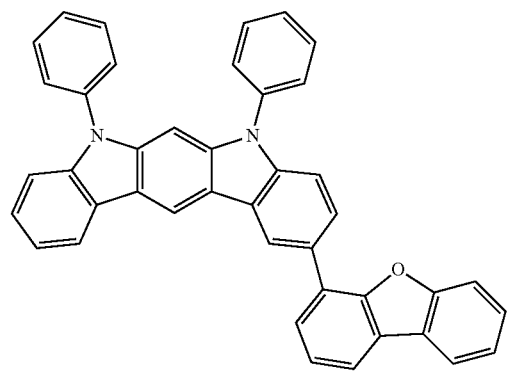
[F-20]
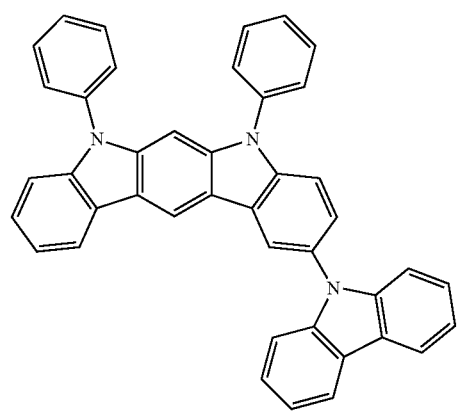
[F-21]
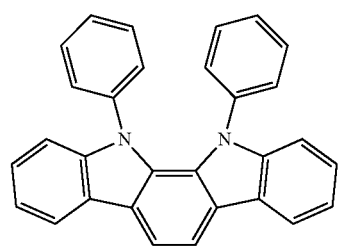
[F-22]
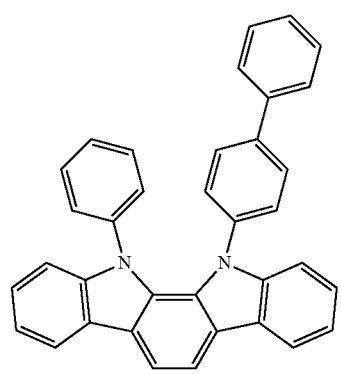

[F-23]
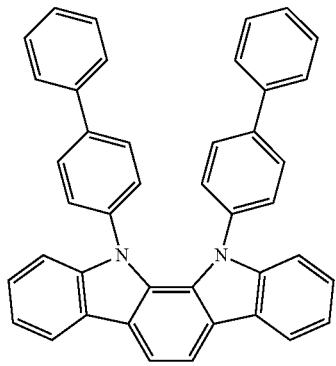
[F-24]
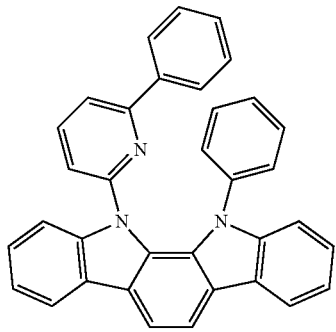
[F-25]
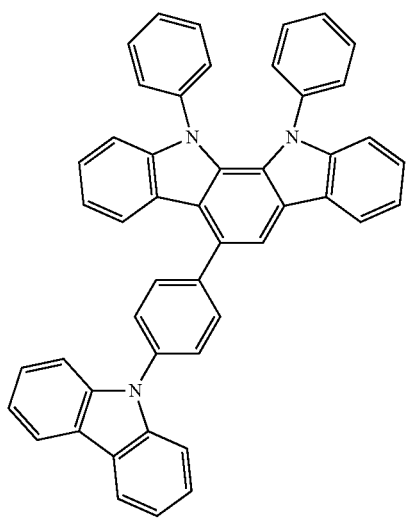
[F-26]
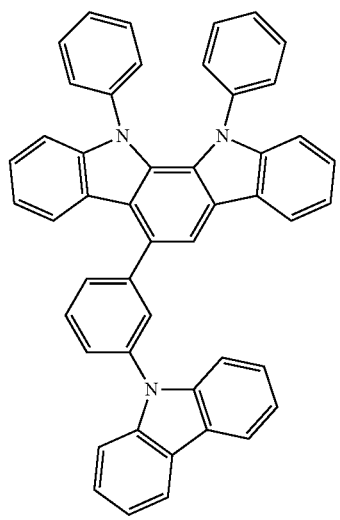
[F-27]
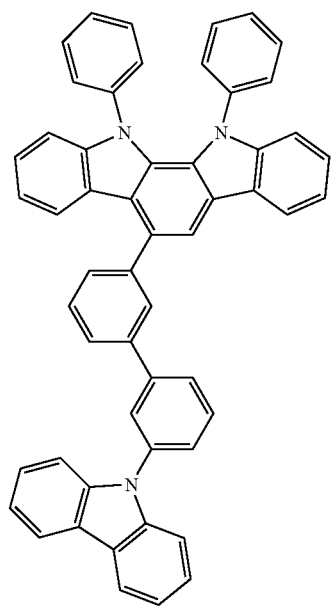
[F-28]
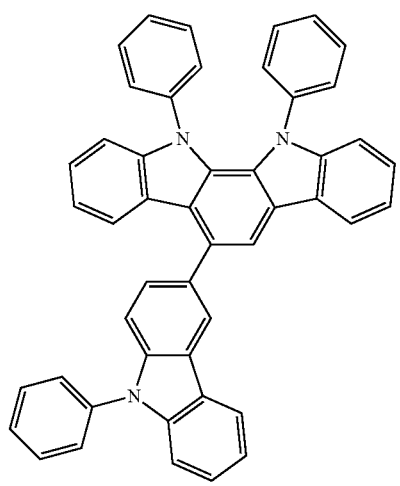

[F-29]
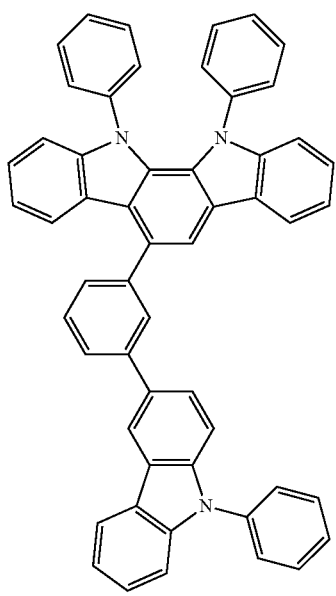
[F-30]
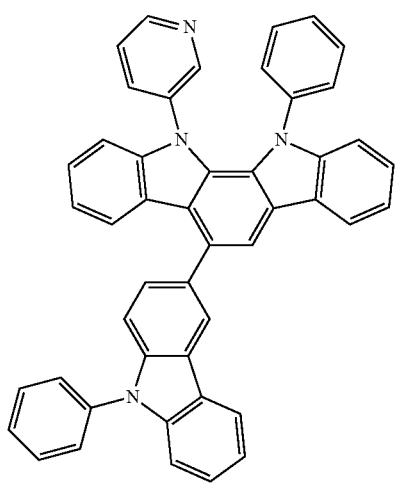
[F-31]
[F-32]
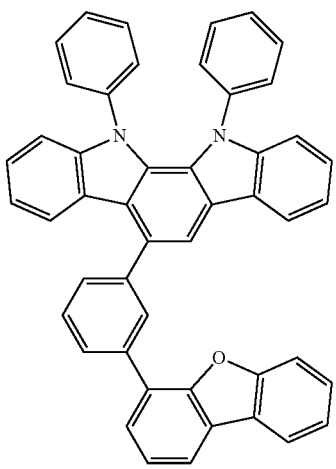
[F-33]
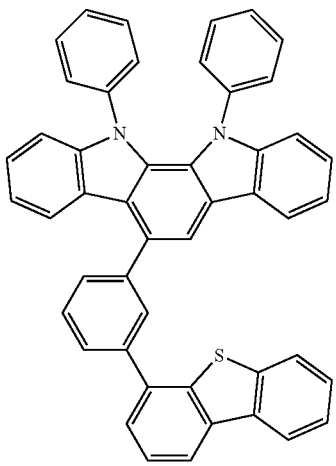
[F-34]
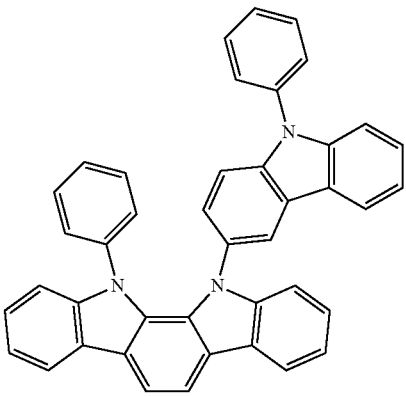

[F-35]
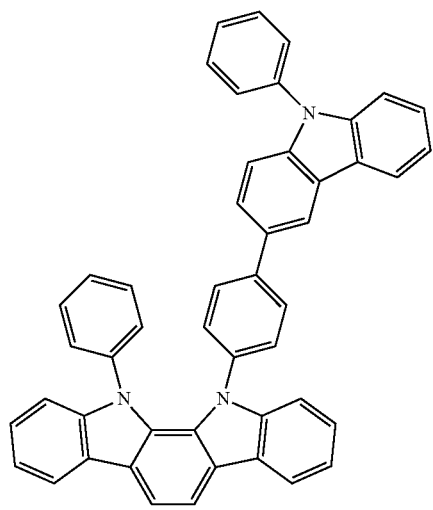
[F-36]
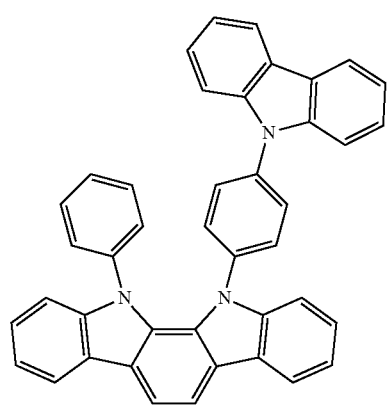
[F-37]
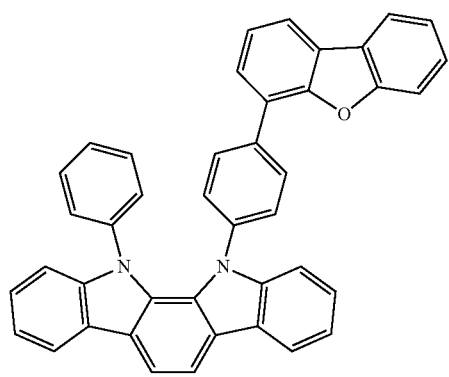
[F-38]
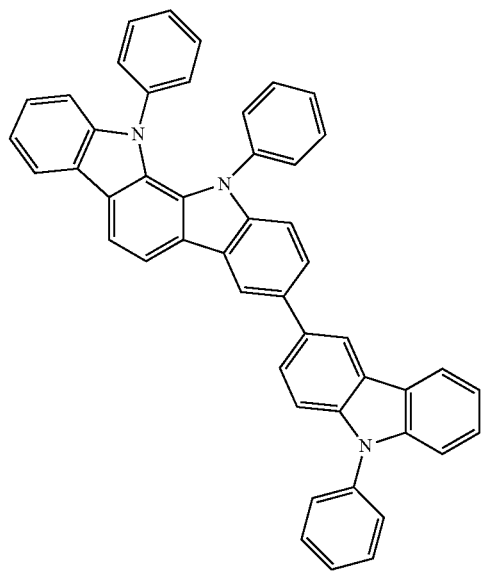
[F-39]
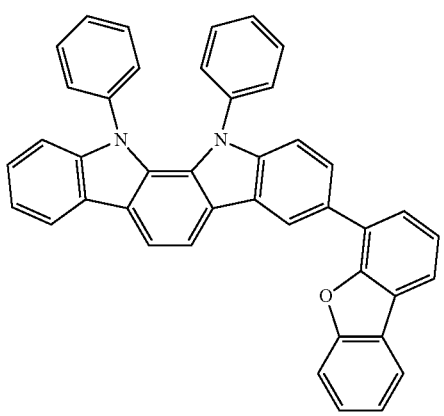
[F-40]
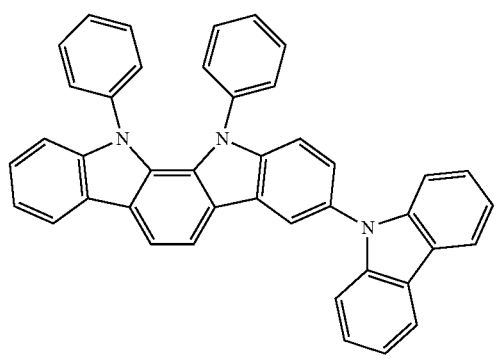
[F-41]
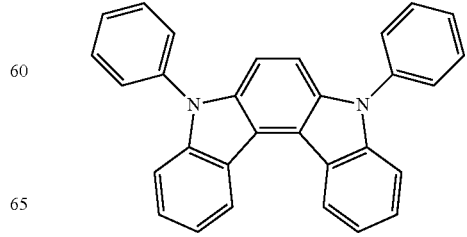

[F-42]
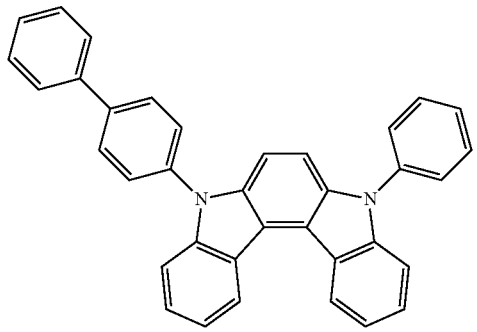
[F-43]
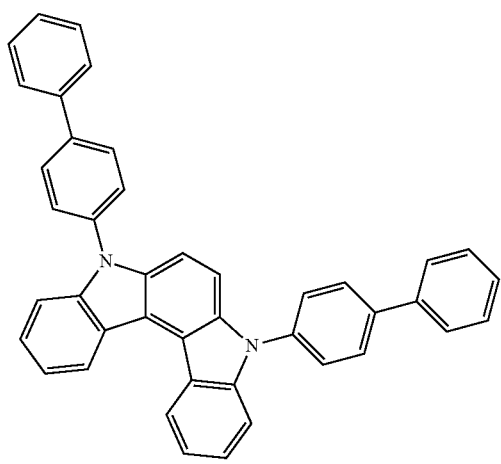
[F-44]
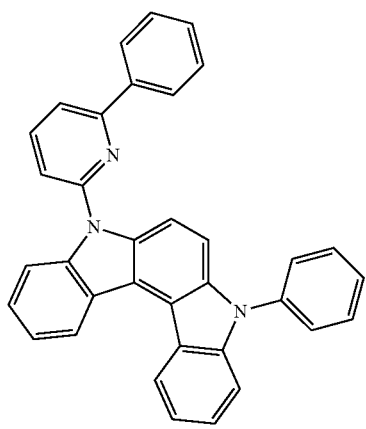
[F-45]
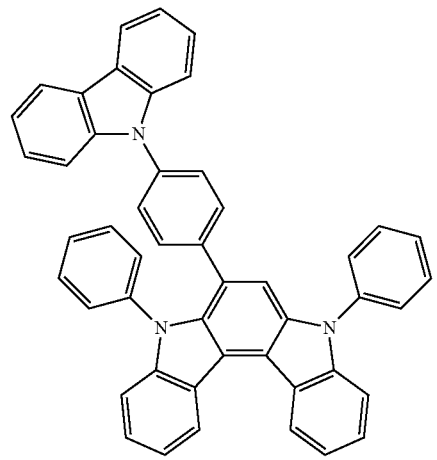
[F-46]
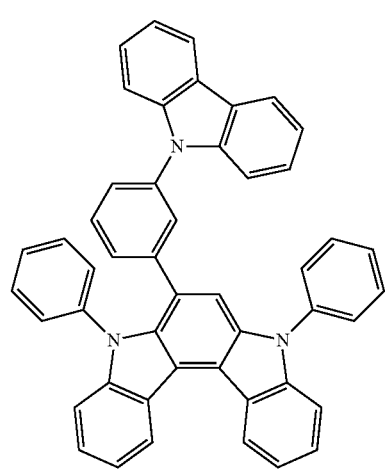
[F-47]
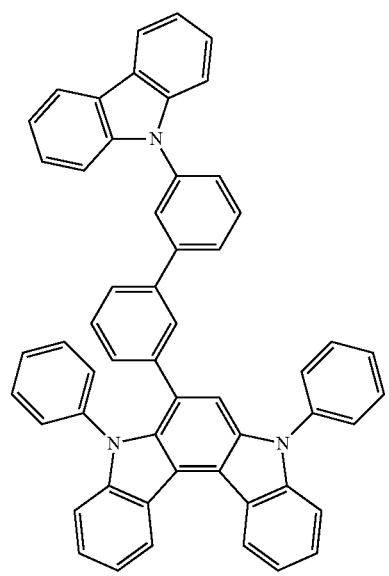

[F-48]
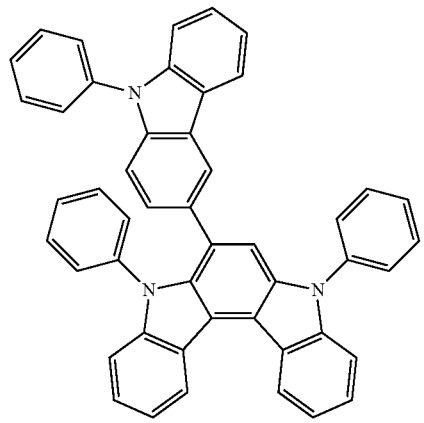
[F-49]
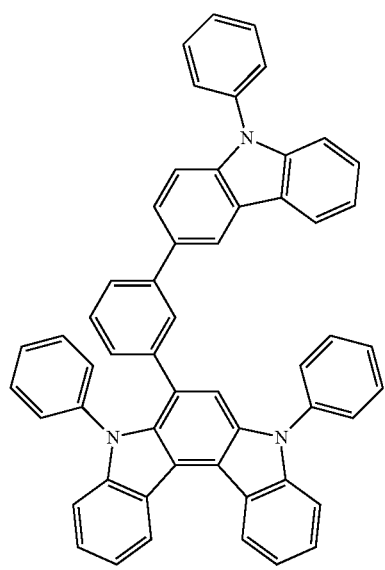
[F-50]
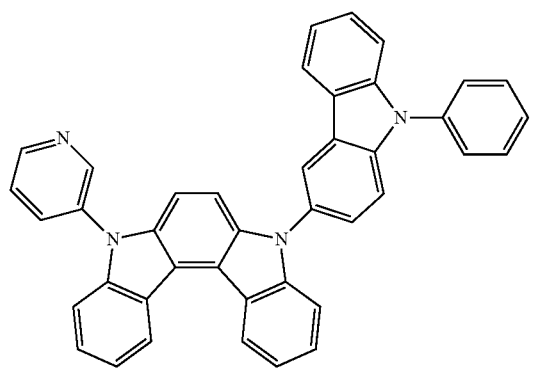
[F-51]
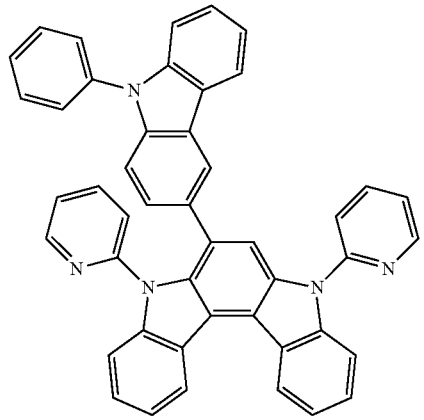
[F-52]
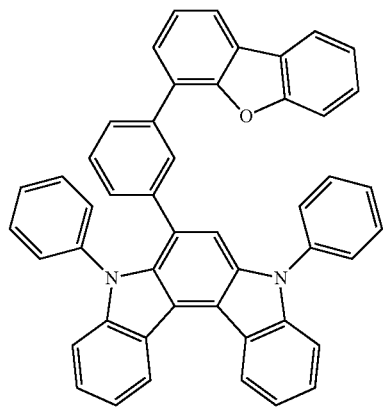
[F-53]
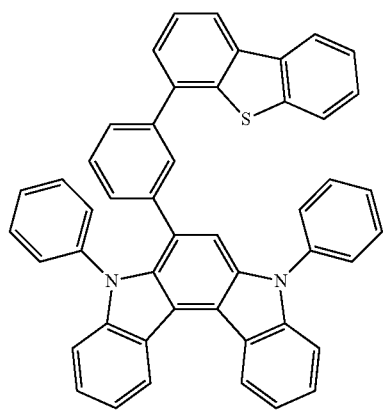
[F-54]
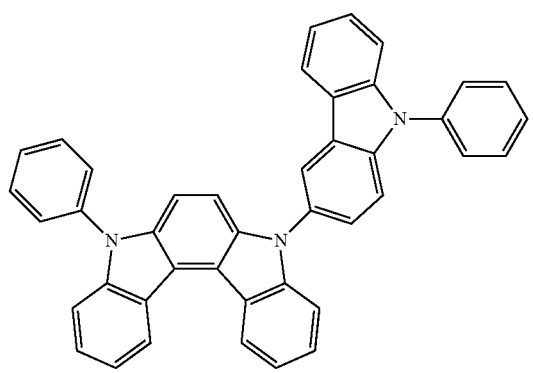

[F-55]
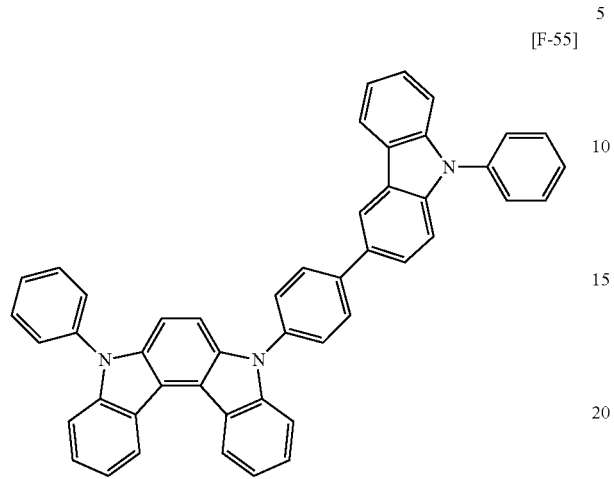
[F-56]
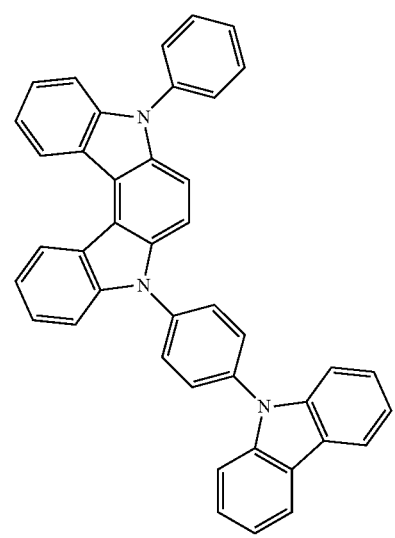
[F-57]
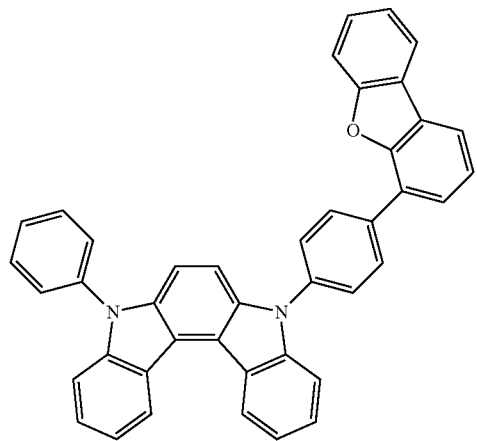
[F-58]
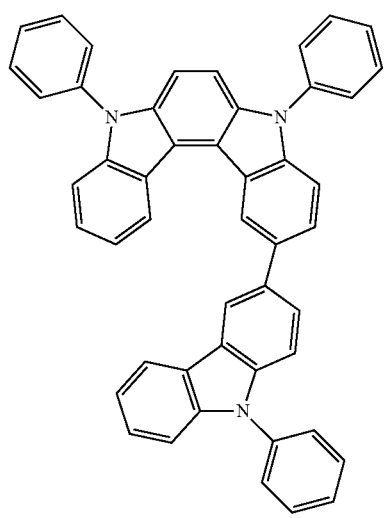
[F-59]
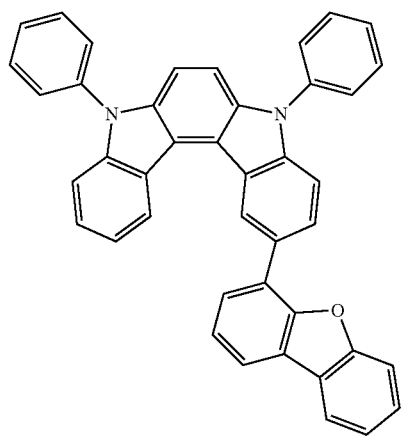
[F-60]
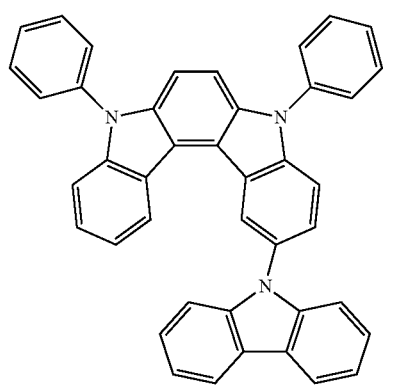

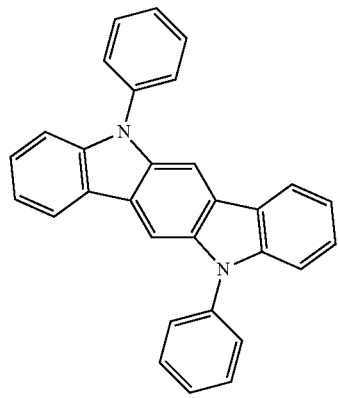
[F-61]
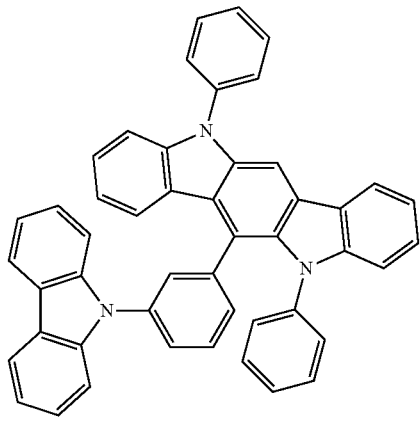
[F-64]
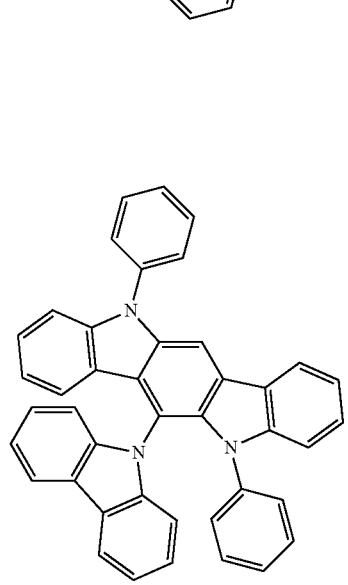
[F-62]
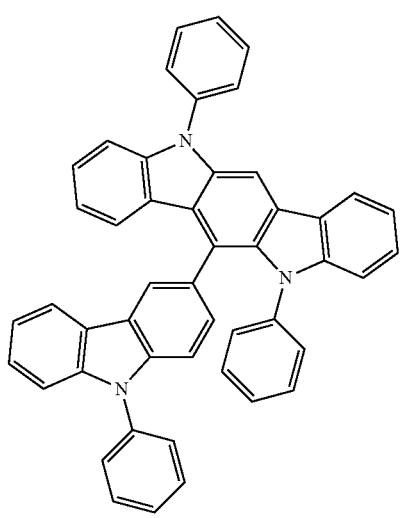
[F-65]
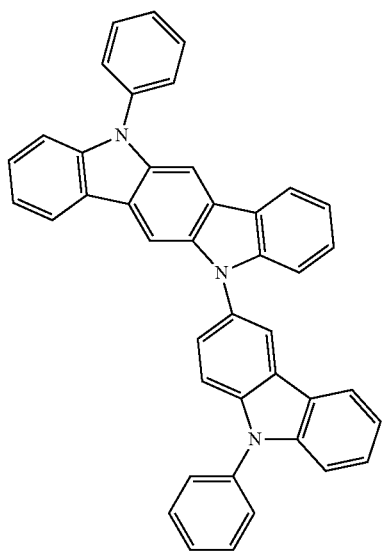
[F-63]
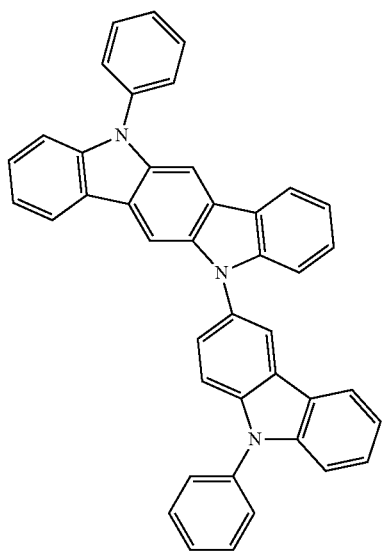
[F-66]

[F-67]
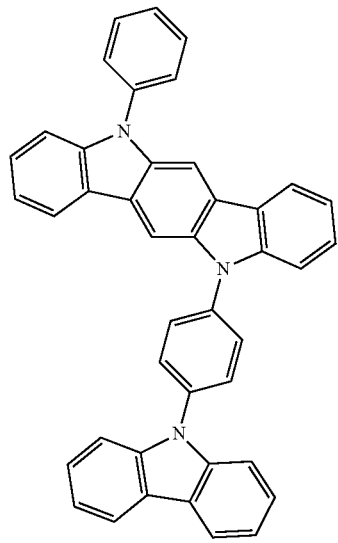
[F-68]
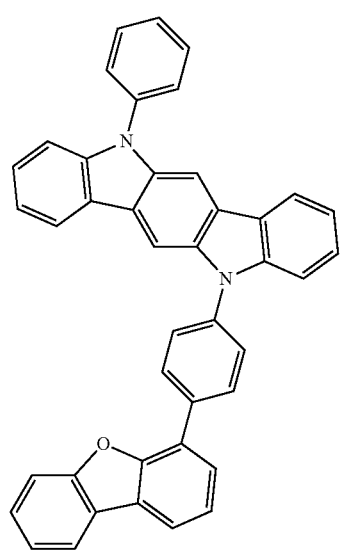
[F-69]
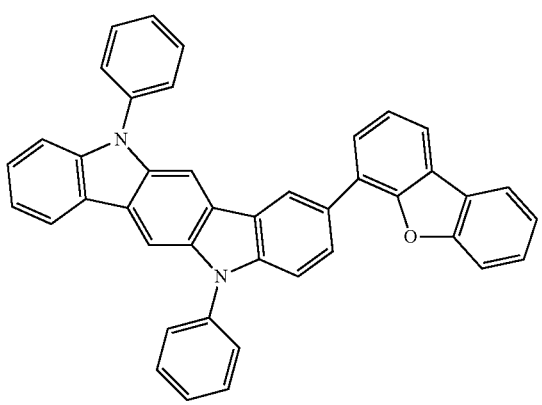
[F-70]
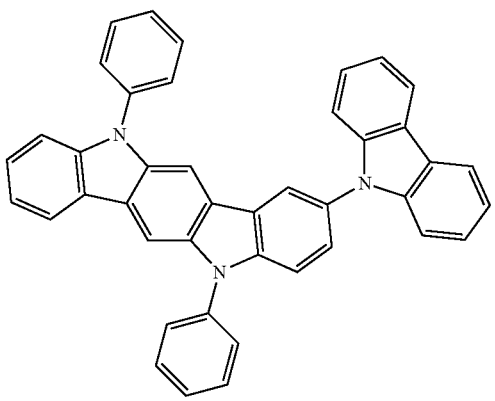
[F-71]
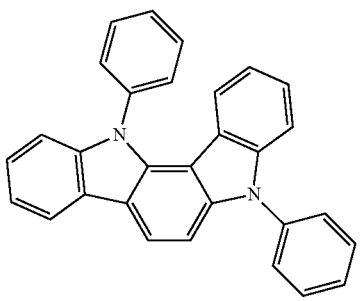
[F-72]
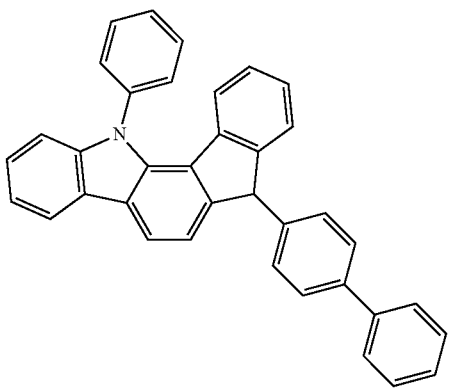
[F-73]
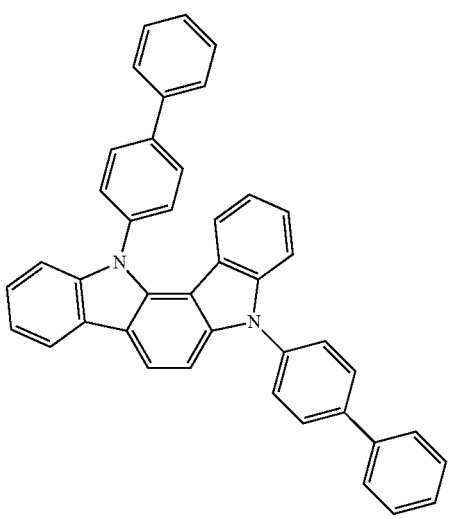

[F-74]
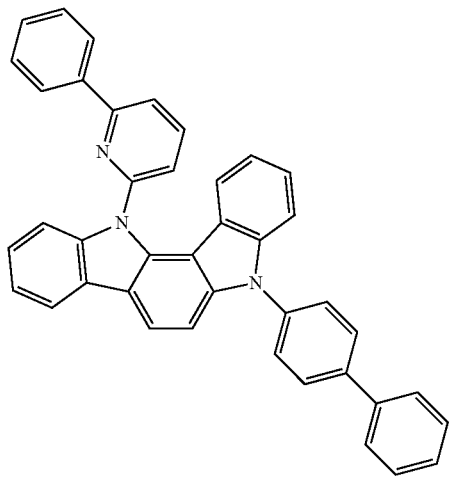
[F-75]
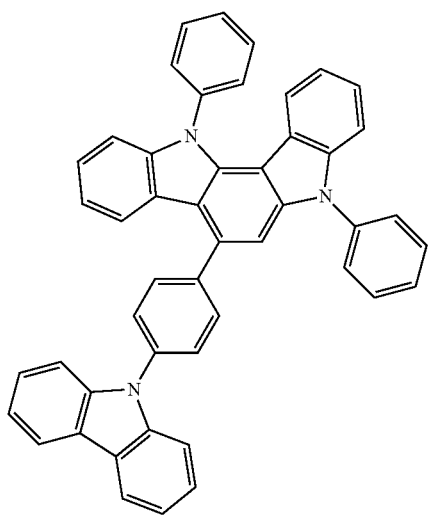
[F-76]
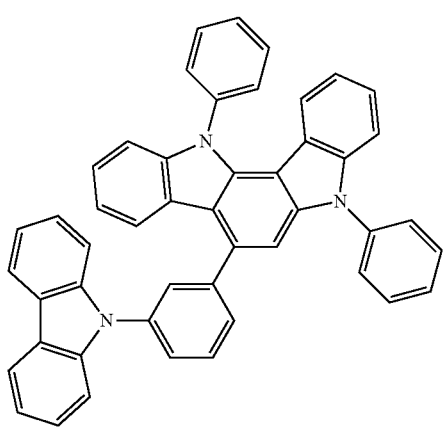
[F-77]
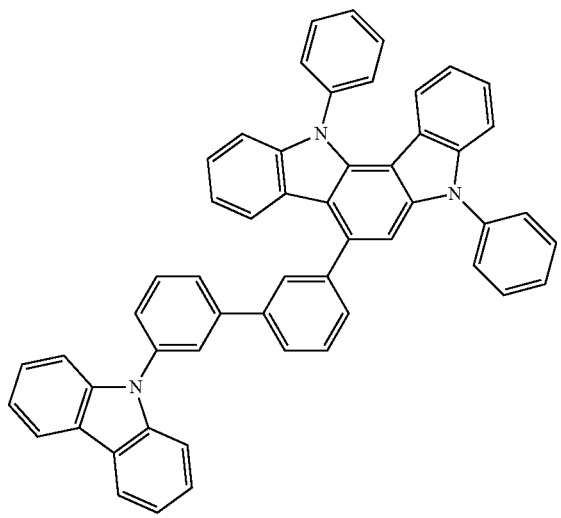
[F-78]
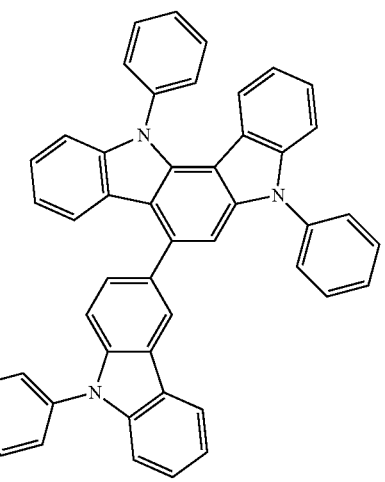
[F-79]
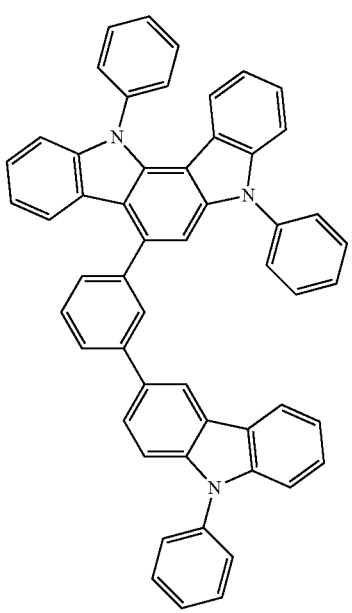

[F-80]
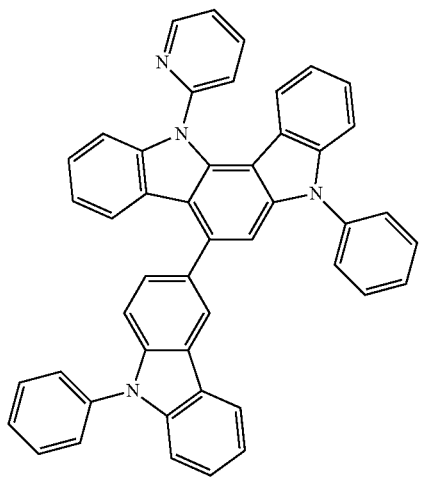
[F-81]
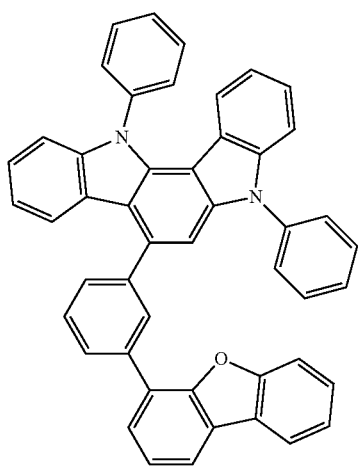
[F-82]
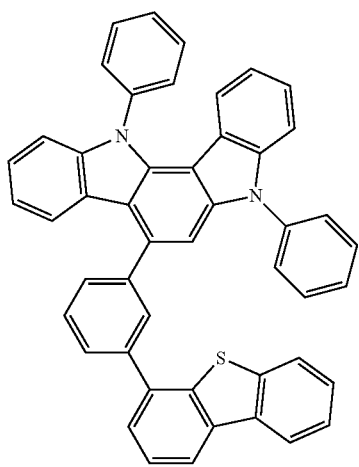
[F-83]
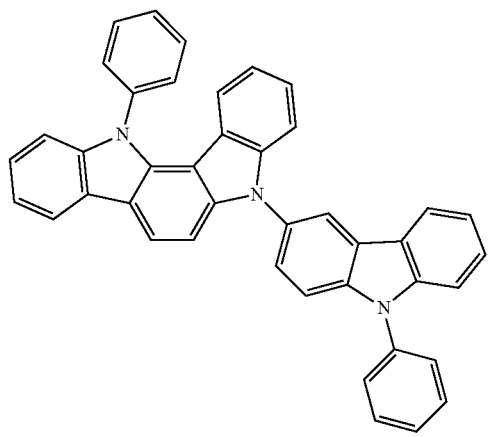
[F-84]
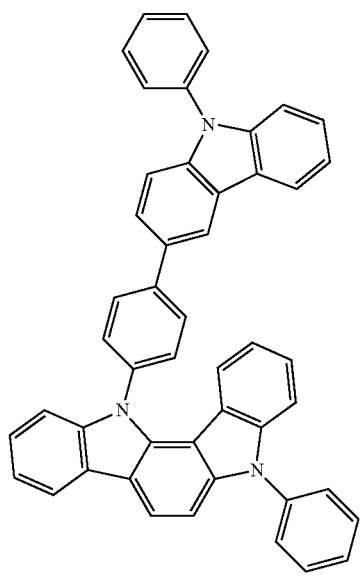
[F-85]
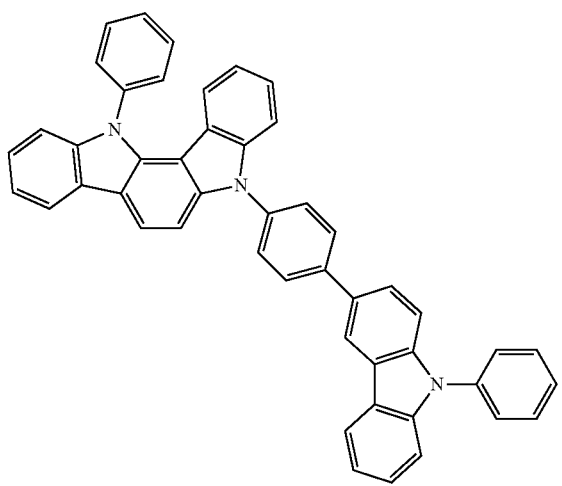

[F-86]
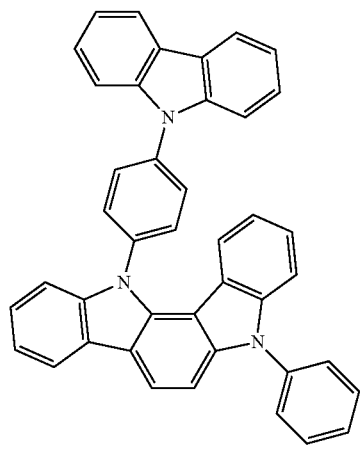
[F-89]
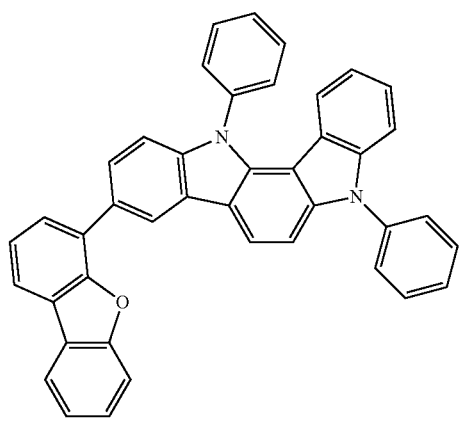
[F-87]
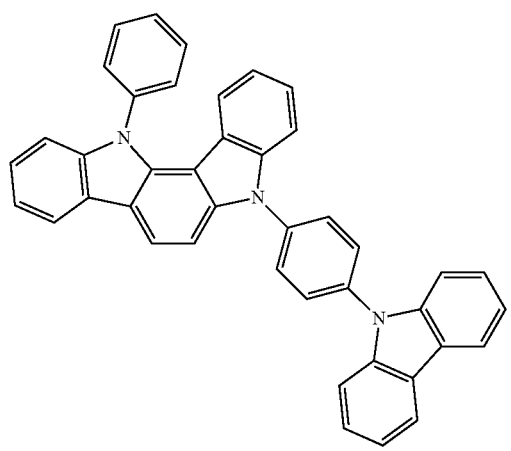
[F-90]
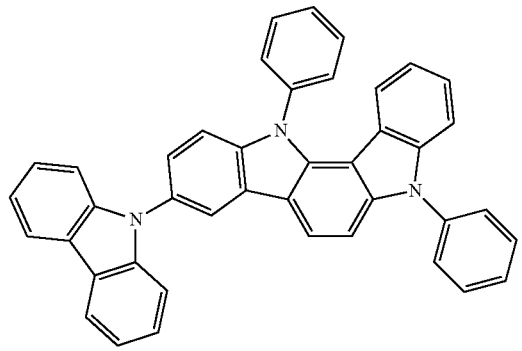
[F-88]
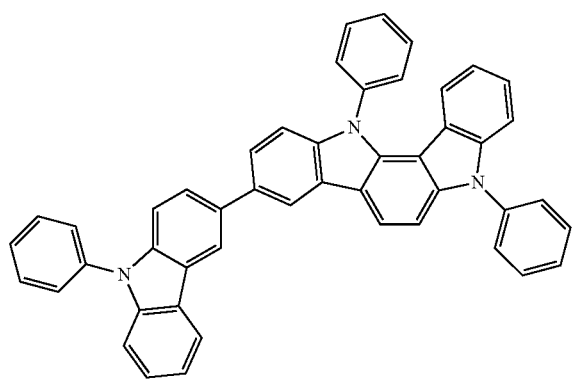
[F-91]
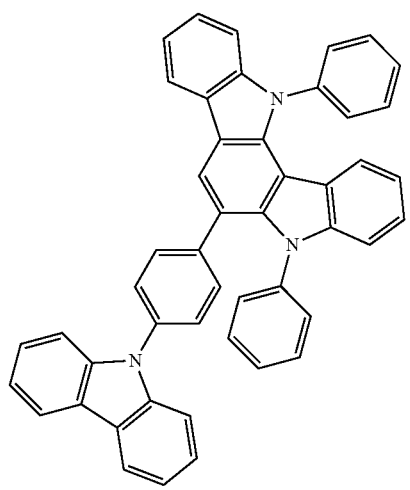

-continued
[F-92]
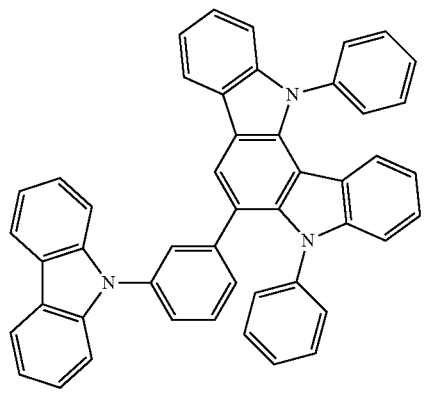
[F-93]
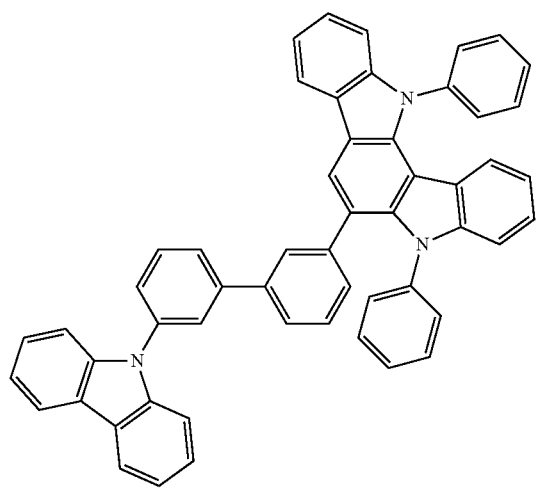
[F-94]
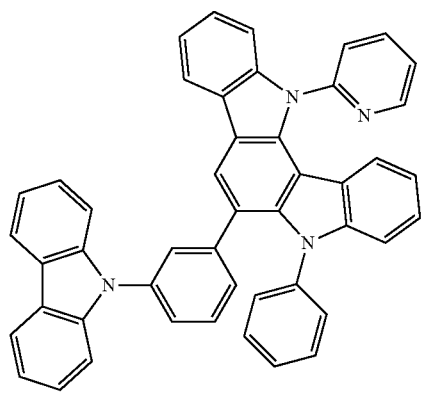
-continued
[F-95]
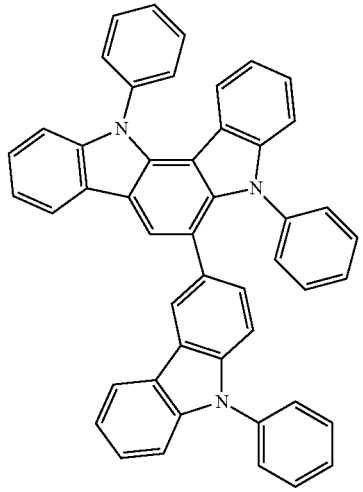
[F-96]
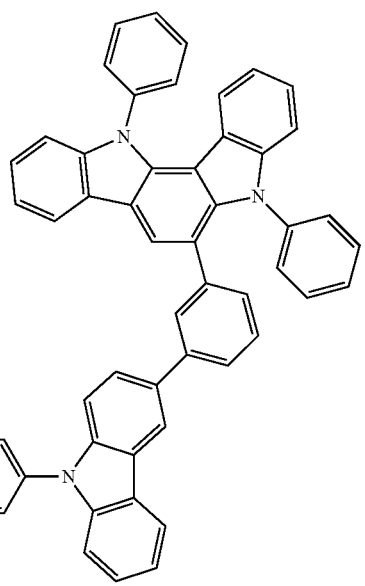
[F-97]
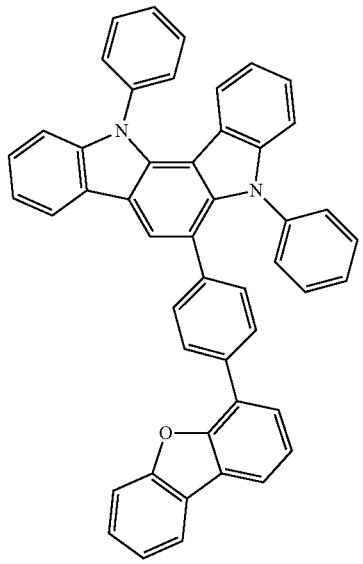

-continued

[F-98]

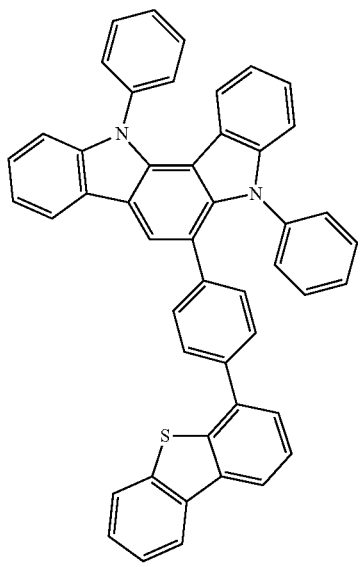

The first compound for an organic optoelectronic device and second compound for an organic optoelectronic device may variously be combined to prepare various compositions.

A composition according to an example embodiment of the present invention may include the compound represented by Chemical Formula 1C as a first host and a compound represented by Chemical Formula 2A or Chemical Formula 2C as a second host. Herein, all $Z^1$ to $Z^3$ of Chemical Formula 1C may be N.

Chemical Formula 2A may have a structure represented by Chemical Formula C-8 or Chemical Formula C-17 of Group I and *—$Y^1$-$A^1$ and *—$Y^2$-$A^2$ may be selected from B-1, B-2, and B-3 of Group II.

The second compound for an organic optoelectronic device is used with the first compound for an organic optoelectronic device in the light emitting layer and increases charge mobility and stability, and thereby luminous efficiency and life-span characteristics may be improved. In addition, a ratio of the second compound for an organic optoelectronic device and the first compound for an organic optoelectronic device may be adjusted and thereby charge mobility may be controlled. When the composition of the present invention is used as a host, a combination ratio thereof may be different according to kinds and properties of a used dopant and the first compound for an organic optoelectronic device, or when the composition of the present invention is used in an electron transport layer or an electron transport auxiliary layer, a combination ratio of compounds in the composition may be different according to kinds of a host and a dopant of EML layer of an OLED device. For example, they may be included in a weight ratio of about 1:9 to 9:1, specifically 1:9 to 8:2, 1:9 to 7:3, 1:9 to 6:4, 1:9 to 5:5, 2:8 to 8:2, 2:8 to 7:3, 2:8 to 6:4, or 2:8 to 5:5.

When the composition of the present invention is used as a host, the first compound for an organic optoelectronic device and the second compound for an organic optoelectronic device may be included in a weight ratio of 1:9 to 5:5, 2:8 to 5:5, or 3:7 to 5:5. Specifically the first compound for an organic optoelectronic device and the second compound for an organic optoelectronic device may be included in a weight ratio of 2:8 to 8:2, 3:7 to 7:3, 4:6 to 6:4, 4:6 to 8:2, or 5:5 to 8:2, for example 2:8 to 8:2 or 3:7 to 7:3. For more specific examples, a mixing ratio of the first compound for an organic optoelectronic device and the second compound for an organic optoelectronic device may be 3:7 to 5:5, for example 3:7 or 5:5. Within the ranges, efficiency and life-span may be simultaneously improved.

The composition may further include one or more organic compound in addition to the first compound for an organic optoelectronic device and the second compound for an organic optoelectronic device.

The compound for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and L and X are the same or different and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer interposed between the anode and the cathode, wherein the organic layer includes the compound for an organic optoelectronic device or the composition for an organic optoelectronic device.

For example, the organic layer may include a light emitting layer and the light emitting layer may include the compound for an organic optoelectronic device or the composition for an organic optoelectronic device of the present invention.

Specifically, the compound for an organic optoelectronic device or the composition for an organic optoelectronic device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The auxiliary layer may further include an electron transport auxiliary layer that is adjacent to the light emitting layer and the electron transport auxiliary layer may include the compound for an organic optoelectronic device, or the composition for an organic optoelectronic device.

For example, when the electron transport layer or the electron transport auxiliary layer includes the compound for an organic optoelectronic device, the compound for an organic optoelectronic device may be represented by Chemical Formula 1C or Chemical Formula 1-I.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to an embodiment.

Referring to FIG. 1, an organic optoelectronic device 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer.

The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound for an organic optoelectronic device.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.
(Preparation of Compound for Organic Optoelectronic Device)

The compound as one specific examples of the present invention was synthesized through the following steps.
(Synthesis of First Compound for Organic Optoelectronic Device)

Synthesis Example 1: Synthesis of Compound A-1

[Reaction Scheme 1]

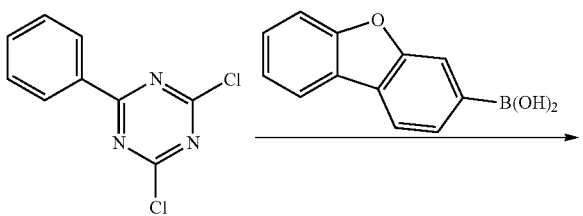

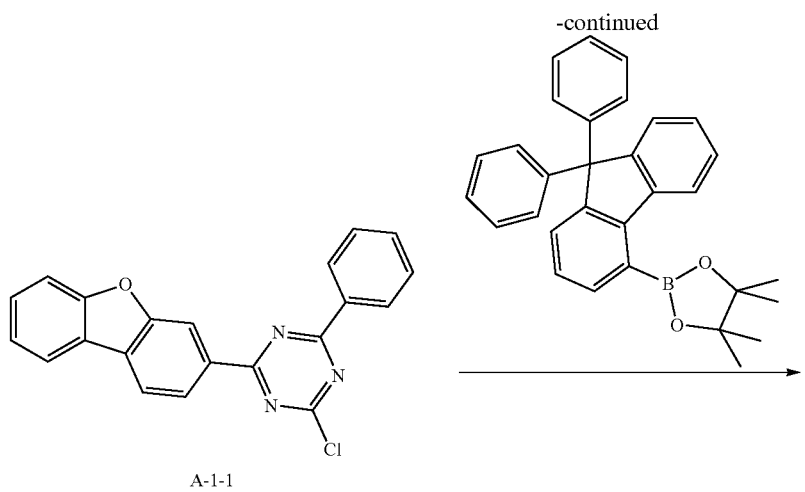

A-1-1

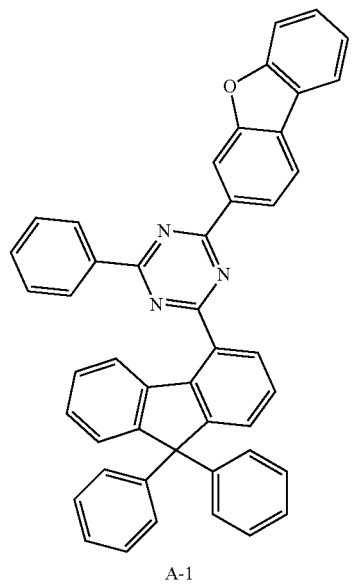

A-1 a) Synthesis of Intermediate A-1-1

22.6 g (100 mmol) of 2,4-dichloro-6-phenyltriazine was added to 100 mL of tetrahydrofuran, 100 mL of toluene, and 100 mL of distilled water in a 500 mL round-bottomed flask, 0.9 equivalent of dibenzofuran-3-boronic acid, 0.03 equivalent of tetrakistriphenylphosphine palladium, and 2 equivalent of potassium carbonate were added thereto, and the mixture was heated and refluxed under a nitrogen atmosphere. After 6 hours, the reaction solution was cooled down, an aqueous layer was removed therefrom, and an organic layer therein was dried under a reduced pressure. A solid obtained therefrom was washed with water and hexane and then, recrystallized with 200 mL of toluene to obtain 21.4 g of Intermediate A-I-i (60% of a yield).

b) Synthesis of Compound A-1

20 g (55.9 mmol) of Intermediate A-1-1 was added to 200 mL of tetrahydrofuran and 100 mL of distilled water in a 500 mL round-bottomed flask. 1.1 equivalent of a 2-(9,9-diphenyl-9H-fluorene-4-yl)-4,4,5,5-tetramethyl-1,3,2-dioxaborolane compound, 0.03 equivalent of tetrakistriphenylphosphine palladium, and 2 equivalent of potassium carbonate were added thereto, and the mixture was heated and refluxed under a nitrogen atmosphere. After 18 hours, the reaction solution was cooled down, and a solid precipitated therein was filtered and washed with 500 mL of water. The obtained solid was recrystallized with 500 mL of monochlorobenzene to obtain 26 g of Compound A-1.

Synthesis Example 2: Synthesis of Compound A-13

[Reaction Scheme 2]

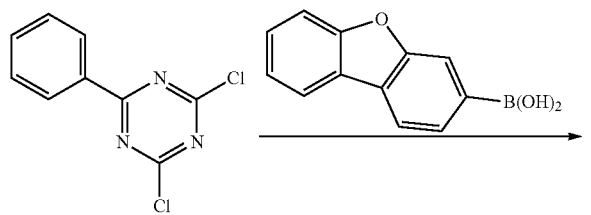

-continued

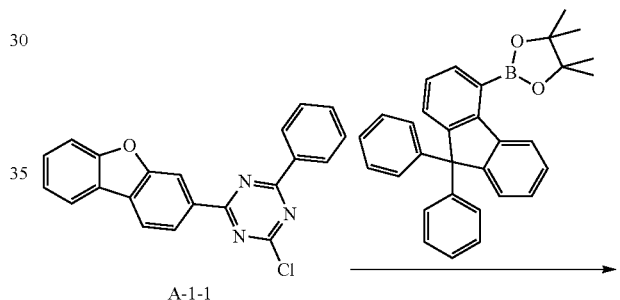

A-1-1

A-13

28 g of Compound A-13 was obtained according to the same method as Example 1 except for using a 2-(9,9-diphenyl-9H-fluoren-2-yl)-4,4,5,5-tetramethyl-1,3,2-dioxaborolane compound instead of the 2-(9,9-diphenyl-9H-fluorene-4-yl)-4,4,5,5-tetramethyl-1,3,2-dioxaborolane compound.

(Synthesis of Second Compound for Organic Optoelectronic Device)

Synthesis Example 3: Synthesis of Compound F-55

[Reaction Scheme 3]

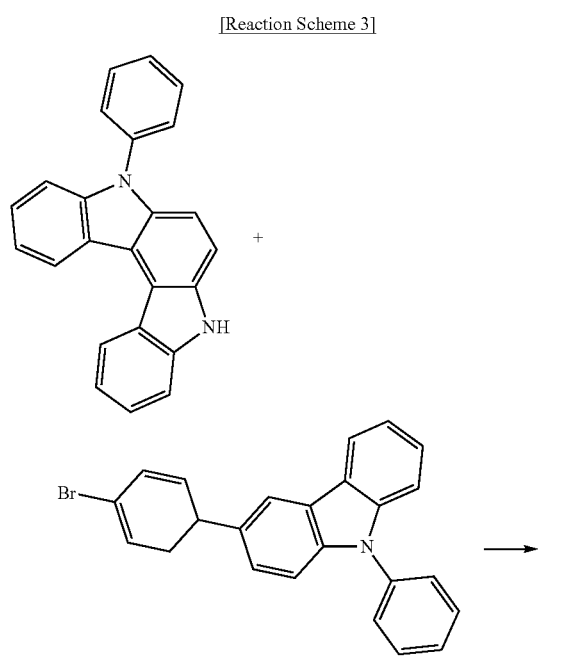

Exact Mass: 649.25

The intermediate, phenyl-indolocarbazole. were added along with 1.2 equivalent of 4-bromophenyl-carbazole, 0.03 equivalent of bisdibenzylideneacetone palladium (0), 1 equivalent of tri-t-butylphosphine, and 2 equivalent of sodium t-butoxide to toluene under a nitrogen environment, and the mixture was heated and refluxed for 16 hours. When a reaction was complete, the reaction solution was once filtered at a high temperature, treated with activated carbon while stirred again, and concentrated. The concentrated solution was dropped in methanol to obtain a solid, and a residue obtained therefrom after filtering the solid was separated and purified through column chromatography to obtain Compound F-55 (83%).

LC-Mass (theoretical value: 649.25 g/mol, measured value: M+=649 g/mol)

Comparative Synthesis Example 1: Synthesis of Comparative Compound 1

[Comparative Compound 1]

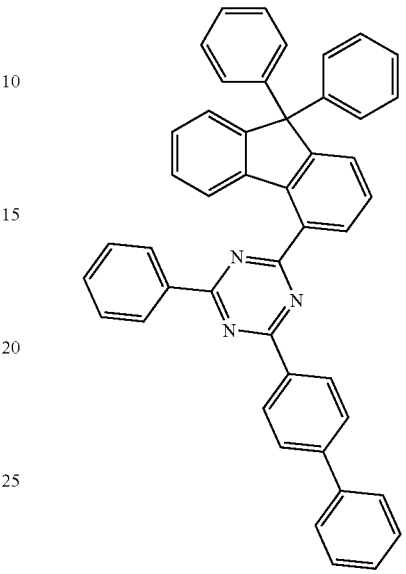

Comparative Compound 1 was obtained according to the same method as above with a reference to Paragraph 830 of Korean Patent Laid Open No. KR1542714.

(Manufacture of Organic Light Emitting Diode)

Example 1

ITO (indium tin oxide) was coated to be 1500 Å thick on a glass substrate, and the coated glass was ultrasonic wave-washed with a distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound A-1 of Synthesis Example 1 as a host and 10 wt % of tris((2-[1,1'-biphenyl]-3-yl)pyridine)iridium (III) (hereinafter, GD1) as a dopant. Subsequently, Compound D and Liq were vacuum-deposited simultaneously in a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically the following structure.

ITO/Compound A (700 Å)/Compound B (50 Å)/Compound C (1020 Å)/EML [Compound A-1:GD1=90 wt %:10 wt %] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 2

An organic light emitting diode was manufactured according to the same method as Example 1 except for forming a light emitting layer by depositing Compound A-1 and Compound E-99 in a weight ratio of 30:70. The light emitting layer of the organic light emitting diode had the following structure.

EML [Compound A-1:Compound E-99:GD1]=27 wt %:63 wt %: 10 wt %] (400 Å)

Example 3

An organic light emitting diode was manufactured according to the same method as Example 1 except for forming a light emitting layer by depositing Compound A-1 and Compound F-55 in a weight ratio of 30:70. The light emitting layer of the organic light emitting diode had the following structure.

EML [Compound A-1:Compound F-55:GD1]=27 wt %:63 wt %:10 wt %] (400 Å)

Examples 4 to 6

An organic light emitting diode was manufactured according to the same method as Examples 1 to 3 except for using Compound A-13 instead of Compound A-i The light emitting layer of the organic light emitting diode had the following structure.

Example 4: EML[Compound A-13:GD1]=90 wt %:10 wt %] 400 Å

Example 5: EML[Compound A-13:Compound E-99: GD1]=27 wt %:63 wt %:10 wt %]400 Å

Example 6: EML[Compound A-13:Compound F-55: GD1]=27 wt %:63 wt %:10 wt %]400 Å

Comparative Example 1

An organic light emitting diode was manufactured according to the same method as Example 1 except for using Comparative Compound 1 instead of Compound A-I to form a light emitting layer as shown in Table 1.

Example 7 (Electron Transport Layer (ETL))

ITO (indium tin oxide) was coated to be 1500 Å thick on a glass substrate, and the coated glass substrate was ultrasonic wave-washed with a distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 200 Å-thick light emitting layer was formed thereon by vacuum-depositing BH113 and BD370 (Manufacturer: SFC Inc.) as a blue fluorescent luminescent host and a dopant in a dopant concentration of 5 wt %. Then, Compound A-1 and Liq were vacuum-deposited simultaneously in a 1:1 weight ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

Materials used for manufacturing the organic diodes are specifically as follows.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 8

An organic light emitting diode was manufactured according to the same method as Example 7 except for using Compound A-13 instead of Compound A-I to form an electron transport layer (ETL).

Comparative Example 2

An organic light emitting diode was manufactured according to the same method as Example 7 except for using Comparative Compound 1 instead of Compound A-1 to form an electron transport layer (ETL).

Evaluation 1 (Phosphorescent Green Host)

Luminous efficiency and life-span characteristics of the organic light emitting diodes according to Examples 1 to 6 and Comparative Example 1 were evaluated. Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance. current density, and voltages (V) from the items (1) and (2).

(4) Measurement of Life-Span

T97 life-spans of the organic light emitting diodes according to Examples 1 to 3 and Comparative Example 1 were measured as a time when their luminance decreased down to 97% relative to the initial luminance (cd/m$^2$) after emitting light with 18000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$.

TABLE 1

Phosphorescence Green Host Device

| | First host | Second host | First host:Second host | Efficiency Cd/A | Life-span (T97, h) | Driving (V) |
|---|---|---|---|---|---|---|
| Example 1 | Compound A-1 | — | — | 100% | 100% | 3.67 |
| Example 2 | Compound A-1 | Compound E-99 | 3:7 | 126% | 220% | 3.62 |
| Example 3 | Compound A-1 | Compound F-55 | 3:7 | 113% | 170% | 3.49 |
| Example 4 | Compound A-13 | — | — | 100% | 110% | 3.51 |
| Example 5 | Compound A-13 | Compound E-99 | 3:7 | 133% | 250% | 3.40 |
| Example 6 | Compound A-13 | Compound F-55 | 3:7 | 120% | 180% | 3.32 |
| Comparative Example 1 | Comparative Compound 1 | — | — | 92% | 40% | 4.25 |

Referring to Table 1, the organic light emitting diodes according to Examples 1 to 6 showed all simultaneously improved driving voltage, luminous efficiency, and life-span characteristics and particularly, improved life-span and driving voltage compared with the organic light emitting diode according to Comparative Example 1.

Evaluation 2 (Electron Transport Layer (ETL))

A current density change, a luminance change, and luminous efficiency of the organic light emitting diodes according to Examples 7 and 8 and Comparative Example 2 depending on a voltage were measured.

Their specific measurement methods are the same as shown in Evaluation 1, a life-span was measured as follows, and the results are shown in Table 2.

[Measurement of Life-Span]

T97 life-spans of the organic light emitting diodes according to Example 7 and 8 and Comparative Example 2 were obtained as a time when their luminance decreased down to 97% relative to the initial luminance (cd/m$^2$) after letting the organic light emitting diodes emit light with 750 cd/m$^2$ as the initial luminance (cd/m$^2$) by measuring their luminance decreases depending on a time with a Polanonix life-span measurement system.

TABLE 2

| Devices | Electron transport layer (ETL) | Driving voltage (V) | Luminous efficiency (cd/A) | T97 (h) |
|---|---|---|---|---|
| Example 7 | Compound A-1 | 3.76 | 114% | 132% |
| Example 8 | Compound A-13 | 3.43 | 120% | 151% |
| Comparative Example 2 | Comparative Compound 1 | 4.25 | 100% | 100% |

Referring to Table 2, the organic light emitting diodes according to Examples 7 and 8 showed all simultaneously improved driving voltage, luminous efficiency, and life-span characteristics compared with the organic light emitting diode according to Comparative Example 2.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting element
105: organic layer
110: cathode
120: anode
130: emission layer
140: hole auxiliary layer

The invention claimed is:

1. A composition for an organic optoelectronic device, the composition comprising:
    a first compound for an organic optoelectronic device represented by Chemical Formula 1; and
    a second compound for an organic optoelectronic device represented by Chemical Formula 2:

[Chemical Formula 1]

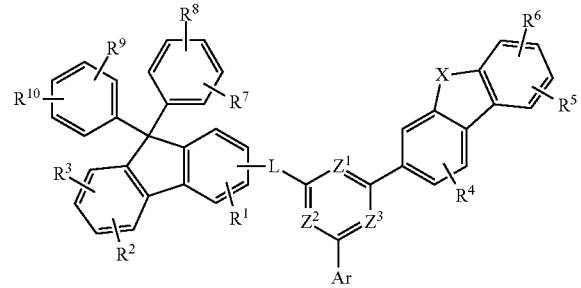

wherein, in Chemical Formula 1,
$Z^1$ to $Z^3$ are independently N or $CR^a$,
at least two of $Z^1$ to $Z^3$ are N,
X is O or S,
L is a single bond, a substituted or unsubstituted C6 to C30 arylene group, or a substituted or unsubstituted C2 to C30 heteroarylene group,
Ar is a substituted or unsubstituted C6 to C30 aryl group, and $R^a$ and $R^1$ to $R^{10}$ are independently hydrogen, deuterium, a substituted or unsubstituted C1 to C10 alkyl group, a substituted or unsubstituted C6 to C30 aryl group, or a combination thereof,

[Chemical Formula 2]

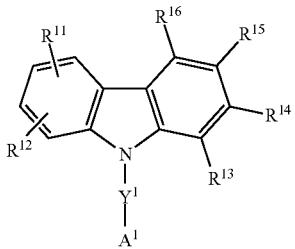

wherein, in Chemical Formula 2, $Y^1$ is a single bond, a substituted or unsubstituted C6 to C30 arylene group, or a substituted or unsubstituted C2 to C30 heteroarylene group, $A^1$ is a substituted or unsubstituted C6 to C30 aryl group, or a substituted or unsubstituted C2 to C30 heterocyclic group, $R^{11}$ to $R^{16}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and $R^{13}$ to $R^{16}$ are independently present or adjacent groups of $R^{13}$ to $R^{16}$ are linked with each other to form a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring, wherein the "substituted" refers to replacement of at least one hydrogen by deuterium, a C1 to C4 alkyl group, a C6 to C18 aryl group, or a C2 to C30 heteroaryl group.

2. The composition as claimed in claim 1, wherein the first compound is represented by Chemical Formula 1A or Chemical Formula 1C:

[Chemical Formula 1A]

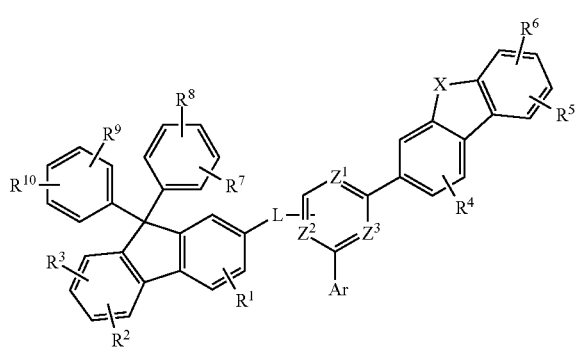

[Chemical Formula 1C]

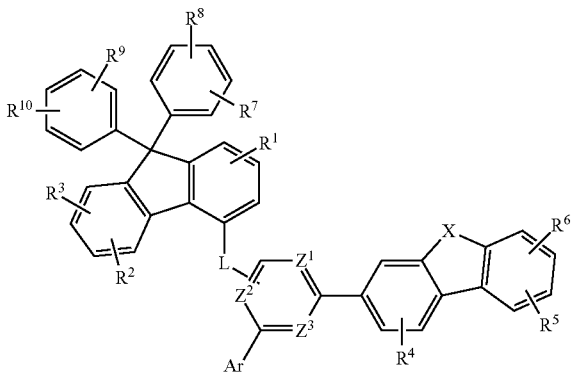

wherein, in Chemical Formula 1A and Chemical Formula 1C, $Z^1$ to $Z^3$ are independently N or $CR^a$, at least two of $Z^1$ to $Z^3$ are N, X is O or S, L is a single bond, a substituted or unsubstituted C6 to C30 arylene group, or a substituted or unsubstituted C2 to C30 heteroarylene group, Ar is a substituted or unsubstituted C6 to C30 aryl group, and $R^a$ and $R^1$ to $R^{10}$ are independently hydrogen, deuterium, a substituted or unsubstituted C1 to C10 alkyl group, a substituted or unsubstituted C6 to C30 aryl group, or a combination thereof.

3. The composition as claimed in claim 2, wherein the L of Chemical Formula 1A and Chemical Formula 1C is a single bond.

4. The composition as claimed in claim 1, wherein the first compound is represented by Chemical Formula 1-I, Chemical Formula 1-II, or Chemical Formula 1-III:

[Chemical Formula 1-I]

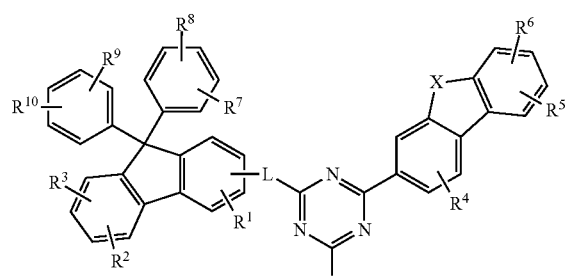

[Chemical Formula 1-II]

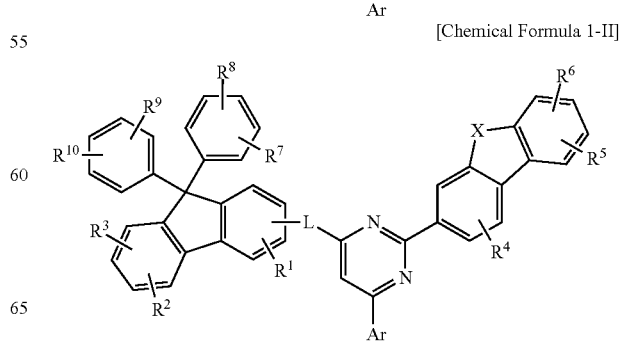

[Chemical Formula 1-III]

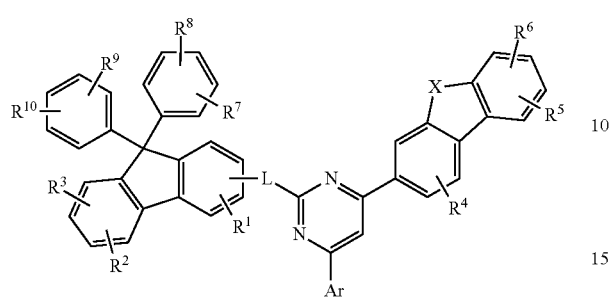

wherein, in Chemical Formula 1-I, Chemical Formula 1-II, and Chemical Formula 1-III, X is O or S, L is a single bond, a substituted or unsubstituted C6 to C30 arylene group, or a substituted or unsubstituted C2 to C30 heteroarylene group, Ar is a substituted or unsubstituted C6 to C30 aryl group, and $R^{a1}$ to $R^{a3}$ and $R^1$ to $R^{10}$ are independently hydrogen, deuterium, a substituted or unsubstituted C1 to C10 alkyl group, a substituted or unsubstituted C6 to C30 aryl group, or a combination thereof.

5. The composition as claimed in claim 4, wherein the L of Chemical Formula 1-I, Chemical Formula 1-II, and Chemical Formula 1-III is a single bond.

6. The composition as claimed in claim 1, wherein the Ar of Chemical Formula 1 is a substituted or unsubstituted phenyl group, a substituted or unsubstituted biphenyl group, a substituted or unsubstituted terphenyl group, or a substituted or unsubstituted naphthyl group.

7. The composition as claimed in claim 1, wherein the first compound is a compound of Group 1:

[Group 1]

[A-1]

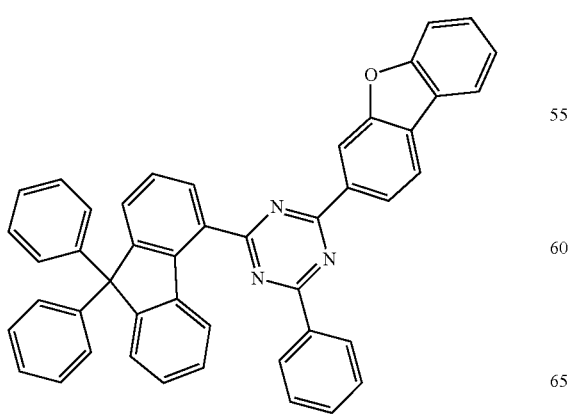

[A-2]

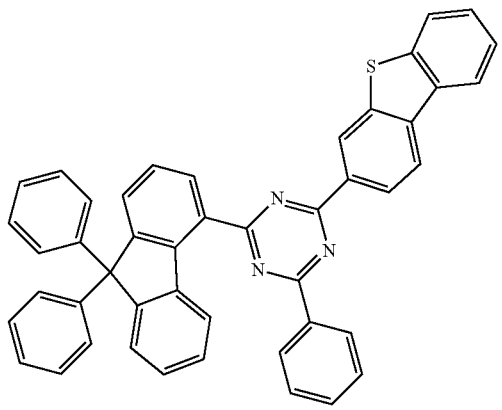

[A-3]

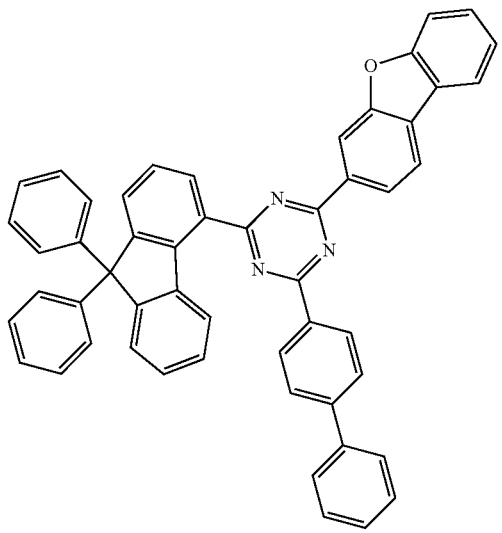

[A-4]

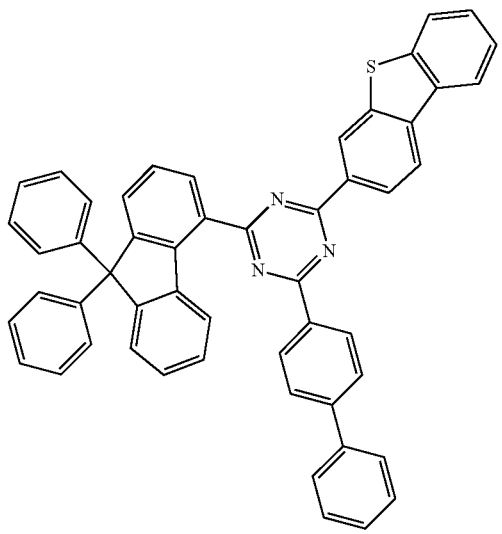

[A-5]
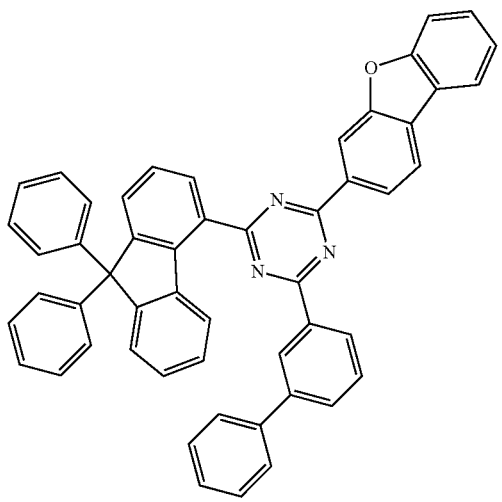
[A-6]
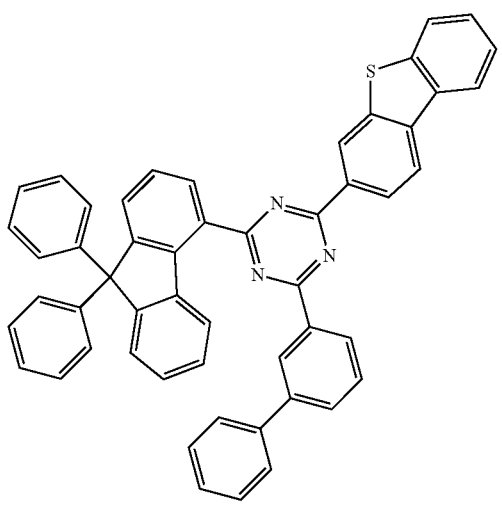
[A-7]
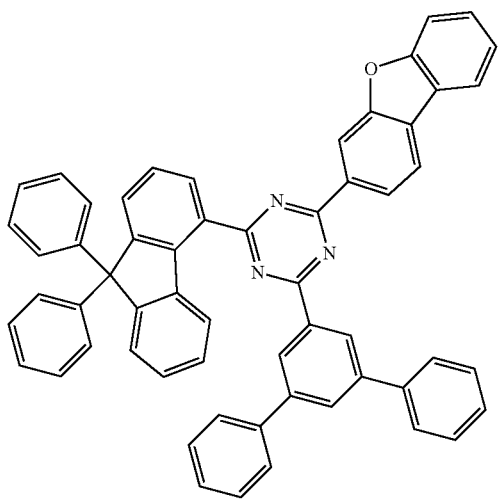
[A-8]
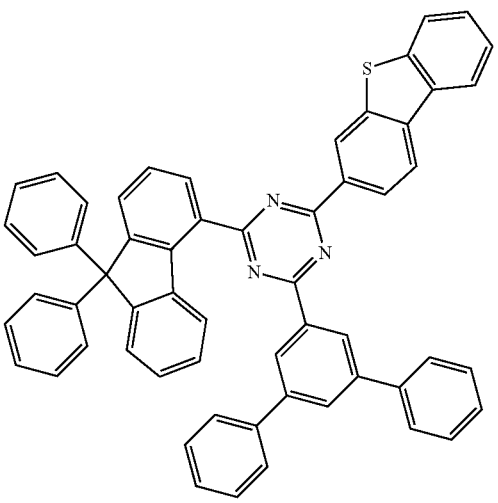
[A-9]
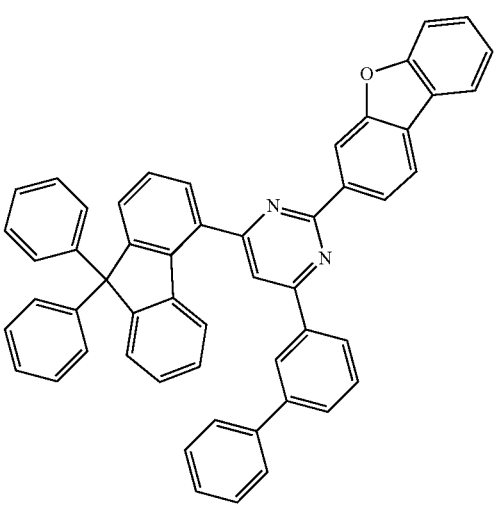
[A-10]
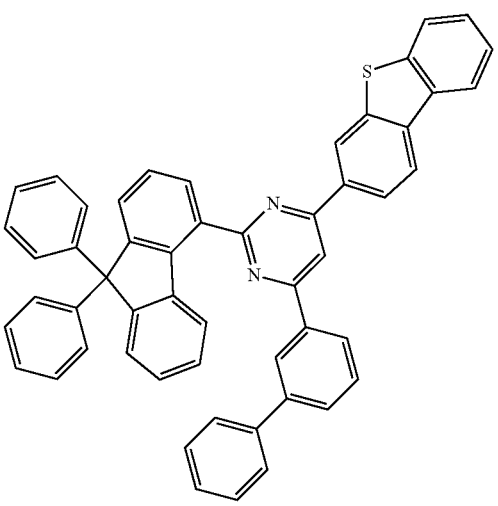

[A-11]
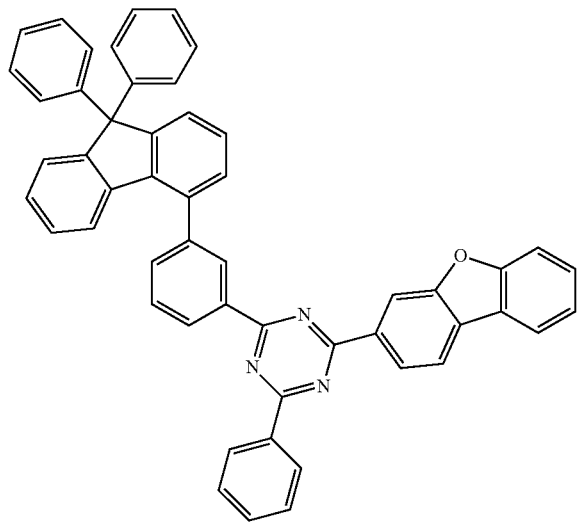
[A-12]
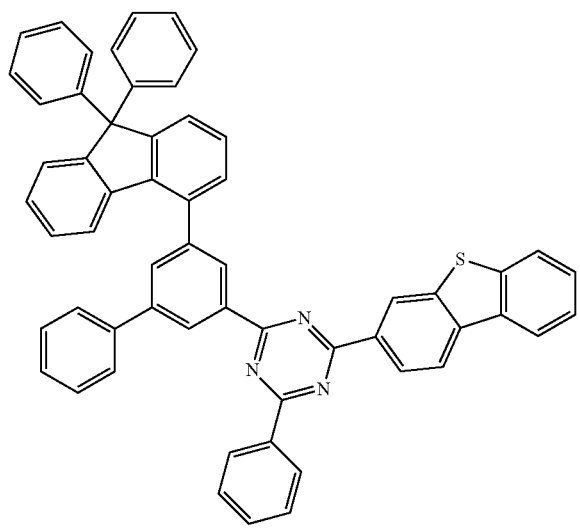
[A-13]
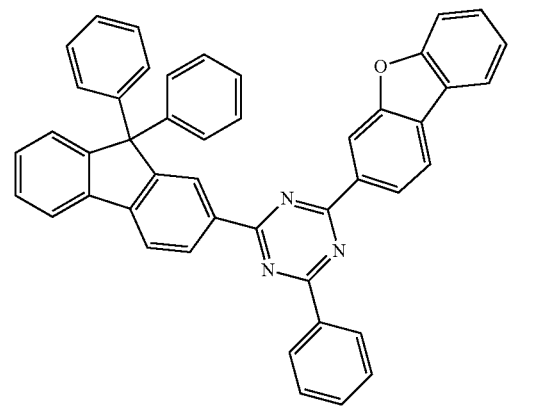
[A-14]
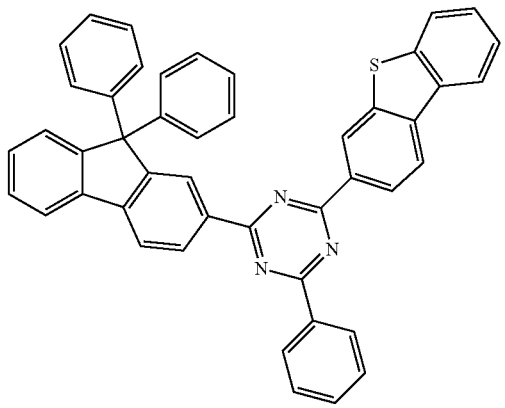
[A-15]
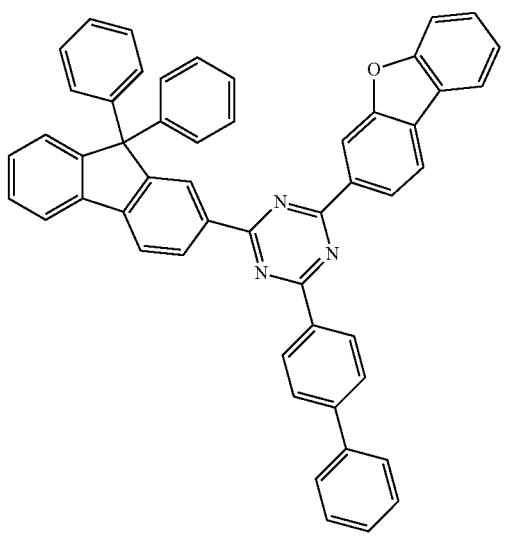
[A-16]
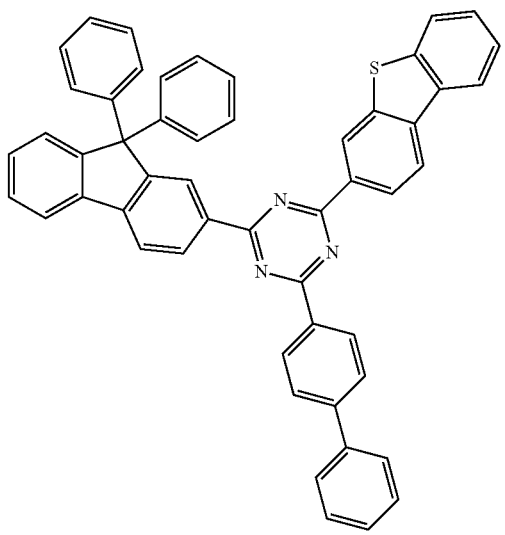

[A-17]
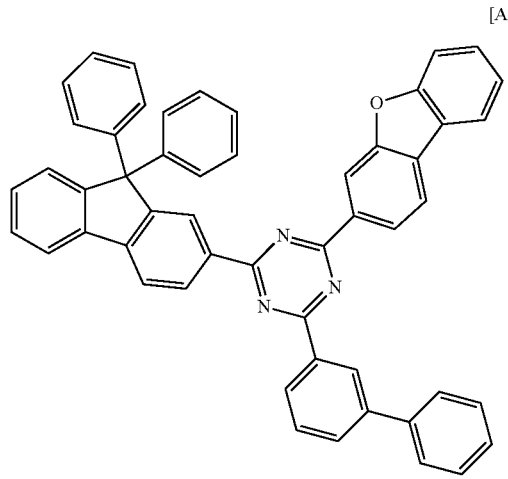
[A-18]
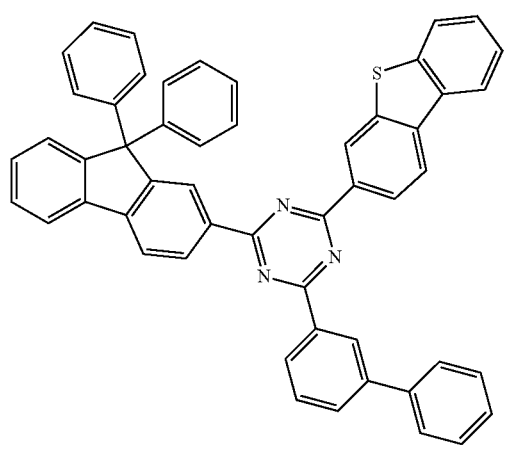
[A-19]
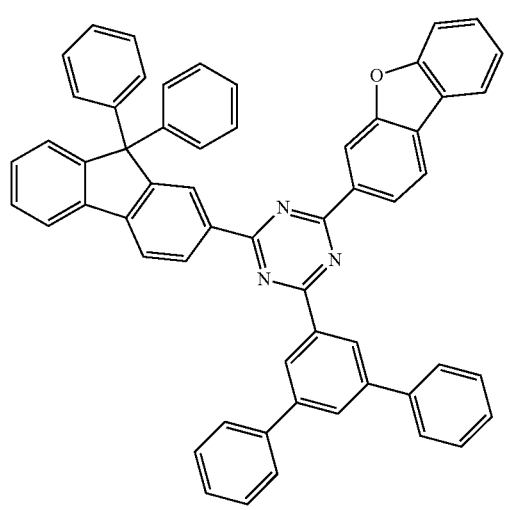
[A-20]
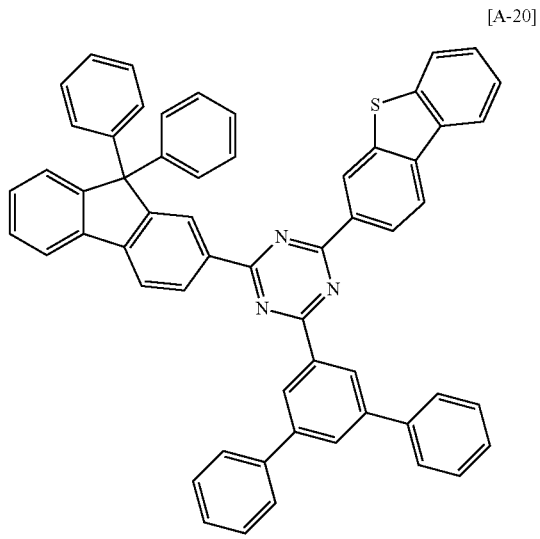
[A-21]
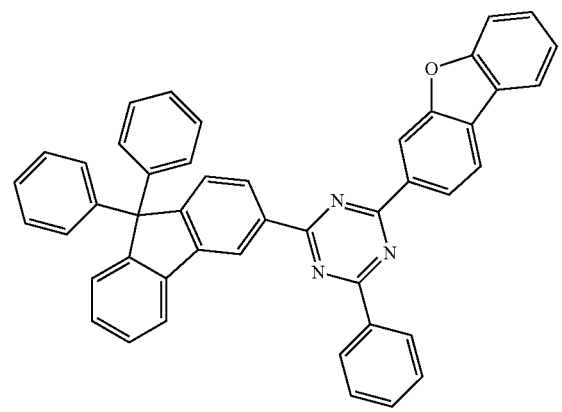
[A-22]
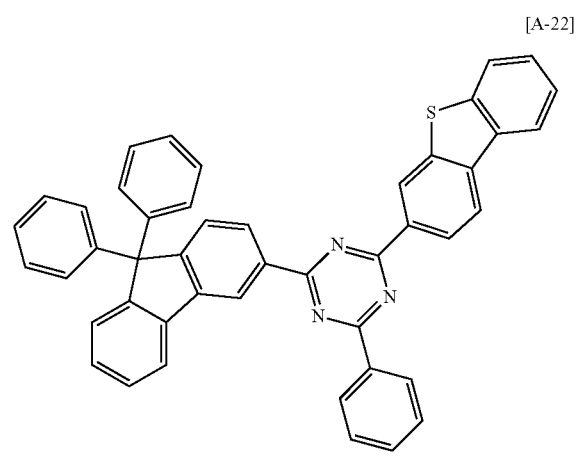

[A-23]
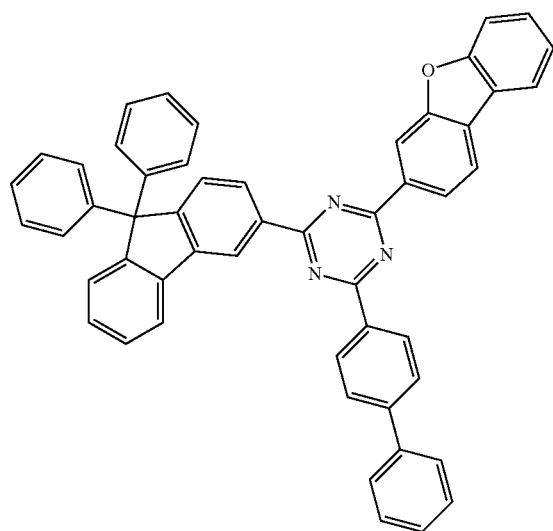
[A-24]
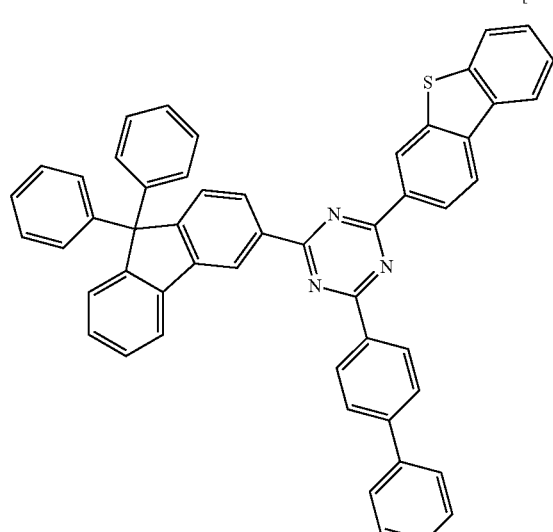
[A-25]
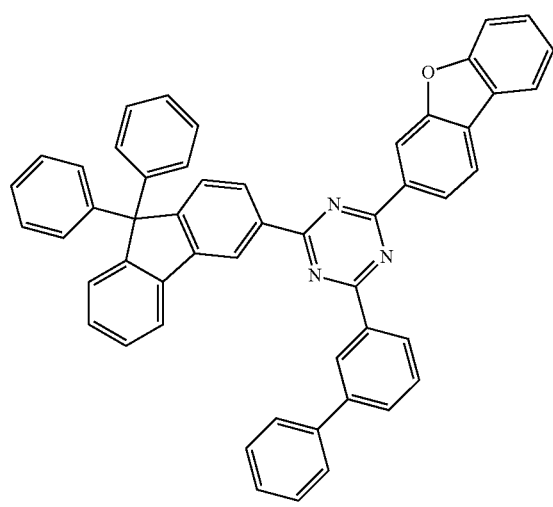
[A-26]
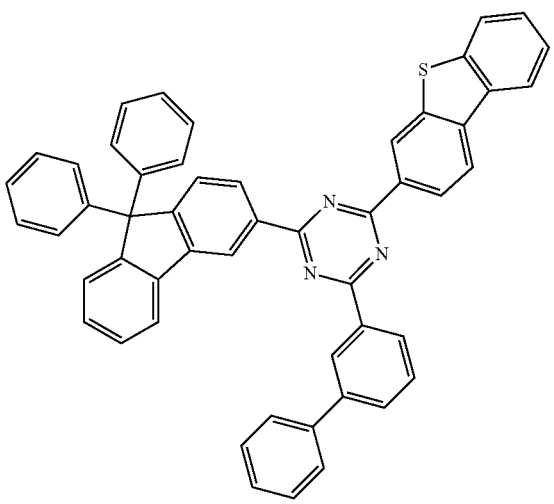
[A-27]
[A-28]
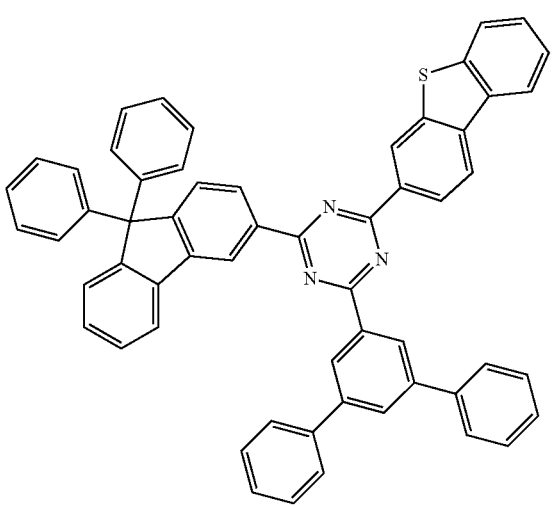

-continued

[A-29]

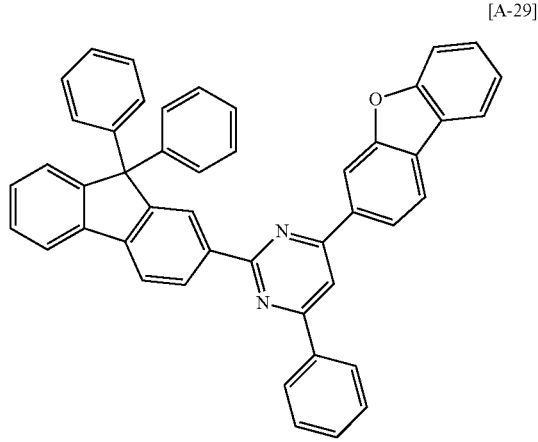

[A-30]

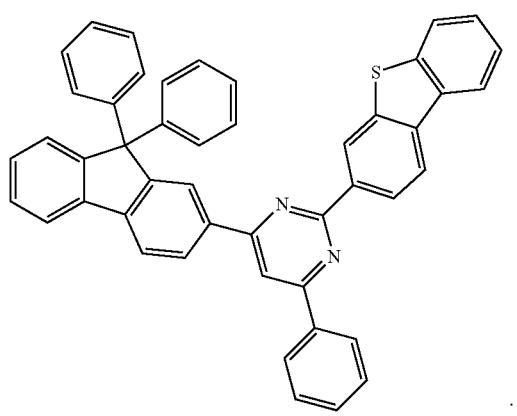

8. The composition as claimed in claim 1, wherein the second compound represented by Chemical Formula 2 is represented by Chemical Formula 2A, or a combination of Chemical Formula 2B-1 and Chemical Formula 2B-2:

[Chemical Formula 2A]

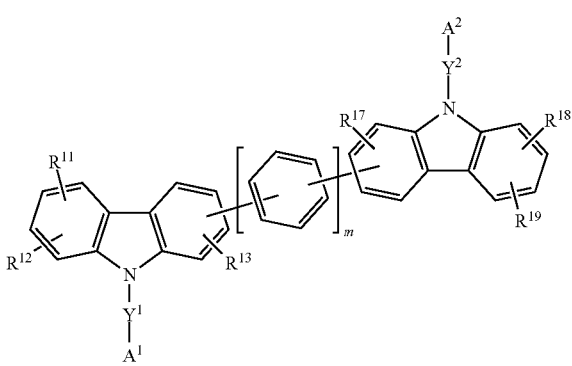

[Chemical Formula 2B-1]

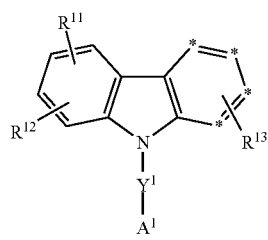

[Chemical Formula 2B-2]

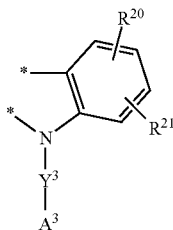

wherein, in Chemical Formula 2A, Chemical Formula 2B-1, and Chemical Formula 2B-2, $Y^1$ to $Y^3$ are independently a single bond, a substituted or unsubstituted C6 to C30 arylene group, a substituted or unsubstituted C2 to C30 heteroarylene group, or a combination thereof, $A^1$ to $A^3$ are independently substituted or unsubstituted C6 to C30 aryl group, a substituted or unsubstituted C2 to C30 heterocyclic group, or a combination thereof, $R^{11}$ to $R^{13}$ and $R^{17}$ to $R^{21}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is one of integers of 0 to 2.

9. The composition as claimed in claim 8, wherein $A^1$ to $A^3$ of Chemical Formula 2A, Chemical Formula 2B-1 and Chemical Formula 2B-2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, or a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

10. An organic optoelectronic device, comprising:
an anode and a cathode facing each other, and
at least one organic layer disposed between the anode and the cathode,
the composition for an organic optoelectronic device of claim 8.

11. The organic optoelectronic device of claim 10, wherein:
the organic layer includes a light emitting layer, and
the light emitting layer includes the composition for an organic optoelectronic device.

12. The organic optoelectronic device of claim 11, wherein the composition for an organic optoelectronic device is included as a host of the light emitting layer.

13. The organic optoelectronic device of claim 10, wherein:
the organic layer further includes at least one auxiliary layer selected from a hole injection layer, a hole transport layer, an electron blocking layer, an electron transport layer, an electron injection layer, and a hole blocking layer,
the auxiliary layer further includes an electron transport auxiliary layer that is adjacent to the light emitting layer, and
the electron transport auxiliary layer or the electron transport layer includes the composition for an organic optoelectronic device.

14. A display device comprising the organic optoelectronic device of claim 10.

\* \* \* \* \*